US012656634B2

(12) United States Patent
Purvis, II et al.

(10) Patent No.: US 12,656,634 B2
(45) **Date of Patent: *Jun. 16, 2026**

(54) ELECTRON WITHDRAWING GROUP (EWG)-CONTAINING ORGANIC MOLECULES FOR IMPROVED OPTICAL PROPERTIES IN AR/VR COMPONENTS

(71) Applicant: Meta Platforms Technologies, LLC, Menlo Park, CA (US)

(72) Inventors: Lafe Joseph Purvis, II, Redmond, WA (US); Scheherzad Alvi, Redmond, WA (US); Viachaslau Bernat, Bothell, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 397 days.

This patent is subject to a terminal disclaimer.

(21) Appl. No.: 18/355,757

(22) Filed: Jul. 20, 2023

(65) Prior Publication Data

US 2024/0151993 A1 May 9, 2024

Related U.S. Application Data

(60) Provisional application No. 63/380,848, filed on Oct. 25, 2022.

(51) Int. Cl.

| | |
|---|---|
| ***G02F 1/00*** | (2006.01) |
| ***C07C 22/08*** | (2006.01) |
| ***C07C 25/24*** | (2006.01) |
| ***C07C 205/06*** | (2006.01) |
| ***C07C 255/50*** | (2006.01) |
| ***C07C 255/51*** | (2006.01) |
| ***C07C 321/26*** | (2006.01) |

(Continued)

(52) U.S. Cl.

CPC ............ *G02F 1/0018* (2013.01); *C07C 22/08* (2013.01); *C07C 25/24* (2013.01); *C07C 205/06* (2013.01); *C07C 255/50* (2013.01); *C07C 255/51* (2013.01); *C07C 321/26* (2013.01); *C07C 323/09* (2013.01); *C07C 323/22* (2013.01); *C07F 7/081* (2013.01); *G02F 1/0316* (2013.01); *C07B 2200/13* (2013.01); *C07C 2603/24* (2017.05)

(58) Field of Classification Search

None

See application file for complete search history.

(56) References Cited

U.S. PATENT DOCUMENTS 5,882,774 A * 3/1999 Jonza .................. G02B 5/3083 428/522
6,842,217 B1 * 1/2005 Miller ..................... G02F 1/216 349/123

(Continued)

*Primary Examiner* — Sharrief I Broome
*Assistant Examiner* — Journey F Sumlar
(74) *Attorney, Agent, or Firm* — Greenberg Traurig, LLP

(57) ABSTRACT

An optical modulator includes an organic solid crystal thin film having an organic molecule and an electron withdrawing group (EWG) bonded to the organic molecule, a primary electrode disposed over a first region of the organic solid crystal thin film, and a secondary electrode disposed over a second region of the organic solid crystal thin film, wherein an optical property of the organic solid crystal thin film is configured to change in response to a changing voltage between the primary electrode and the secondary electrode.

17 Claims, 33 Drawing Sheets

A

B

(51) Int. Cl.
*C07C 323/09* (2006.01)
*C07C 323/22* (2006.01)
*C07F 7/08* (2006.01)
*G02F 1/03* (2006.01)

(56) References Cited

U.S. PATENT DOCUMENTS

2021/0263313 A1* 8/2021 Malhotra ............. G02B 5/3083
2022/0035075 A1* 2/2022 Rao .......................... G02B 1/02
2022/0082749 A1* 3/2022 Malhotra ............. G02B 5/3041
2024/0192549 A1* 6/2024 Lin ......................... G02F 1/137

* cited by examiner

A

B

A

B

A

B

A

B

A

B

B

A

A

B

Example Crystallizable Organic Molecules

Diphenylacetylene

1-Ethynyl-4-(Phenylethynyl)Benzene 1,2-Bis(Phenylethynyl)Benzene 1,4-Diphenylbutadyne 1,4-Bis(Phenylethynyl)Benzene 4'-(Phenylethynyl)Acetophenone 4-Flouro-4'-(Phenylethynyl)Benzophenone 1-Flouro-4-Phenylethynyl-Benzene 1-Flouro-4-(Phenylethynyl)-Benzene 4-[(4-Flourophenyl)Ethynyl]phenol 4-(2-Phenylethynyl)phenol 1-Methoxy-4-[(4-Methoxyohenyl)
Ethynyl]benzene 4-(Phenylethynyl)Phenylboronic Acid Pinacol Ester 4-[2-(4 Sulfanylphenyl)Ethynyl]benzenethiol Dithiomethyl Diphenylacetylene 4-[2-(4-Mercaptophenyl)Ethynyl]-Phenol 1-(Methylthio)-4-(2-Phenylethynyl)-Benzene Thiomethyl-Chloro-Diphenylacetylene 2-(2-Phenylethynyl)-Pyridine 1-Phenoxy-4-(2-Phenylethynyl)-Benzene (R)-BINOL (S)-BINOL R= F, Cl, Br, I, Ph, $NO_2$, $SO_3$, $SO_2Me$, Acetyl, Carboxyl, Aldehyde, $SO_2NH_3$.

ELECTRON WITHDRAWING GROUP (EWG)-CONTAINING ORGANIC MOLECULES FOR IMPROVED OPTICAL PROPERTIES IN AR/VR COMPONENTS

CROSS-REFERENCE TO RELATED APPLICATION

This application claims the benefit of priority under 35 U.S.C. § 119(e) of U.S. Provisional Application No. 63/380,848, filed Oct. 25, 2022, the contents of which are incorporated herein by reference in their entirety.

BRIEF DESCRIPTION OF THE DRAWINGS

The accompanying drawings illustrate a number of exemplary embodiments and are a part of the specification. Together with the following description, these drawings demonstrate and explain various principles of the present disclosure.

Figure 1:
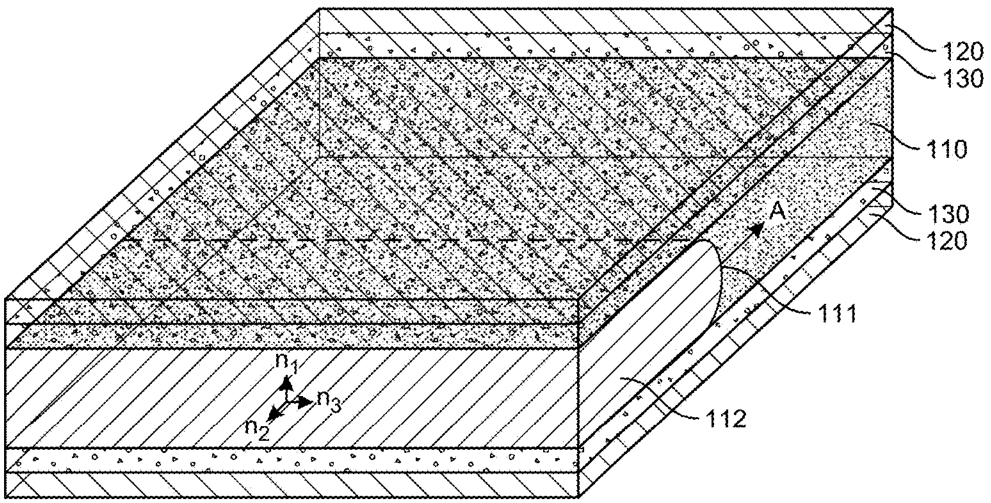
FIG. 1 illustrates example methods for manufacturing (A) a free-standing organic solid crystal material and (B) a supported organic solid crystal material according to various embodiments.
Figure 1:
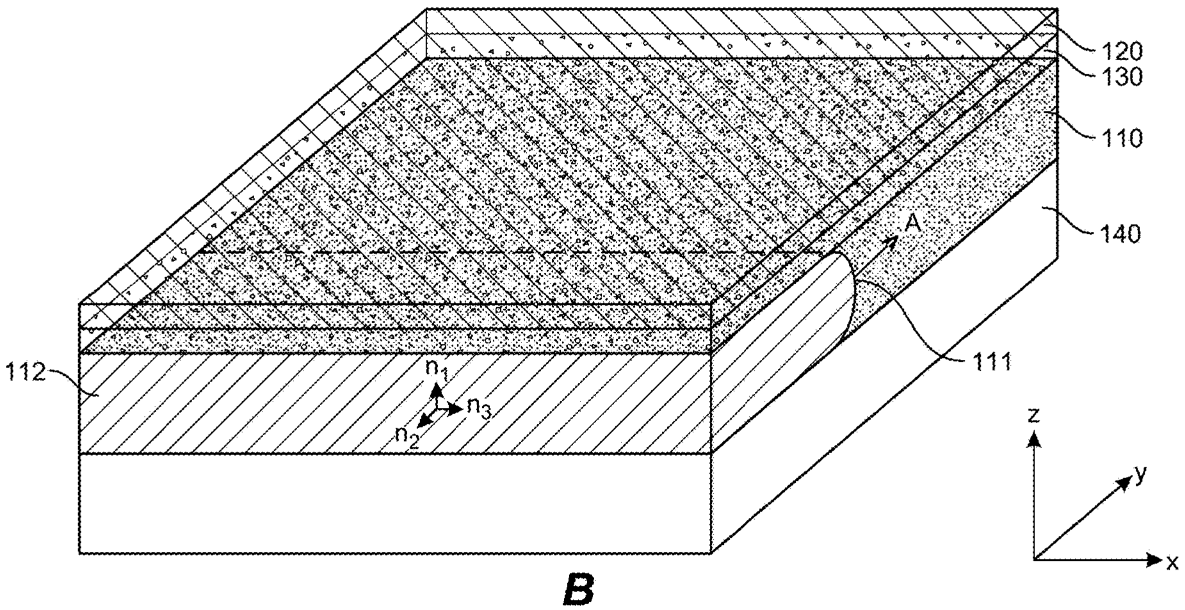

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the present disclosure covers all modifications, equivalents, and alternatives falling within the scope of the appended claims.

DETAILED DESCRIPTION OF EXEMPLARY EMBODIMENTS

Polymer and other organic materials may be incorporated into a variety of different optic and electro-optic device architectures, including passive and active optics and electroactive devices. Lightweight and conformable, one or more polymer/organic solid layers may be incorporated into wearable devices such as smart glasses and are attractive candidates for emerging technologies including virtual reality/augmented reality devices where a comfortable, adjustable form factor is desired.

Virtual reality (VR) and augmented reality (AR) eyewear devices or headsets, for instance, may enable users to experience events, such as interactions with people in a computer-generated simulation of a three-dimensional world or viewing data superimposed on a real-world view. By way of example, superimposing information onto a field of view may be achieved through an optical head-mounted display (OHMD) or by using embedded wireless glasses with a transparent heads-up display (HUD) or augmented reality (AR) overlay. VR/AR eyewear devices and headsets may be used for a variety of purposes. For example, governments may use such devices for military training, medical professionals may use such devices to simulate surgery, and engineers may use such devices as design visualization aids.

Notwithstanding recent developments, it would be advantageous to provide polymer and other organic solid materials having improved optical properties, including one or more of a controllable refractive index and birefringence, optical clarity, and optical transparency. Such materials may be formed into thin films, and a plurality of thin films may be stacked to form a multilayer.

As disclosed herein, a variety of methods may be used to manufacture a layer of an organic solid crystal (OSC) material, including gas- and liquid-phase epitaxial and non-epitaxial approaches. A resulting single layer OSC thin film or a multilayer thin film that includes plural layers of an organic solid crystal material may be incorporated into a variety of optical systems and devices. According to particular embodiments, a multilayer organic solid crystal thin film-based reflective polarizer may be incorporated into display systems to provide high broadband efficiency and high off-axis contrast. As used herein, a "thin film" may refer to a layer of material ranging in thickness from approximately 10 nm to approximately 20 micrometers, e.g., 10, 20, 50, 100, 200, 500, 1000, 2000, 5000, 10000, or 20000 micrometers, including ranges between any of the foregoing values.

By way of example, an optical assembly, such as a lens system including a circular reflective polarizer, may include a multilayer organic solid crystal thin film. Each biaxial OSC layer may be characterized by three mutually orthogonal refractive indices ($n_1$, $n_2$, $n_3$) where $n_1 \neq n_2 \neq n_3$. The multilayer thin film may include a plurality of rotationally-offset biaxially-oriented organic solid material layers. By mis-aligning (i.e., rotating) each layer with respect to an adjacent layer, such biaxially oriented multilayer thin films may enable higher signal efficiency and greater ghost image suppression than architectures using comparative materials. Organic solid crystal thin films can also be used in various projectors as a brightness enhancement layer.

As will be explained in greater detail herein, embodiments of the instant disclosure relate also to switchable optical elements that include an organic solid crystal (OSC) material layer. The OSC layer may exhibit a first refractive index in a first biased state and a second refractive index in a second biased state, and may be actively tuned across a range of refractive index values between the first refractive index and the second refractive index.

One or more source materials may be used to form an organic solid crystal thin film, including a multilayer thin film. Example organic materials include various classes of crystallizable organic semiconductors. Organic semiconductors may include small molecules, macromolecules, liquid crystals, organometallic compounds, oligomers, and polymers. Organic semiconductors may include p-type, n-type, or ambipolar polycyclic aromatic hydrocarbons, such as anthracene, phenanthrene, tolane, thiophene, pyrene, corannulene, fluorene, biphenyl, terphenyl, etc. Further example small molecules include fullerenes, such as carbon 60.

In particular embodiments, an organic solid crystal thin film may include a chiral organic compound. Anisotropic organic small molecules having chirality may be packed into polycrystalline or single crystal structures to form solid organic materials having a refractive index and birefringence that may be actively tuned via charge injection. Enantiomeric single crystals, for example, may exhibit an improved optical response to changes in charge injection. The crystal structure of OSC material having an electron-withdrawing group modified molecule may be centrosymmetric, non-centrosymmetric, or enantiomorphic/chiral.

An organic solid crystal may be characterized as centrosymmetric and may be represented by a space group selected from P1, P2/m, $P2_1/m$, P2/c, $P2_1/c$, C2/m, C2/c, Pmmm, Pnnn, Pccm, Pban, Pmma, Pnna, Pmna, Pcca, Pbam, Pccn, Pbcm, Pnnm, Pmmn, Pbcn, Pbca, Pnma, Cmmm, Cmcm, Cmca, Cccm, Cmma, Ccca, Fmmm, Fddd, Immm, Ibam, Ibcm, and Imma.

An organic solid crystal may be characterized as non-centrosymmetric and may be represented by a space group selected from Pm, Pc, Cm, Cc, Pmm2, Pmc21, Pcc2, $Pca2_1$, Pnc2, Pmn21, Pba2, Pna21, Pnn2, Cmm2, Cmc21, Ccc2, Amm2, Abm2, Ama2, Aba2, Fmm2, Fdd2, Imm2, Iba2, and Ima2.

An organic solid crystal may be characterized as enantiomorphic/chiral and may be represented by a space group selected from P1, P2, P21, C2, P222, $P222_1$, $P2_12_12$, $P2_12_12_1$, C222, $C222_1$, F222, I222, and $I2_12_12_1$.

An organic solid crystal thin film may include a racemic mixture of a chiral organic molecule. In some embodiments, an organic solid crystal thin film may include an organic crystalline phase including an organic molecule and an electron withdrawing group. Alternatively, an organic solid crystal thin film may include a single enantiomer of a chiral organic molecule, which may enable the propagation of circularly polarized light therethrough.

In further embodiments, an anisotropic organic molecule may include an electron withdrawing group (EWG). An electron withdrawing group can, by its addition to a host molecule, decrease the electron density of the host molecule either by resonance or induction. Anisotropic organic molecules may be bonded to EWGs and formed into a polycrystalline or single crystal structure to create solid organic molecules having an increased refractive index and birefringence. Such crystal structures may be actively tuned via charge injection. EWGs may improve the packing of anisotropic organic molecules by changing the polarizability of the molecule in its solid state. According to some embodiments, EWGs may have an electronegativity of at least 2.5 which may change the polarization of the organic molecule.

Greater intermolecular interactions may be induced by the incorporation of an EWG, which may generate greater dipoles within the molecule. The dipoles created from the electronegativity of the EWGs may change the polarizability of the molecule. For example, EWGs may increase a refractive index of a thin film in at least one crystallographic direction due to the intermolecular forces changing the polarizability of the of the molecules within the thin film. Example EWGs include various classes of halogens and functional groups that may have an electronegativity of 2.5 or greater. Without limitation, EWGs may include fluorine, chlorine, bromine, iodine, phenylalanine, nitrogen dioxide, sulfur trioxide, mesylate, acetyl, carboxyl, aldehyde, and sulfur ammonia.

Example compounds may include cyclic, linear and/or branched structures, which may be saturated or unsaturated, and may additionally include heteroatoms and/or saturated or unsaturated heterocycles, such as furan, pyrrole, thiophene, pyridine, pyrimidine, piperidine, and the like. Heteroatoms (e.g., dopants) may include fluorine, chlorine, nitrogen, oxygen, sulfur, phosphorus, as well as various metals. Suitable feedstock for molding solid organic semiconductor materials may include neat organic compositions, melts, solutions, or suspensions containing one or more of the organic materials disclosed herein.

Such materials may provide functionalities, including phase modulation, beam steering, wave-front shaping and correction, optical communication, optical computation, holography, and the like. Due to their optical and mechanical properties, organic solid crystals may enable high-performance devices, and may be incorporated into passive or active optics, including AR/VR headsets, and may replace comparative material systems such as polymers, inorganic materials, and liquid crystals. In certain aspects, organic solid crystals may have optical properties that rival those of inorganic crystals while exhibiting the processability and electrical response of liquid crystals.

Structurally, the disclosed organic materials may be glassy, polycrystalline, or single crystal. Organic solid crystals, for instance, may include closely packed structures (e.g., organic molecules) that exhibit desirable optical properties such as a high and tunable refractive index, and high birefringence. Anisotropic organic solid materials may include a preferred packing of molecules, i.e., a preferred orientation or alignment of molecules. Example devices may include one or more organic solid crystal thin film having a high refractive index that may be further characterized by a smooth exterior surface.

According to some embodiments, one or more organic material layers may be used to form a variety of devices, including transistors, diodes, capacitors, etc. Example transistor architectures include MOSFET, JFET, ESFET, HEMT, BJT, etc. In certain embodiments, a transistor architecture may include an organic field effect transistor (OFET), which may have a geometry selected from TGTC, BGTC, TGBC, and BGBC. Example diodes may include p-n junction, Schottky, avalanche, and PIN geometries. Example capacitors may include a parallel plate geometry. In a multilayer architecture, the composition, structure, and properties of each organic layer may be independently selected.

The present disclosure is thus generally directed to organic thin films and devices containing such thin films, and more particularly to organic solid crystal thin films and their methods of manufacture.

Due to their relatively low melting temperature, organic solid crystals may be molded to form a desired structure. Molding processes may enable complex architectures and may be more economical than the cutting, grinding, and polishing of bulk crystals. In one example, a single crystal or polycrystalline basic shape such as a sheet or cube may be partially or fully melted into a desired form and then controllably cooled to form a single crystal having an equivalent or different shape. Suitable feedstock for molding solid organic semiconductor materials may include neat organic compositions, solutions, dispersions, or suspensions. In addition, as disclosed further herein, a chemical additive may be integrated with a molding process to improve the surface roughness of a molded organic solid crystal in situ.

A process of molding an optically anisotropic crystalline or partially crystalline thin film may include operational control of the thermodynamics and kinetics of nucleation and crystal growth. In certain embodiments, a temperature during molding proximate to a nucleation region of a mold may be less than a melting onset temperature ($T_m$) of a molding feedstock, while the temperature remote from the nucleation region may be greater than the melting onset temperature. Such a temperature gradient paradigm may be obtained through a spatially applied thermal gradient, optionally in conjunction with a selective melting process (e.g., laser, soldering iron, etc.) to remove excess nuclei, leaving few nuclei (e.g., a single nucleus) for crystal growth.

High refractive index and highly birefringent organic semiconductor materials may be manufactured as a free-standing article or as a thin film deposited onto a substrate. An epitaxial or non-epitaxial growth process, for example, may be used to form an organic solid crystal (OSC) layer over a suitable substrate or within a mold. A seed layer for encouraging crystal nucleation and an anti-nucleation layer configured to locally inhibit nucleation may collectively promote the formation of a limited number of crystal nuclei within specified locations, which may in turn encourage the formation of larger organic solid crystals.

A suitable substrate or mold may be formed from a material having a softening temperature or a glass transition temperature ($T_g$) greater than the melting onset temperature ($T_m$) of the feedstock. The substrate or mold may include any suitable material, e.g., silicon, silicon dioxide, fused silica, quartz, glass, nickel, silicone, siloxanes, perfluoropolyethers, polytetrafluoroethylenes, perfluoroalkoxy alkanes, polyimide, polyethylene naphthalate, polyvinylidene fluoride, polyphenylene sulfide, and the like. For the sake of convenience, the terms "substrate" and "mold" may be used interchangeably herein unless the context indicates otherwise.

To promote nucleation and crystal growth, a selected temperature and temperature gradient may be applied to a crystallization front of a nascent thin film. The temperature and temperature gradient proximate to the crystallization front may be determined based on the selected feedstock, including its melting temperature, thermal stability, and rheological attributes. In some embodiments, a seed layer configured to promote crystal nucleation may be formed over at least a portion of a surface of a substrate or mold.

Example nucleation-promoting or seed layer materials may include one or more metallic or inorganic elements or compounds, such as Pt, Ag, Au, Al, Pb, indium tin oxide, $SiO_2$, and the like. Further example nucleation-promoting or seed layer materials may include organic compounds, such as a polyimide, polyamide, polyurethane, polyurea, polythiolurethane, polyethylene, polysulfonate, polyolefin, as well as mixtures and combinations thereof. In some examples, a nucleation-promoting material may be configured as a textured or aligned layer, such as a rubbed polyimide or photoalignment layer, which may be configured to induce directionality or a preferred orientation to an over-formed organic crystal. An anti-nucleation layer, on the other hand, may include a dielectric material. In further embodiments, an anti-nucleation layer may include an amorphous material. In example processes, crystal nucleation may occur independent of the substrate or mold. Nucleation-promoting or seed crystal may include small molecule organic single crystals such as anthracene, tolane, fluorene, pentacene, naphthalene.

In some embodiments, a surface treatment or a release layer disposed over the substrate or mold may be used to control nucleation and growth of the organic solid crystal (OSC) and later promote separation and harvesting of a bulk crystal or thin film. For instance, a coating having a solubility parameter mismatch with the deposition chemistry may be applied to the substrate (e.g., locally) to suppress interaction between the substrate and the crystallizing layer during the deposition process. Examples of such coatings include oleophobic coatings or hydrophobic coatings. A thin layer, e.g., monolayer or bilayer, of an oleophobic material or a hydrophobic material may be used to condition the substrate or mold prior to an epitaxial process. The coating material may be selected based on the substrate and/or the crystalline material. Further example coating materials include siloxanes, fluorosiloxanes, phenyl siloxanes, fluorinated coatings, polyvinyl alcohol, and other OH bearing coatings, acrylics, polyurethanes, polyesters, polyimides, and the like.

A buffer layer may be formed over the deposition surface of a substrate or mold. A buffer layer may include a small molecule that is similar to or even equivalent to the small molecule making up the organic solid crystal, e.g., an anthracene single crystal. A buffer layer may be used to tune one or more properties of the growth surface of the substrate or mold, including surface energy, wettability, crystalline or molecular orientation, etc.

The substrate or mold may include a surface that is configured to provide a desired shape and form factor to the molded organic article. For example, the substrate or mold surface may be planar, concave, or convex, and may include a three-dimensional architecture, such as surface relief gratings, or a curvature configured to form microlenses, microprisms, or prismatic lenses. That is, according to some embodiments, a substrate or mold geometry may be transferred and incorporated into a surface of an over-formed organic solid crystal thin film.

An example method for manufacturing an organic solid crystal thin film includes providing a mold, forming a layer of a nucleation-promoting material over at least a portion of a surface of the mold, and depositing a layer of molten feedstock over the surface of the mold and in contact with the layer of the nucleation-promoting material, while maintaining a temperature gradient across the layer of the molten feedstock.

During the act of molding, and in accordance with particular embodiments, a cover plate may be applied to a free surface of the feedstock layer. The cover plate may be inclined at an angle with respect to a major surface of the thin film. A force may be applied to the cover plate to generate capillary forces that facilitate mass transport of the molten feedstock, i.e., between the cover plate and the substrate and in the direction of a crystallization front of a growing crystalline thin film. In some embodiments, such as through vertical orientation of the deposition system, the force of gravity may contribute to mass transport and the delivery of molten feedstock to the crystallization front. Suitable materials for the cover plate and the substrate may independently include silicon dioxide, fused silica, high index glasses, high index inorganic crystals, and high melting temperature polymers (e.g., siloxanes, polyimides, PTFE, PFA, etc.), although further material compositions are contemplated.

According to particular embodiments, a method of forming an organic solid crystal (OSC) may include combining an organic precursor (i.e., crystallizable organic molecules) with a non-volatile medium material, forming a layer including the organic precursor and the non-volatile medium material over a surface of a substrate or mold, and processing the organic precursor layer to form an organic crystalline phase, where the organic crystalline phase may include a preferred orientation of molecules.

The act of contacting the organic precursor with the non-volatile medium material may include forming a homogeneous mixture of the organic precursor and the non-volatile medium material. In further embodiments, the act of contacting the organic precursor with the non-volatile medium material may include forming a layer of the non-volatile medium material over a surface of a substrate or mold and forming a layer of the organic precursor over the layer of the non-volatile medium material.

According to further embodiments, a method may include forming a layer of a non-volatile medium material over a surface of a mold, forming a layer of a molecular feedstock over a surface of the non-volatile medium material, the molecular feedstock including an organic solid crystal precursor, forming crystal nuclei from the organic solid crystal precursor, and growing the crystal nuclei to form an organic solid crystal thin film.

In some embodiments, the non-volatile medium material may be disposed between the mold surface and the organic precursor and may be adapted to decrease the surface roughness of the molded organic solid crystal thin film and promote its release from the mold while locally inhibiting nucleation of a crystalline phase.

Example non-volatile medium materials include liquids such as silicone oil, paraffin oil, fluorinated polymers, a polyolefin and/or polyethylene glycol. Thus, in some embodiments, a layer of a non-volatile medium material may provide a liquid surface for the growth of an organic solid crystal, such as an organic solid crystal thin film. Further example non-volatile medium materials may include crystalline materials having a melting temperature that is less than the melting temperature of the organic precursor material. In some embodiments the mold surface may be pre-treated in order to improve wetting and/or adhesion of the non-volatile medium material.

The deposition surface of a substrate or mold may include a functional layer that is configured to be transferred to the organic solid crystal after formation of the organic solid crystal in conjunction with its separation from the substrate or mold. Functional layers may include an interference coating, an AR coating, a reflectivity enhancing coating, a bandpass coating, a band-block coating, blanket or patterned electrodes, etc. By way of example, an electrode may include any suitably electrically conductive material such as a metal, a transparent conductive oxide (TCO) (e.g., indium tin oxide or indium gallium zinc oxide), or a metal mesh or nanowire matrix (e.g., including metal nanowires or carbon nanotubes).

In some embodiments, the surface roughness of the substrate itself, i.e., a crystal growth surface, may be controlled to enable the formation of large (area) organic solid crystals. By decreasing the substrate surface roughness, the number of nucleation sites may be decreased, which may enable the formation of higher quality (i.e., optical quality) thin films. In addition, by decreasing the substrate surface roughness, a contact area between the substrate and the nascent solid crystal may be decreased, which may improve releasability.

A thin film or bulk crystal of an organic semiconductor may be free-standing or disposed over a substrate. A substrate, if used, may be optically transparent. The nucleation and growth kinetics and choice of chemistry may be selected to produce a solid organic crystal thin film having areal (lateral) dimensions of at least approximately 1 cm. In a further example, an organic solid crystal fiber may have a length (axial) dimension of at least approximately 1 cm.

An organic thin film may include a surface that is planar, convex, or concave. In some embodiments, the surface may include a three-dimensional architecture, such as a periodic surface relief grating. In further embodiments, a thin film may be configured as a microlens or a prismatic lens. For instance, polarization optics may include a microlens that selectively passes and focuses one polarization of light over another. In some embodiments, a structured surface may be formed in situ, i.e., during crystal growth of the organic solid crystal. In further embodiments, a structured surface may be formed after crystal growth, e.g., using additive or subtractive processing, such as photolithography and etching.

According to some embodiments, an organic solid crystal thin film may be characterized by a preferred orientation of molecules that define a surface having a surface roughness ($R_a$) of less than approximately 10 micrometers over an area of at least approximately 1 $cm^2$. In some embodiments, at least one surface of an OSC thin film may have a surface roughness ($R_a$) of less than approximately 10000 nm, less than approximately 5000 nm, less than approximately 2000 nm, less than approximately 1000 nm, less than approximately 500 nm, less than approximately 200 nm, less than approximately 100 nm, less than approximately 50 nm, less than approximately 20 nm, less than approximately 10 nm, less than approximately 5 nm, or less than approximately 2 nm, including ranges between any of the foregoing values.

The organic crystalline phase may be single crystal or polycrystalline. In some embodiments, the organic crystalline phase may include amorphous regions. In some embodiments, the organic crystalline phase may be substantially crystalline. The organic crystalline phase may be characterized by a refractive index along at least one principal axis of at least approximately 1.4 at 589 nm and may be isotropic or anisotropic. By way of example, the refractive index of an organic crystalline phase at 589 nm and along at least one principal axis may be at least approximately 1.5, at least approximately 1.6, at least approximately 1.7, at least approximately 1.8, at least approximately 1.9, at least approximately 2.0, at least approximately 2.1, at least approximately 2.2, at least approximately 2.3, at least approximately 2.4, at least approximately 2.5, or at least approximately 2.6, including ranges between any of the foregoing values.

In some embodiments, the organic crystalline phase may be isotropic ($n_1=n_2=n_3$) or birefringent, where $n_1\neq n_2\neq n_3$, or $n_1\neq n_2=n_3$, or $n_1=n_2\neq n_3$, and may be characterized by a birefringence ($\Delta n$) of at least approximately 0.1, e.g., at least approximately 0.1, at least approximately 0.2, at least approximately 0.3, at least approximately 0.4, or at least approximately 0.5, including ranges between any of the foregoing values. In some embodiments, a birefringent organic crystalline phase may be characterized by a birefringence of less than approximately 0.1, e.g., less than approximately 0.1, less than approximately 0.05, less than approximately 0.02, less than approximately 0.01, less than approximately 0.005, less than approximately 0.002, or less than approximately 0.001, including ranges between any of the foregoing values.

In certain embodiments, an organic solid crystal thin film may be characterized by mutually orthogonal in-plane refractive indices ($n_x$ and $n_y$) and a through thickness refractive index ($n_z$), with $n_x>1.4$, $n_y>1.4$, $n_z>1.4$, $\Delta n_{xy}\geq 0.1$, $\Delta n_{xy}>\Delta n_{xz}$, and $\Delta n_{xy}>\Delta n_{yz}$.

Three axis ellipsometry data for example isotropic or anisotropic organic molecules are shown in Table 1. The data include predicted and measured refractive index values and birefringence values for 1,2,3-trichlorobenzene (1,2,3-TCB), 1,2-diphenylethyne (1,2-DPE), and phenazine. Shown are larger than anticipated refractive index values and birefringence compared to calculated values based on the HOMO-LUMO gap for each organic material composition.

TABLE 1

Index and Birefringence Data for Example Organic Semiconductors

| OSC | Predicted | Measured Index (589 nm) | | | Birefringence | | |
|---|---|---|---|---|---|---|---|
| Material | Index | $n_x$ | $n_y$ | $n_z$ | Δn(xy) | Δn(xz) | Δn(yz) |
| 1,2,3-TCB | 1.567 | 1.67 | 1.76 | 1.85 | 0.09 | 0.18 | 0.09 |
| 1,2-DPE | 1.623 | 1.62 | 1.83 | 1.63 | 0.18 | 0.01 | 0.17 |
| phenazine | 1.74 | 1.76 | 1.84 | 1.97 | 0.08 | 0.21 | 0.13 |

Organic solid crystal thin films, including multilayer organic solid crystal thin films, may be optically transparent and exhibit low bulk haze. As used herein, a material or element that is "transparent" or "optically transparent" may, for a given thickness, have a transmissivity within the visible light spectrum of at least approximately 80%, e.g., approximately 80, 90, 95, 97, 98, 99, or 99.5%, including ranges between any of the foregoing values, and less than approximately 5% bulk haze, e.g., approximately 0.1, 0.2, 0.4, 1, 2, or 4% bulk haze, including ranges between any of the foregoing values. Transparent materials will typically exhibit very low optical absorption and minimal optical scattering.

As used herein, the terms "haze" and "clarity" may refer to an optical phenomenon associated with the transmission of light through a material, and may be attributed, for example, to the refraction of light within the material, e.g., due to secondary phases or porosity and/or the reflection of light from one or more surfaces of the material. As will be appreciated, haze may be associated with an amount of light that is subject to wide angle scattering (i.e., at an angle greater than 2.5° from normal) and a corresponding loss of transmissive contrast, whereas clarity may relate to an amount of light that is subject to narrow angle scattering (i.e., at an angle less than 2.5° from normal) and an attendant loss of optical sharpness or "see through quality."

In some embodiments, one or more organic solid crystal thin film layers may be stacked to form a multilayer. A multilayer thin film may be formed by clocking and stacking individual layers. That is, in an example "clocked" multilayer stack, an in-plane angle of refractive index misorientation between neighboring layers may range from approximately 1° to approximately 90°, e.g., 1, 2, 5, 10, 20, 30, 40, 45, 50, 60, 70, 80, or 90°, including ranges between any of the foregoing values.

In example multilayer architectures, the thickness of each layer may be determined from an average value of in-plane refractive indices ($n_2$ and $n_3$), where $(n_2+n_3)/2$ may be greater than approximately 1.4, e.g., greater than 1.4, greater than 1.45, greater than 1.5, greater than 1.55, or greater than 1.6. Generally, the thickness of a given layer may be inversely proportional to the arithmetic average of its in-plane indices. In a similar vein, the total number of layers in a multilayer stack may be determined from the in-plane birefringence ($|n_3-n_2|$), which may be greater than approximately 0.05, e.g., greater than 0.05, greater than 0.1, or greater than 0.2.

According to some embodiments, for a given biaxially-oriented organic solid material layer within a multilayer stack, the out-of-plane index ($n_1$) may be related to the in-plane refractive indices ($n_2$ and $n_3$) by the relationship $$n_1 = \frac{1}{2\pi}\int_0^{2\pi}\sqrt{(n_2\sin\varphi)^2 + (n_3\cos\varphi)^2}\,d\varphi,$$

where φ represents a rotation angle of a refractive index vector between adjacent layers. The variation in $n_1$ may be less than ±0.7, less than ±0.6, less than ±0.5, less than ±0.4, less than ±0.3, or less than ±0.2.

In lieu of, or in addition to, molding, further example deposition methods for forming organic solid crystals include vapor phase growth, solid state growth, melt-based growth, solution growth, etc., optionally in conjunction with a suitable substrate and/or seed crystal. A substrate may be organic or inorganic. By way of example, thin film solid organic materials may be manufactured using one or more processes selected from chemical vapor deposition and physical vapor deposition. Further coating processes, e.g., from solution, may include 3D printing, ink jet printing, gravure printing, doctor blading, spin coating, and the like. Such processes may induce shear during the act of coating and accordingly may contribute to crystallite or molecular alignment and a preferred orientation of crystallites and/or molecules within an organic solid crystal thin film. A still further example method may include pulling a free-standing crystal from a melt. According to some embodiments, solid-, liquid-, or gas-phase deposition processes may include epitaxial processes.

As used herein, the terms "epitaxy," "epitaxial" and/or "epitaxial growth and/or deposition" refer to the nucleation and growth of an organic solid crystal on a deposition surface where the organic solid crystal layer being grown assumes the same crystalline habit as the material of the deposition surface. For example, in an epitaxial deposition process, chemical reactants may be controlled, and the system parameters may be set so that depositing atoms or molecules alight on the deposition surface and remain sufficiently mobile via surface diffusion to orient themselves according to the crystalline orientation of the atoms or molecules of the deposition surface. An epitaxial process may be homogeneous or heterogeneous.

In accordance with various embodiments, the optical and electrooptic properties of an organic solid crystal may be tuned using doping and related techniques. Doping may influence the polarizability of an organic solid crystal, for example. The introduction of dopants, i.e., impurities, into an organic solid crystal, may influence, for example, the highest occupied molecular orbital (HOMO) and lowest unoccupied molecular orbital (LUMO) bands and hence the band gap thereof, induced dipole moment, and/or molecular/crystal polarizability. Doping may be performed in situ, i.e., during epitaxial growth, or following epitaxial growth, for example, using ion implantation or plasma doping. In exemplary embodiments, doping may be used to modify the electronic structure of an organic solid crystal without damaging molecular packing or the crystal structure itself. A post-implantation annealing step may be used to heal crystal defects introduced during ion implantation. Annealing may include rapid thermal annealing or pulsed annealing, for example.

Doping changes the electron and hole carrier concentrations of a host material at thermal equilibrium. A doped organic solid crystal may be p-type or n-type. As used herein, "p-type" refers to the addition of impurities to an organic solid crystal that creates a deficiency of valence electrons, whereas "n-type" refers to the addition of impurities that contribute free electrons to an organic solid crystal. Without wishing to be bound by theory, doping may influence "π-stacking" and "π-π interactions" within an organic solid crystal.

Example dopants include Lewis acids (electron acceptors) and Lewis bases (electron donors). Particular examples include charge-neutral and ionic species, e.g., Brønsted acids and Brønsted bases, which in addition to the aforementioned processes may be incorporated into an organic solid crystal by solution growth or co-deposition in the vapor phase.

In particular embodiments, a dopant may include an organic molecule, an organic ion, an inorganic molecule, or an inorganic ion. A doping profile may be homogeneous or localized to a particular region (e.g., depth) of an organic solid crystal.

During nucleation and growth, the orientation of the in-plane axes of an OSC thin film may be controlled using one or more of substrate temperature, deposition pressure, solvent vapor pressure, or non-solvent vapor pressure. High refractive index and highly birefringent organic solid crystal thin films may be supported by a substrate or mold or removed therefrom to form a free-standing thin film. A substrate, if used, may be rigid or deformable.

A layer of an organic solid crystal (OSC) may be disposed over an electrode or between a pair of electrodes where an applied voltage, e.g., between the electrodes, may be used to tune one or more optical properties of the OSC layer. In accordance with particular embodiments, an optical modulator may include an active layer of an organic solid crystalline phase, a primary electrode disposed over a first portion of the active layer, and a secondary electrode disposed over a second portion of the active layer, where an optical property of the active layer has a first value along a chosen direction in a first biased state and a second value along the chosen direction in a second biased state. The optical property may include refractive index, birefringence, and/or the absorption of visible light.

Disclosed are organic solid crystals having an actively tunable refractive index and birefringence. Methods of manufacturing such organic solid crystals may enable control of their surface roughness independent of surface features (e.g., gratings) and may include the formation of an organic article therefrom. A variable and controllable refractive index architecture may be incorporated into and enable various optic and photonic devices and systems.

According to various embodiments, an organic article including an organic solid crystal (OSC) may be integrated into an optical component or device, such as an OFET, organic photovoltaic (OPV), organic light emitting diode (OLED), etc., and may be incorporated into an optical element such as a waveguide, Fresnel lens (e.g., a cylindrical Fresnel lens or a spherical Fresnel lens), grating, photonic integrated circuit, birefringent compensation layer, reflective polarizer, index matching layer (LED/OLED), holographic data storage element, and the like.

As used herein, a grating is an optical element having a periodic structure that is configured to disperse or diffract light into plural component beams. The direction or diffraction angles of the diffracted light may depend on the wavelength of the light incident on the grating, the orientation of the incident light with respect to a grating surface, and the spacing between adjacent diffracting elements. In certain embodiments, grating architectures may be tunable along one, two, or three dimensions. Optical elements may include a single layer or a multilayer OSC architecture.

As will be appreciated, one or more characteristics of organic solid crystals may be specifically tailored for a particular application. For many optical applications, for instance, it may be advantageous to control crystallite size, surface roughness, mechanical strength and toughness, and the orientation of crystallites and/or molecules within an organic solid crystal thin film or fiber.

The active modulation of refractive index may improve the performance of photonic systems and devices, including passive and active optical waveguides, resonators, lasers, optical modulators, etc. Further example active optics include projectors and projection optics, ophthalmic high index lenses, eye-tracking, gradient-index optics, Pancharatnam-Berry phase (PBP) lenses, pupil steering elements, microlenses, optical computing, fiber optics, rewritable optical data storage, all-optical logic gates, multi-wavelength optical data processing, optical transistors, etc.

Features from any of the embodiments described herein may be used in combination with one another in accordance with the general principles described herein. These and other embodiments, features, and advantages will be more fully understood upon reading the following detailed description in conjunction with the accompanying drawings and claims.

The following will provide, with reference to FIGS. 1-37, detailed descriptions of organic solid crystals, their methods of manufacture, and potential applications. The discussion associated with FIG. 1 relates to example mold-based processes for forming an organic solid crystal thin film. The discussion associated with FIG. 2 relates to the structure and properties of example organic solid crystals manufactured with and without a non-volatile medium material. The discussion associated with FIGS. 3-9 includes a description of example epitaxial and non-epitaxial growth processes for forming organic solid crystals. The discussion associated with FIGS. 10-23 includes a description of the architecture and performance of example organic solid crystals and organic solid crystal-containing optical modulators.

The discussion associated with FIGS. 24-28 includes a description of example manufacturing methods and apparatus for forming organic solid crystal thin films. The discussion associated with FIGS. 29-32 includes a description of example organic molecules suitable for the manufacture of organic solid crystals. The discussion associated with FIG. 33 includes a description of a circular reflective polarizer that may include a multilayer organic solid crystal thin film having a biaxial refractive index. The discussion associated with FIG. 34 includes a description of the orientation of an in-plane refractive index ($n_3$) in an example multilayer organic solid crystal thin film. The discussion associated with FIG. 35 includes a description of the performance of an example circular reflective polarizer that includes a multilayer organic solid crystal thin film having a biaxial refractive index. The discussion associated with FIGS. 36 and 37 relates to exemplary virtual reality and augmented reality devices that may include one or more organic solid crystal thin films as disclosed herein.

Turning to FIG. 1, shown schematically are example manufacturing architectures that may be implemented in accordance with certain methods of forming an organic solid crystal thin film. In some embodiments, a layer of a crystallizable organic precursor may be deposited between mold surfaces or over a surface of a substrate and processed to form an organic solid crystal thin film. The crystallizable organic precursor may include one or more crystallizable organic molecules.

Referring to FIG. 1A, shown at an intermediate stage of fabrication, the organic precursor layer 110 may be disposed between upper and lower mold bodies 120, which may be respectively coated with upper and lower layers of a non-volatile medium material 130. The non-volatile medium material layers 130 may include an anti-nucleation layer. Following processing to induce nucleation and growth of the organic solid crystal, the resulting organic solid crystal thin film 112 may be removed from the mold 120. Exemplary processing steps may include zone annealing. The organic solid thin film 112 may be birefringent (e.g., $n_1 \neq n_2 \neq n_3$) and may be characterized by a high refractive index (e.g., $n_2 > 1.4$ and/or $n_3 > 1.4$).

Referring to FIG. 1B, shown is a further manufacturing architecture for forming a supported organic solid crystal thin film. In the architecture of FIG. 1B, at an intermediate stage of fabrication, a crystallizable organic precursor layer 110 may be disposed over a substrate 140. An upper mold body 120 may overlie the organic precursor layer 110, and a non-volatile medium material layer 130 may be located between the mold 120 and the organic precursor layer 110. The layer of non-volatile medium material 130 may directly overlie the organic precursor layer 110 and may be configured to control the surface roughness of an upper surface of the organic solid crystal thin film 112 during crystal growth. In accordance with certain embodiments, in FIG. 1A and FIG. 1B, a direction of movement of a crystallization front 111 during crystal growth is denoted with an arrow A.

Figure 2:
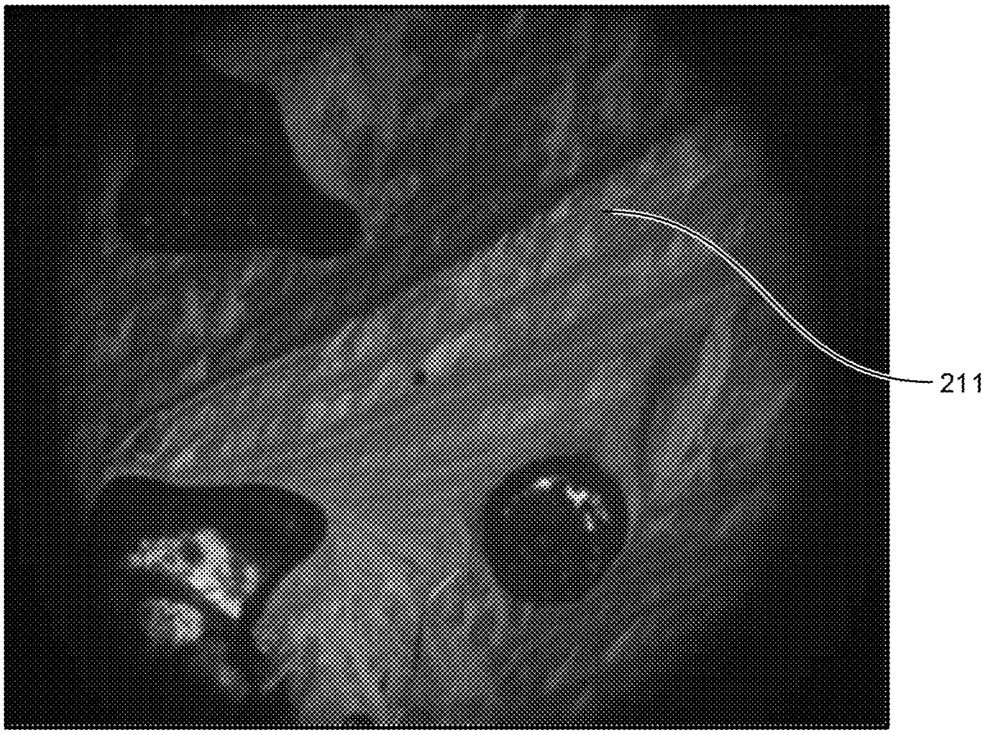
FIG. 2 shows cross-polarized microscope images of an organic solid crystal manufactured (A) without a non-volatile medium material and (B) with a non-volatile medium material according to some embodiments.
Figure 2:
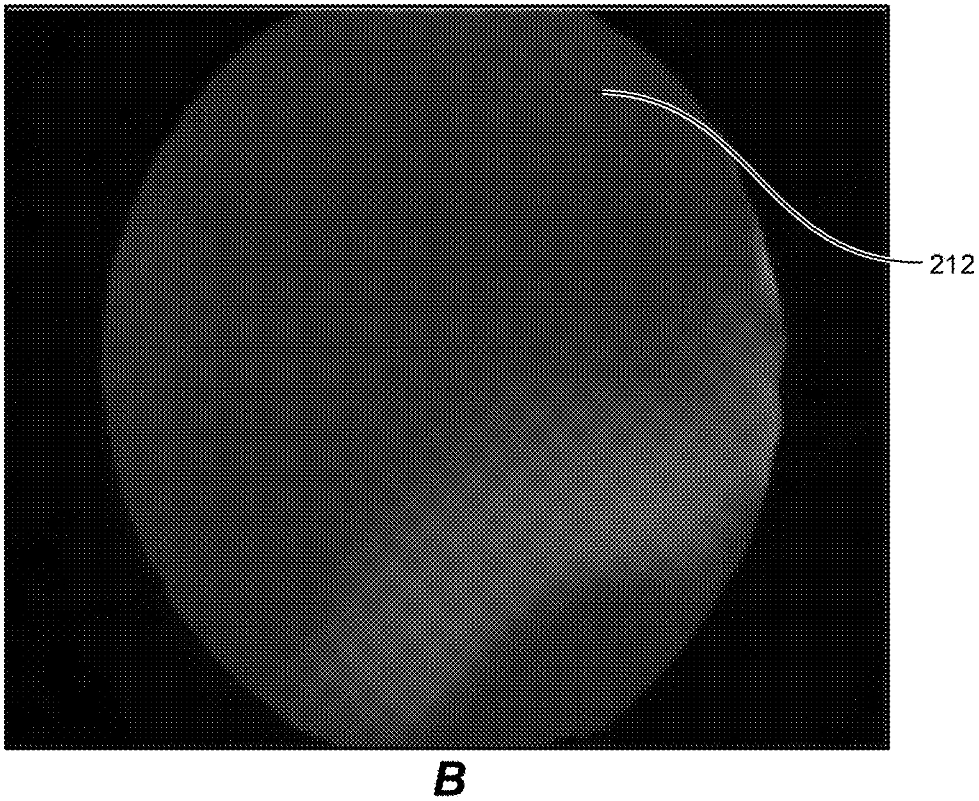

Referring to FIG. 2, shown are polarized optical microscope images of organic solid crystal thin films formed using a mold-based method. The thin films 211, 212 were manufactured (A) without using a layer of non-volatile medium material, and (B) with a layer of non-volatile medium material pre-disposed over a surface of the mold (for example, using a method illustrated in FIG. 1A or FIG. 1B). The improved surface morphology associated with use of the non-volatile medium material layer is evident in the appearance of organic solid thin film 212 in FIG. 2B.

Figure 3:
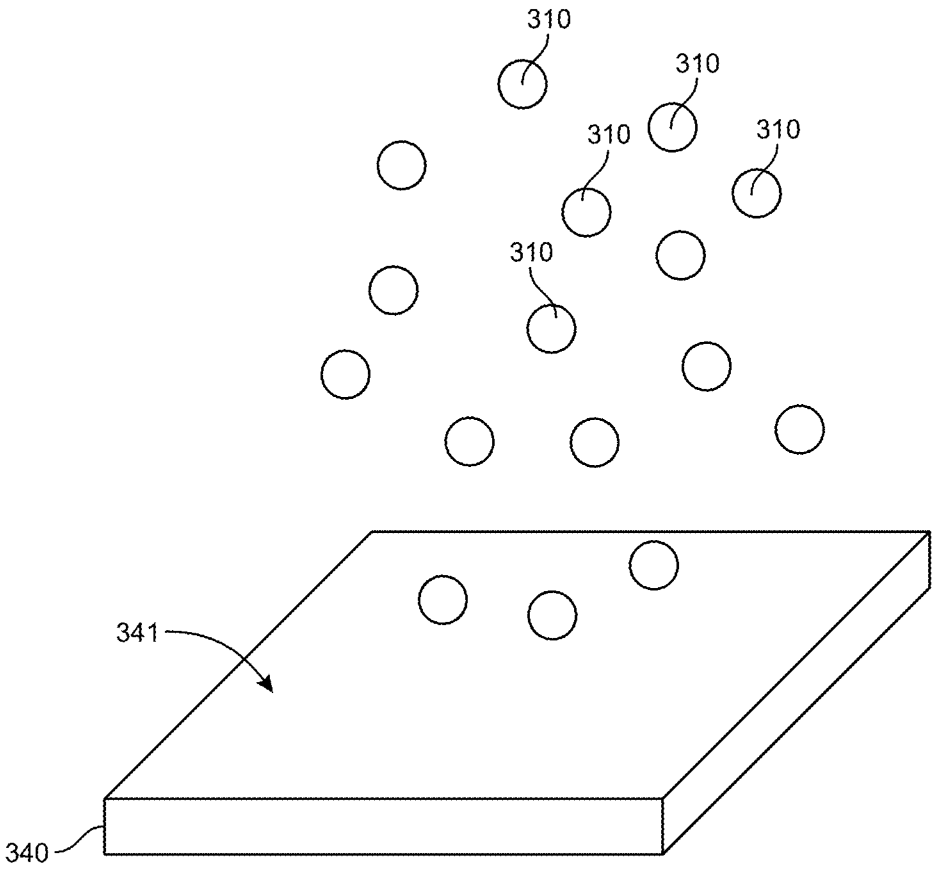
FIG. 3 is a schematic representation of a vapor deposition-based epitaxial growth process for forming organic solid crystals according to some embodiments.

An example vapor phase epitaxial growth process for forming an organic solid crystal thin film is illustrated schematically in FIG. 3. Vaporized molecules 310 of an organic solid crystal material may be directed, e.g., within a vacuum chamber (not shown), to a deposition surface 341 of a substrate 340 to form a layer of an organic solid crystal over the substrate. The choice of solvent, concentration of the vaporized molecules, substrate temperature, temperature gradient(s), gas pressure, etc. may be used to control the gas phase mobility of the molecules 310, the adsorption and desorption rates of the molecules 310, and the crystallization rate and crystal structure of the organic solid crystal thin film.

Figure 4:
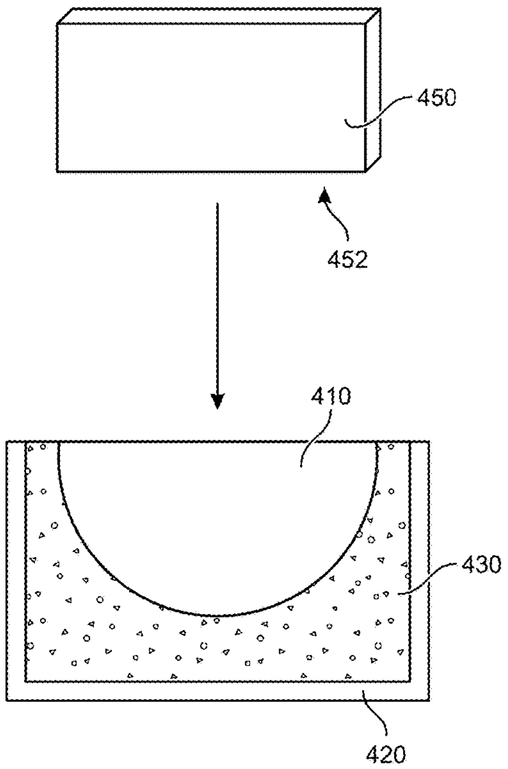
FIG. 4 is a schematic representation of a melt-based epitaxial growth process for forming organic solid crystals according to some embodiments.

A further example epitaxial growth process for forming an organic solid crystal is illustrated schematically in FIG. 4. In the method of FIG. 4, an organic crystal melt 410 may be contained and heated within a crucible 420. The crucible 420 may be formed from a glass or glass ceramic material, for example. The organic crystal melt 410 may be directly in contact with a non-volatile medium material 430 contained by the crucible 420. The non-volatile medium material 430 may include silicone oil, paraffin oil, a fluorinated polymer or fluorinated oligomer, polyethylene glycol, polyolefin, and the like.

A seed crystal 450 may be contacted with the organic crystal melt 410 and optionally drawn from the melt phase at a desired rate, e.g., under continuous operation, to form an organic solid crystal. The seed crystal 450 may include an organic solid crystal material. In some embodiments, the composition of the organic crystal melt 410 and the composition of the seed crystal 450 may be equivalent or substantially equivalent. The seed crystal 450 may have a planar or non-planar contact surface 452 that contacts the melt phase, which may be chosen to control the shape (e.g., curvature) of an over-formed organic solid crystal. In some embodiments, crucible 420 may be configured as a mold and the organic crystal melt 410 may crystallize within crucible 420 to form an organic solid crystal.

Figure 5:
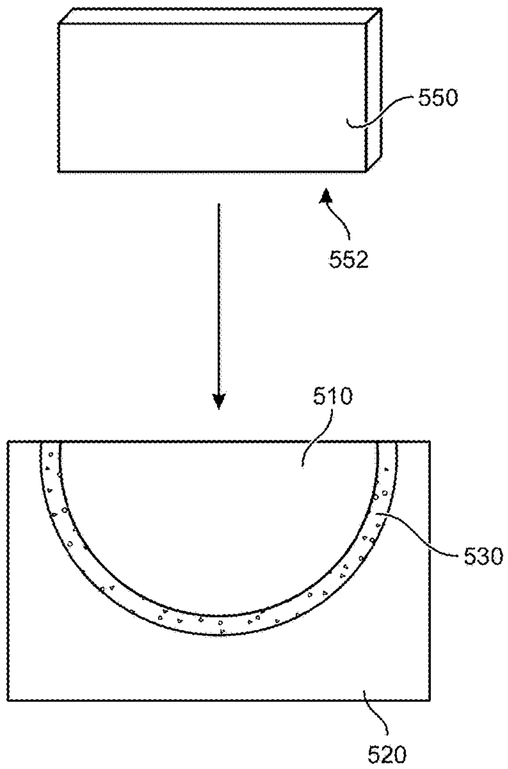
FIG. 5 is a schematic representation of a melt-based epitaxial growth process for forming organic solid crystals according to further embodiments.

A still further example epitaxial growth process and process architecture for forming an organic solid crystal is illustrated schematically in FIG. 5. In the method of FIG. 5, an organic crystal melt 510 may be contained and heated within a crucible 520. The crucible 520 may be configured to provide mechanical support and may include, for example, a glass or glass ceramic material. The organic crystal melt 510 may be directly in contact with a layer of a non-volatile medium material 530 overlying an inner surface of the crucible 520. The non-volatile medium material 530 may include silicone oil, paraffin oil, a fluorinated polymer or fluorinated oligomer, polyethylene glycol, polyolefin, and the like. In the illustrated embodiment, the non-volatile medium material layer 530 may include a conformal layer of free-standing molecules (e.g., an oil or a brushed layer of a polymer, oligomer, or small molecules such as silane or a fluorinated polymer).

Seed crystal 550 may be contacted with the organic crystal melt 510 and optionally drawn from the melt phase at a desired rate, e.g., under continuous operation, to form an organic solid crystal. The seed crystal 550 may include an organic solid crystal material. In some embodiments, the organic crystal melt 510 and the seed crystal 550 may be compositionally equivalent or substantially equivalent. In some embodiments, the seed crystal 550 may have a planar or non-planar contact surface 552, which may be chosen to control the shape (e.g., curvature) of an over-formed organic solid crystal. In some embodiments, crucible 520 may be configured as a mold, and the organic crystal melt 510 may crystallize within crucible 520 to form an organic solid crystal.

In the embodiments of FIG. 4 and FIG. 5, the atmosphere overlying the melt phase may be controlled. For instance, the atmosphere overlying the melt may contain an inert gas such as argon that is maintained under a controlled pressure and/or flow rate.

Figure 6:
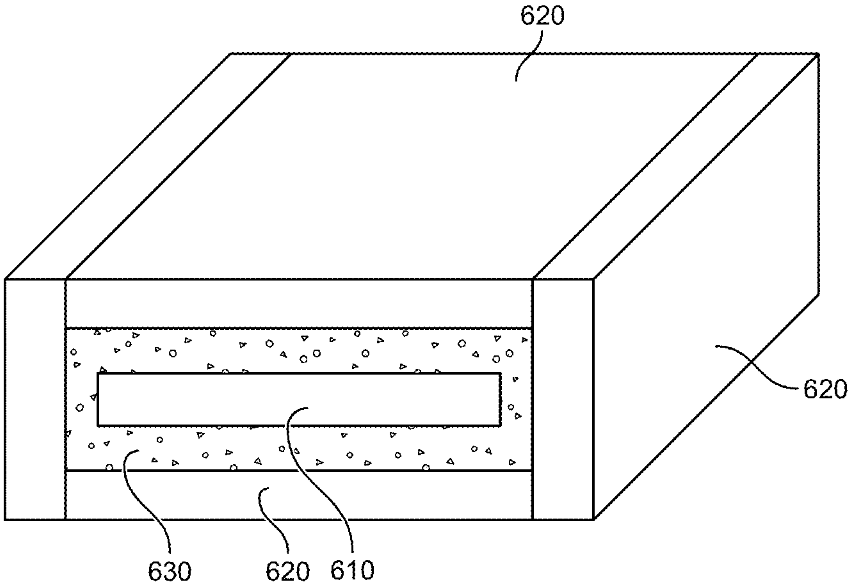
FIG. 6 shows (A) double-sided mold and (B) single-sided mold epitaxial growth processes for forming organic solid crystals according to further embodiments.
Figure 6:
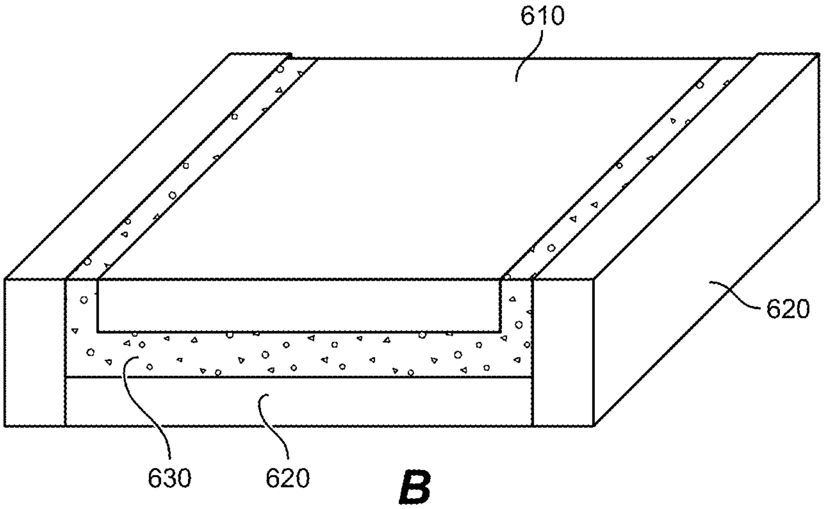
Figure 7:
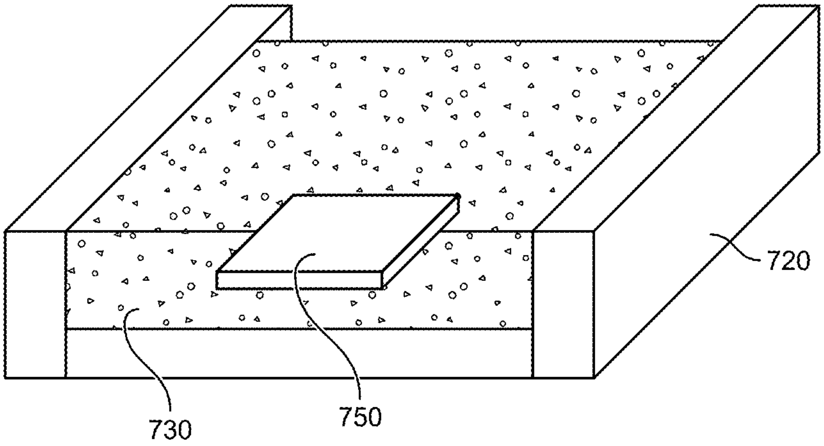
FIG. 7 shows a seeded single-sided mold epitaxial growth process for forming organic solid crystals according to some embodiments.
Figure 7:
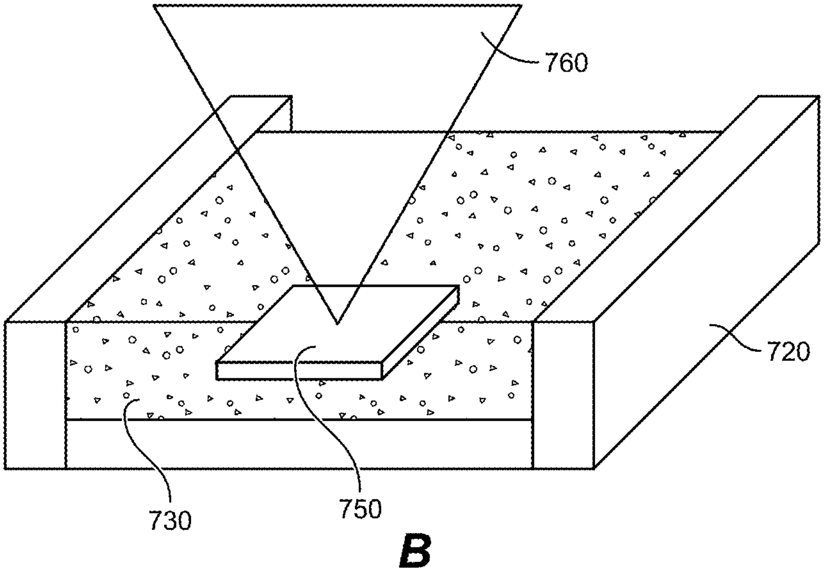

According to further embodiments, an example molding process architecture for forming an organic solid crystal is shown in FIG. 6, where both (A) a double-sided mold, and (B) a single-sided mold architecture are illustrated. In each approach, a layer of a non-volatile medium material (i.e., anti-nucleation layer) 630 may be disposed between a mold 620 and a melt phase 610. A localized seed layer (not shown) may be used to initiate crystal nucleation and growth. A cut-away illustration of the single-sided mold approach of FIG. 6B is shown in FIG. 7. In FIG. 7A, shown is a seed crystal 750 located within mold 720 and in contact with an anti-nucleation layer 730. Referring to FIG. 7B, a dispensing element 760 may be configured to deliver organic crystal molecules to a nucleation site proximate to the seed crystal 750, and subsequently to a crystallization front during crystal growth.

Figure 8:
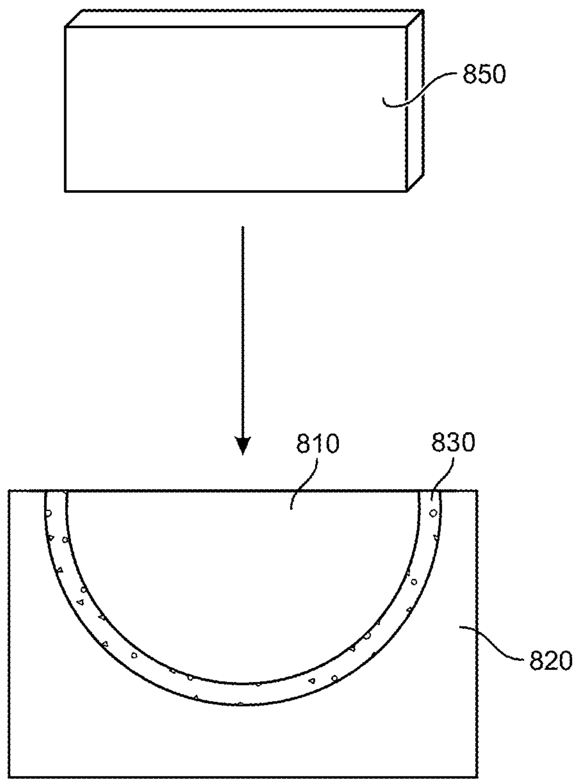
FIG. 8 is a schematic illustration of a solvent-based epitaxial/non-epitaxial growth process for forming organic solid crystals according to some embodiments.

Referring to FIG. 8, shown is a schematic set-up for an epitaxial or non-epitaxial growth process where an organic crystal seed 850 may be brought into contact with, and optionally drawn from, a super saturated organic solution 810. The organic solution may include one or more crystallizable organic molecules dissolved in a suitable solvent. The organic solution 810 may be contained within crucible 820 and separated from the crucible 820 by an anti-nucleation layer 830. By contacting the seed 850 with the solution 810, an organic solid crystal layer may nucleate and grow within crucible 820.

Figure 9:
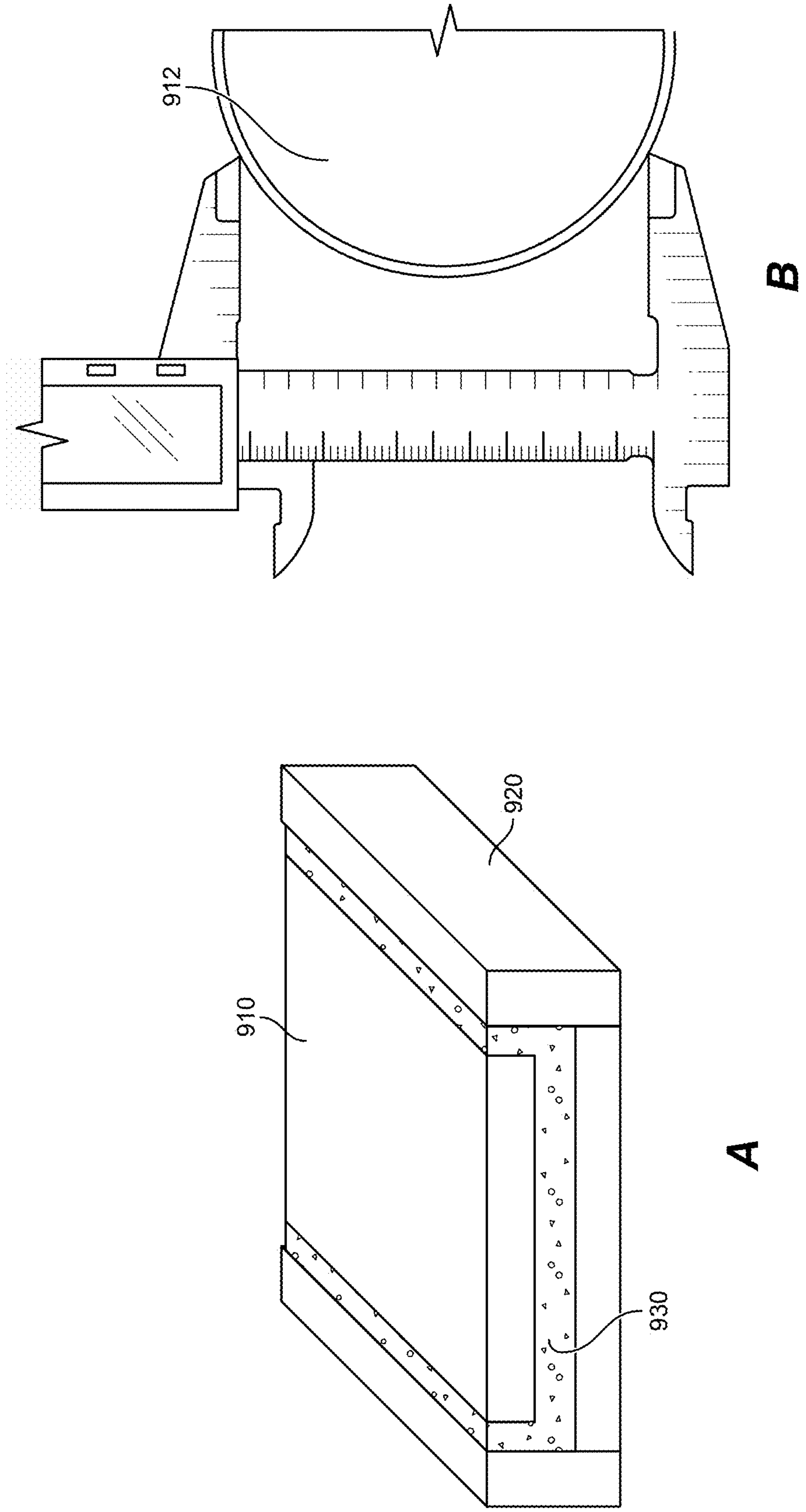
FIG. 9 is a schematic illustration of a non-epitaxial growth process for forming organic solid crystals according to certain embodiments.

Referring to FIG. 9, a further nucleation and growth process may include providing an anti-nucleation layer 930 over a substrate 920 and introducing an organic crystal solution 910 over the anti-nucleation layer 930. As shown in FIG. 9A, optionally in the absence of a seed layer, the organic crystal solution 910 may solidify to form an organic solid crystal. A photomicrograph of a free-standing organic solid crystal 912 is shown in FIG. 9B. According to some embodiments, the organic solid crystal 912 may be characterized by a length dimension of at least approximately 1 cm.

Figure 10:
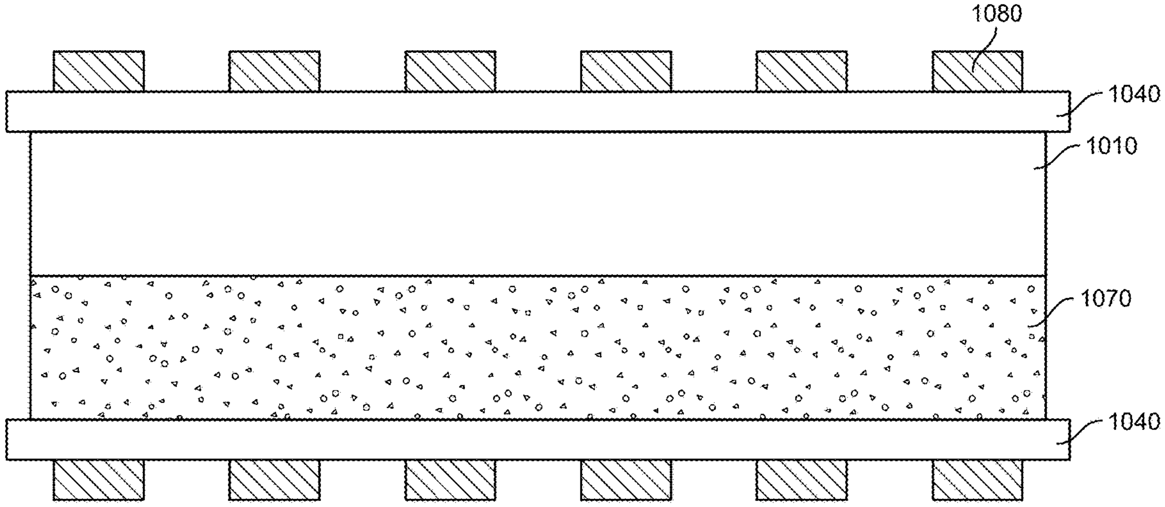
FIG. 10 illustrates an example organic solid crystal-containing grating architecture according to some embodiments.
Figure 10:
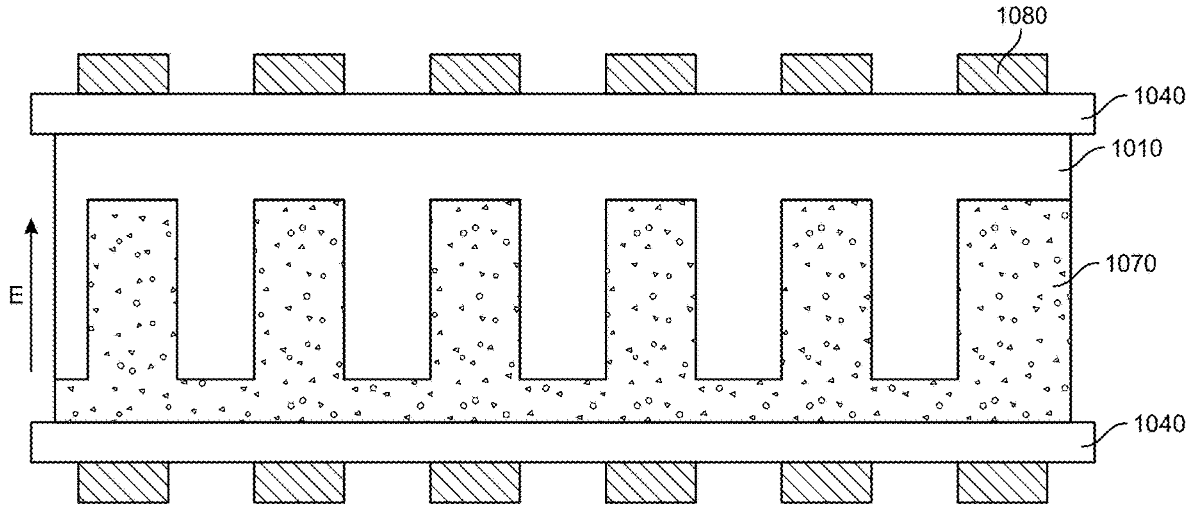
Figure 11:
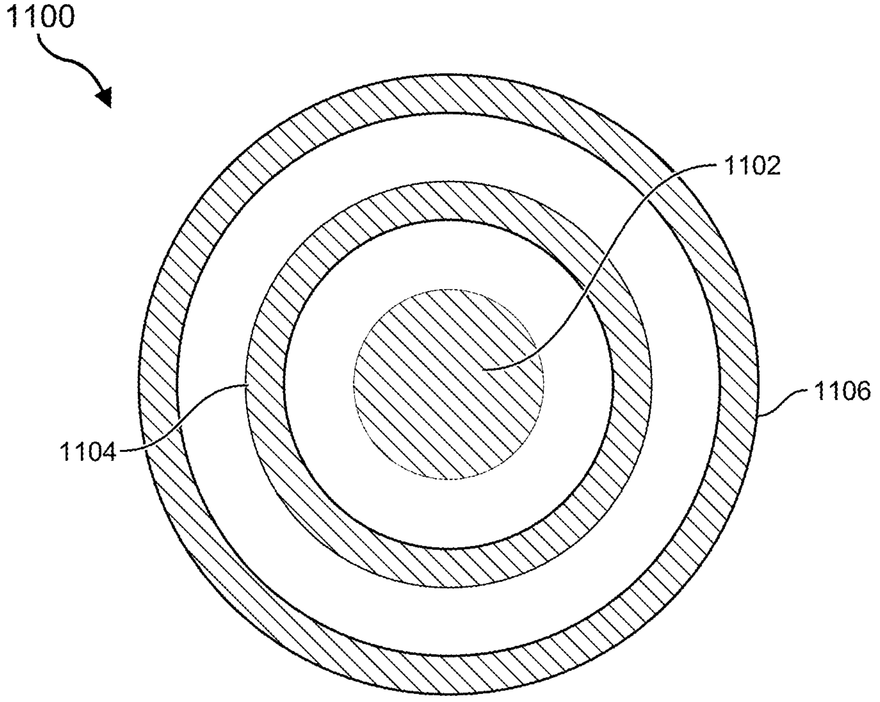
FIG. 11 illustrates an example tripolar concentric ring electrode (CRE) according to certain embodiments.

According to further embodiments, dynamic and static methods for forming an organic solid crystal having structured surface features are shown schematically in FIGS. 10 and 11. Referring initially to FIG. 10A, a layer of an organic crystal solution or melt 1010 and an adjacent layer of an electrically conductive liquid 1070 may be disposed between opposing substrates 1040. Patterned and paired electrodes 1080 may overlie the respective substrates 1040. Referring to FIG. 1013, under an applied electric field (E), a pattern may be induced in the electrically conductive liquid layer 1070, which may create a reciprocal pattern in the organic crystal material layer 1010. In turn, crystallization of the organic crystal material layer 1010 may be carried out by thermally-induced nucleation and growth, for example, optionally in conjunction with a seed crystal (not shown) to form an organic solid crystal thin film having periodic surface features or structures, such as an array of raised elements.

FIG. 11 illustrates an example structure of a tripolar concentric ring electrode (CRE) 1100, such as electrodes 1080. The CRE 1100 may include multiple electrode segments, such as a central disc 1102, an inner ring 1104, and an outer ring 1106. The electrodes may include metals such as aluminum, gold, silver, tin, copper, indium, gallium, zinc, and the like. Other conductive materials may be used, including carbon nanotubes, graphene, transparent conductive oxides (TCOs, e.g., indium tin oxide (ITO), indium gallium zinc oxide (IGZO), zinc oxide (ZnO), etc.), and the like.

The electrodes may be fabricated using any suitable process. For example, the electrodes may be fabricated using physical vapor deposition (PVD), chemical vapor deposition (CVD), evaporation, spray-coating, spin-coating, atomic layer deposition (ALD), and the like. In further aspects, the electrodes may be manufactured using a thermal evaporator, a sputtering system, a spray coater, a spin-coater, printing, stamping, etc.

The electrodes may have a thickness of approximately 1 nm to approximately 1000 nm, with an example thickness of approximately 10 nm to approximately 50 nm. The electrodes in certain embodiments may have an optical transmissivity of at least approximately 50%, e.g., approximately 50%, approximately 60%, approximately 70%, approximately 80%, approximately 90%, approximately 95%, approximately 97%, approximately 98%, or approximately 99%, including ranges between any of the foregoing values.

Figure 12:
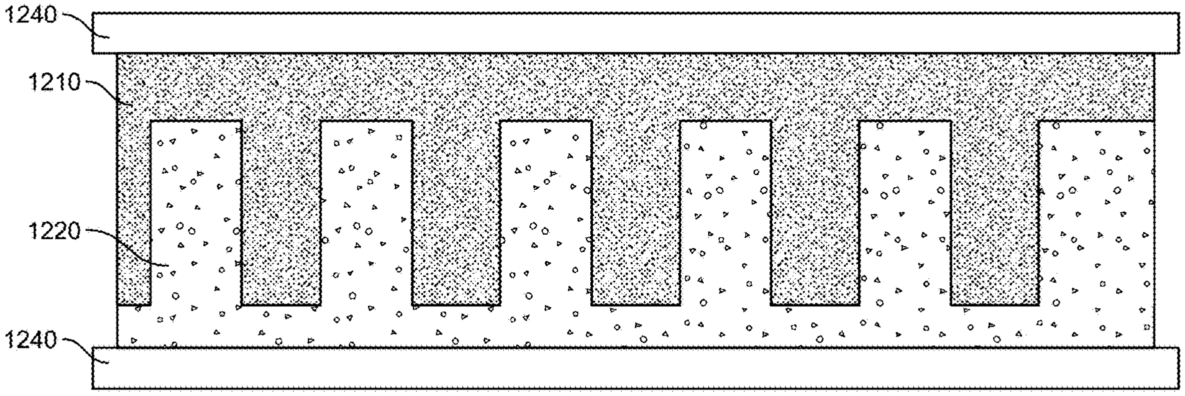
FIG. 12 illustrates an example organic solid crystal-containing grating architecture according to further embodiments.

Referring to FIG. 12, shown is a static approach to forming an organic solid crystal having structured surface features. A layer of an organic crystal solution or melt 1210 and an adjacent pre-patterned mold 1220 may be disposed between opposing substrates 1240. With the organic crystal solution or melt 1210 conforming to the shape of the patterned mold 1220, crystallization of the organic crystal material layer 1210 may be carried out by thermally-induced nucleation and growth to form an organic solid crystal thin film having periodic surface features. Such structured organic solid crystal thin films may form or be incorporated into a variety of optical elements, including gratings, micro lenses, prismatic lenses, Fresnel lenses, and the like.

Figure 13:
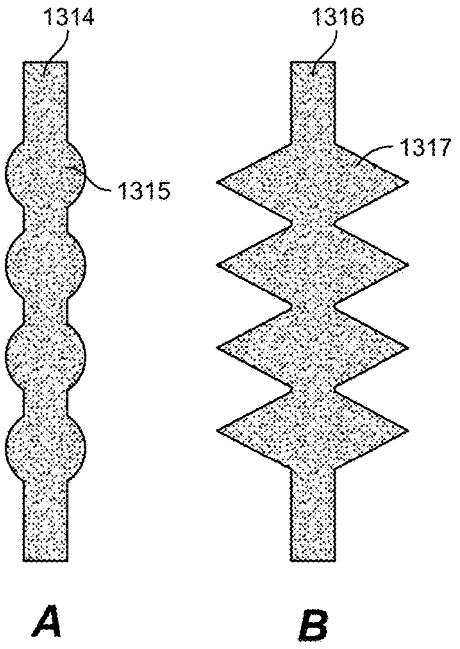
FIG. 13 illustrates example non-planar organic solid crystal geometries according to some embodiments.
Figure 14:
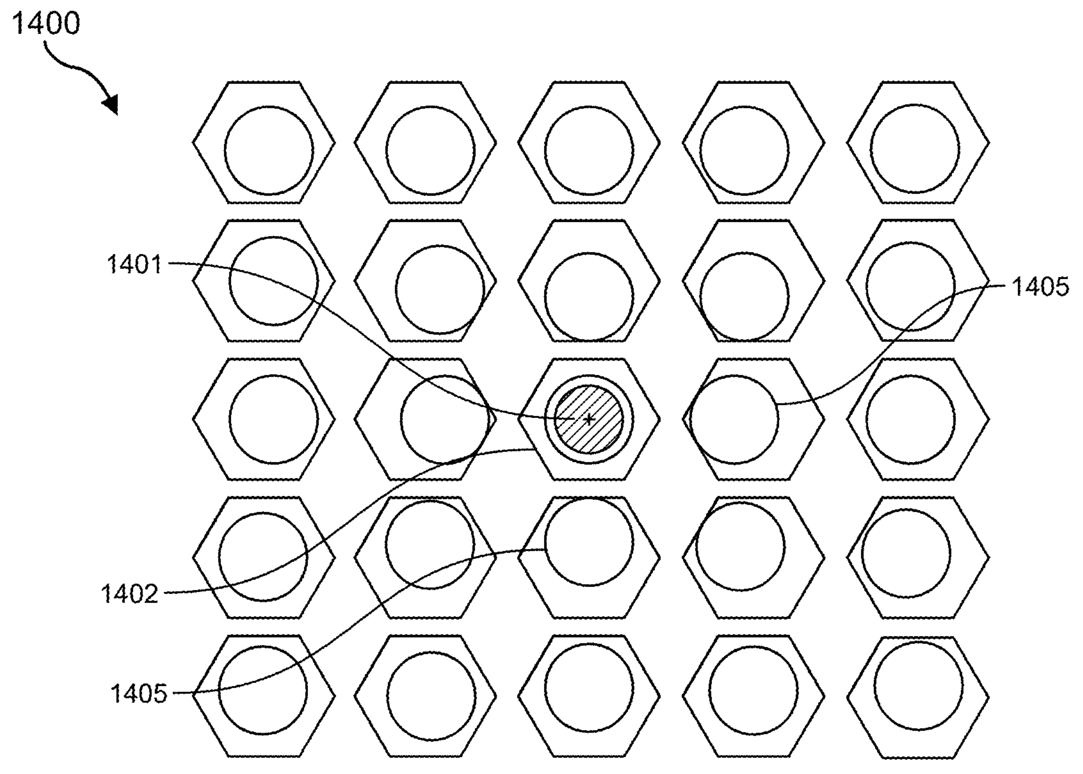
FIG. 14 illustrates an example mechanism for the active tuning of refractive index in a biased organic solid crystal according to some embodiments.

According to further embodiments, a schematic view of example organic solid crystal structures formed by drawing from a melt phase are shown in FIG. 13. The organic solid crystal 1314 depicted in FIG. 13A and the organic solid crystal 1316 depicted in FIG. 13B may include respective surface features, such as nodules 1315 or facets 1317, for example. One or more process variables, including draw rate from the melt, pressure, and temperature may be controlled to create a desired surface pattern.

Without wishing to be bound by theory, a source of active refractive index modulation in organic solid crystals may be derived from a change in polarizability of molecules that contain charge due to hole or electron injection. In organic molecules, the time it takes for a molecule to repolarize upon charge injection may be an order of magnitude faster than the residence time of the charge. Thus, as depicted schematically in FIG. 14, within an organic solid crystal material 1400 the charge 1401 may be on a molecule 1402 long enough for the molecule to modulate its electron cloud as well as the electron cloud 1405 of neighboring molecules. This change in the local electronics of the crystal may result in changes to the polarizability and the refractive index.

Figure 15:
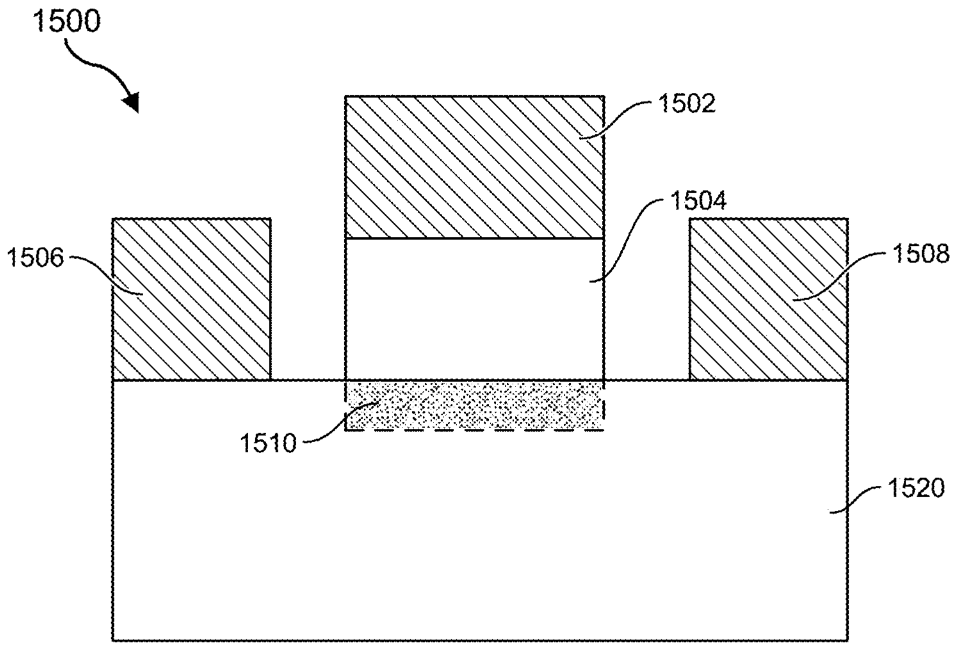
FIG. 15 shows the integration of an optically isotropic or anisotropic organic solid crystal layer into an example optical element according to various embodiments.

Referring to FIG. 15, an example optical element 1500 has a top gate-top contact (TGTC) architecture and includes a patterned gate 1502 disposed over an insulator layer 1504 and between source 1506 and drain 1508 contacts. The insulator layer 1504 may include any suitable dielectric material, including organic compounds (e.g., polymers) and inorganic compounds (e.g., silicon dioxide). The gate 1502 is disposed over an optically isotropic or anisotropic organic solid crystal (OSC) layer 1510. The gate 1502, source 1506, and drain 1508 are supported by a substrate 1520.

During operation, charge injection into the optically isotropic or anisotropic organic solid crystal (OSC) layer 1510 may be made through source (S) and drain (D) contacts. The illustrated optical element may form an active grating where the voltage applied to the gate and/or to the source and drain may be used to locally control the geometry (e.g., depth and orientation) of a portion of the OSC layer underlying the gate and therefore impact its interaction with light. According to further embodiments, the optical element of FIG. 15 may be applicable to photonic data storage.

According to some embodiments, the optical element of FIG. 15 may optionally include a charge transport layer (not shown) located between the source and the OSC layer and/or between the drain and the OSC layer. A charge transport layer may include an organic compound (e.g., carbon nanotubes) or an inorganic compound. In further example embodiments, an optical element may include a waveguide.

Figure 16:
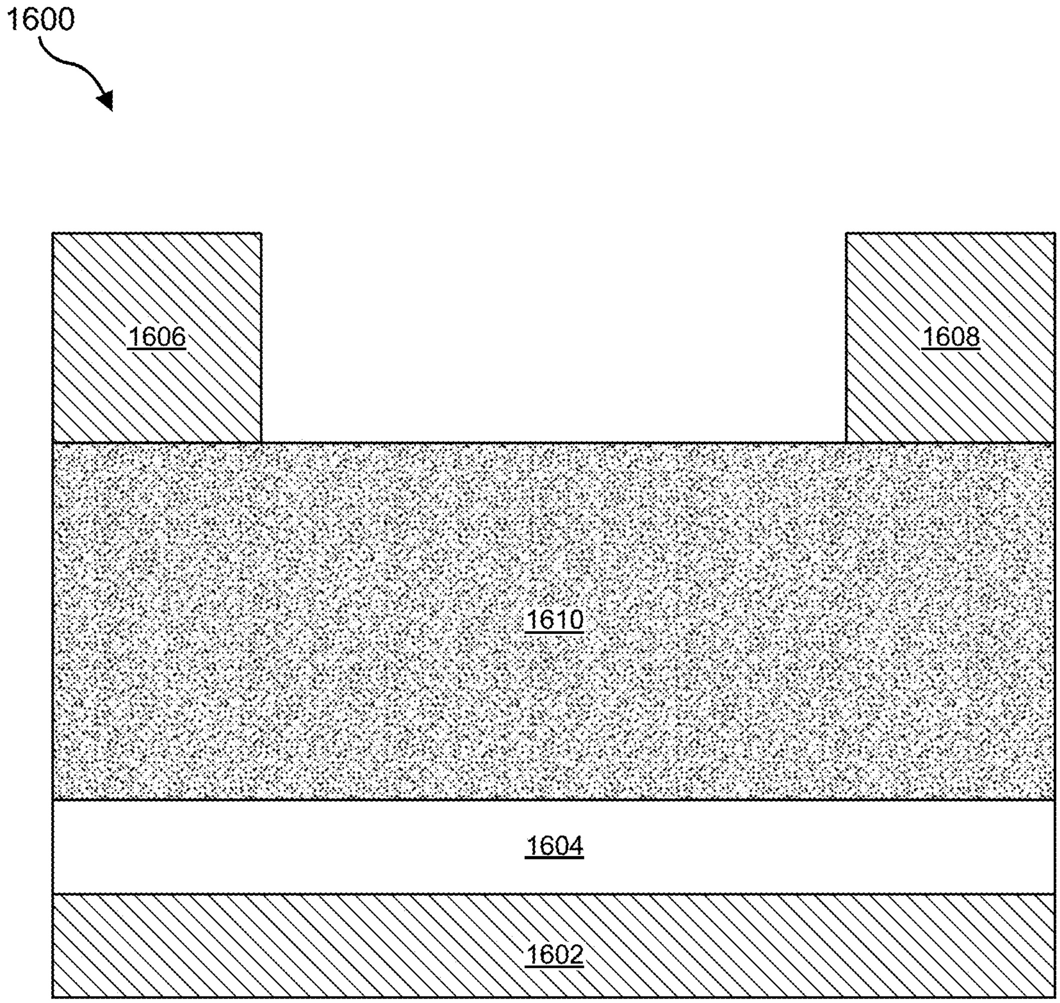
FIG. 16 shows the integration of an optically isotropic or anisotropic organic solid crystal thin film into an example optical element according to further embodiments.

Referring to FIG. 16, an example optical element 1600 has a bottom gate-top contact (BGTC) architecture and includes a gate 1602 disposed beneath an optically isotropic or anisotropic organic solid crystal (OSC) layer 1610. An insulator layer 1604 is disposed between the gate 1602 and the OSC layer 1610. The insulator layer 1604 may include any suitable dielectric material, including organic compounds (e.g., polymers) and inorganic compounds (e.g., silicon dioxide). Source 1606 and drain 1608 contacts directly overlie respective portions of the OSC layer 160 opposite to the gate 1602.

During operation, charge injection into the optically isotropic or anisotropic organic solid crystal (OSC) layer 1610 may be made through the source and drain contacts. The illustrated optical element may form an active grating where the voltage applied to the gate and/or to the source and drain may be used to locally control the geometry (e.g., depth and orientation) of a portion of the OSC layer overlying the gate and therefore impact its interaction with light.

Figure 17:
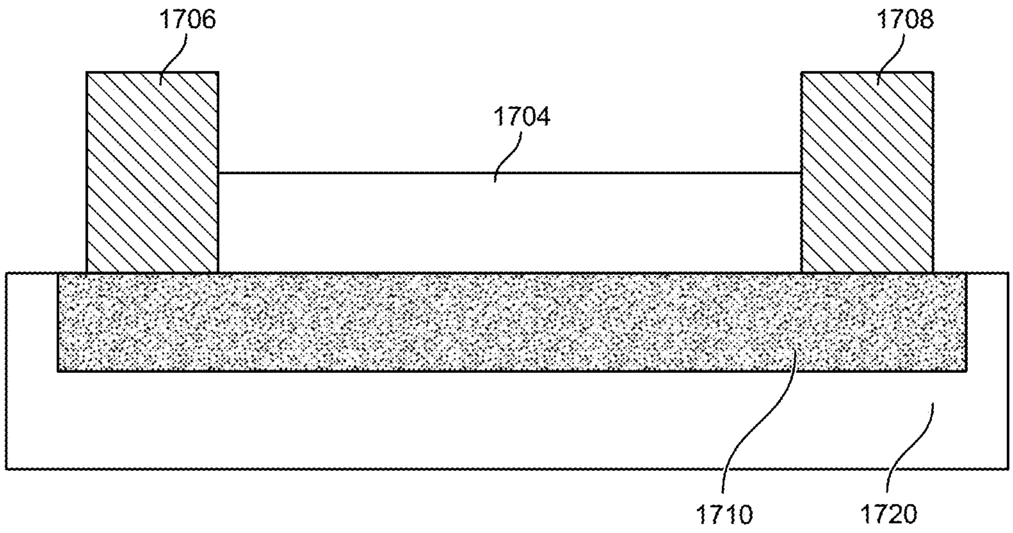
FIG. 17 illustrates an optical modulator having a pair of electrodes disposed over a common side of an organic solid crystal (OSC) layer according to some embodiments.

A cross-sectional schematic view of an optical modulator according to some embodiments is shown in FIG. 17. The modulator structure may include a substrate 1720 defining a well and an OSC layer 1710 disposed within the well. A pair of electrodes 1706, 1708 may directly overlie respective portions of the OSC layer 1710. The electrodes 1706, 1708 may be spaced away from each other and a dielectric layer 1704 may overlie the OSC layer 1710 between the electrodes 1706, 1708.

Figure 18:
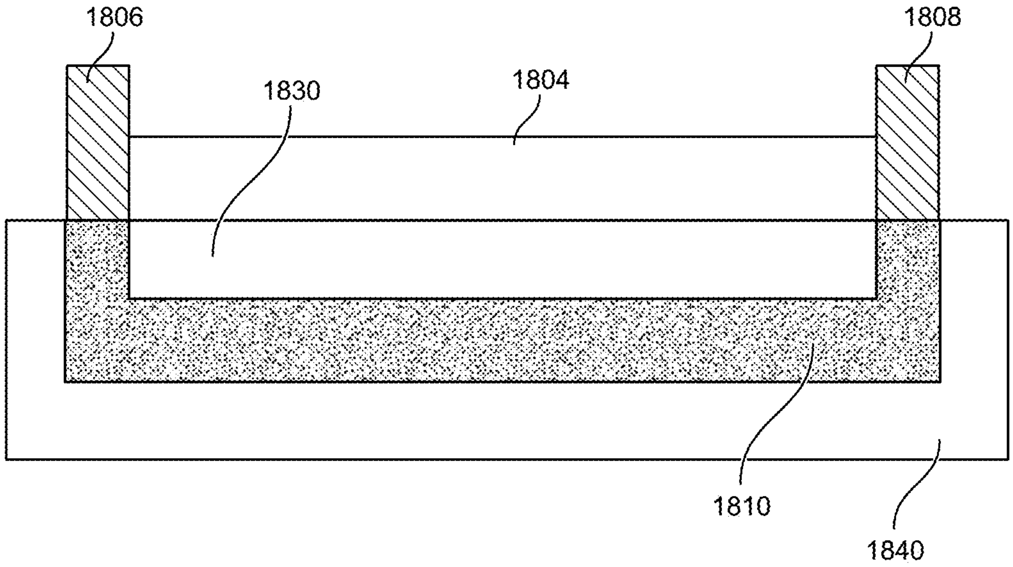
FIG. 18 illustrates an optical modulator having a pair of electrodes disposed over a common side of an organic solid crystal (OSC) layer according to further embodiments.

Referring now to FIG. 18, shown is a cross-sectional schematic view of an optical modulator according to further embodiments. The modulator structure may include an OSC layer 1810 sandwiched between top and bottom semiconductor layers 1830 and 1840, respectively. Bottom semiconductor layer 1840 may define a well with both the OSC layer 1810 and the top semiconductor layer 1830 located within the well. A pair of electrodes 1806, 1808 may directly overlie respective portions of the OSC layer 1810. The electrodes 1806, 1808 may be spaced away from each other and a dielectric layer 1804 may overlie the top semiconductor layer 1830 between the electrodes 1806, 1808.

Figure 19:
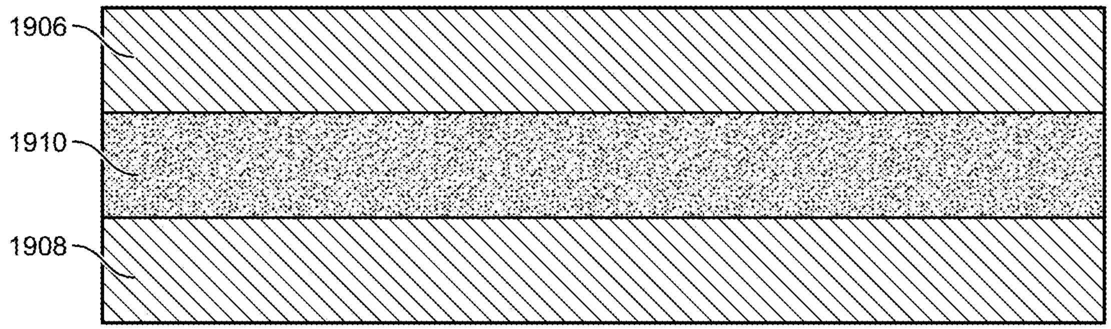
FIG. 19 illustrates an optical modulator having an organic solid crystal (OSC) layer disposed between conductive electrodes according to some embodiments.
Figure 20:
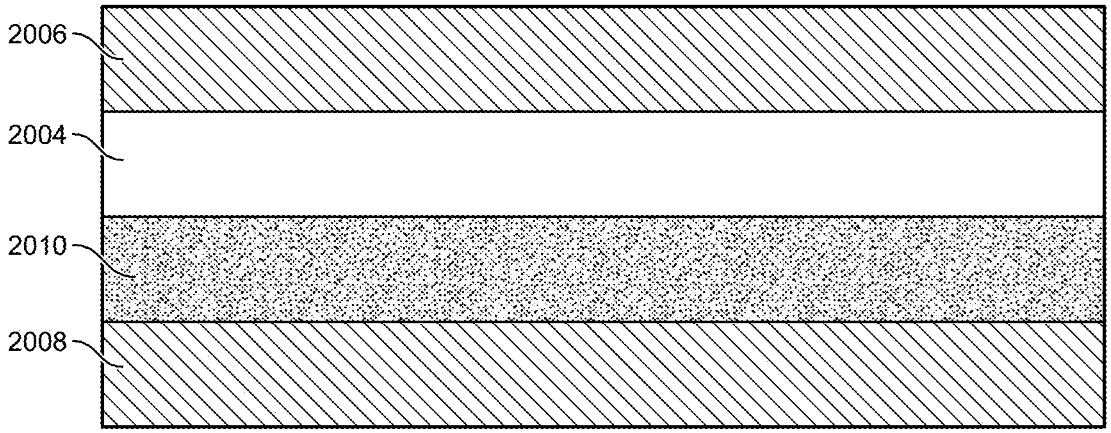
FIG. 20 illustrates an optical modulator having an organic solid crystal (OSC) layer and a dielectric layer disposed between conductive electrodes according to further embodiments.
Figure 21:
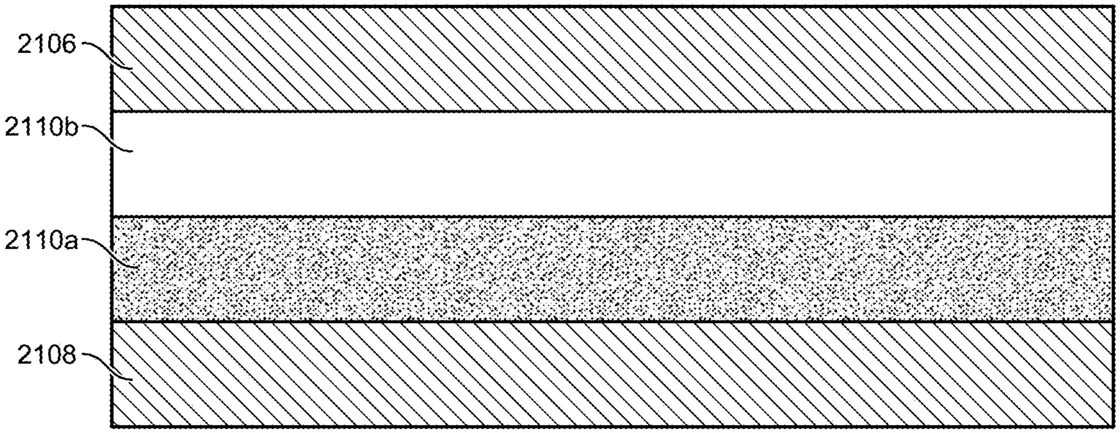
FIG. 21 illustrates an optical modulator having an organic solid crystal (OSC) layer and a semiconductor layer disposed between conductive electrodes according to still further embodiments.

Referring to FIG. 19, a further example optical modulator may include a layer of an organic solid crystal 1910 sandwiched between a pair of electrodes 1906, 1908. Referring to FIG. 20, in some embodiments, a dielectric layer 2004 may be disposed between the OSC layer 2010 and one or more of the electrodes 2006, 2008. During operation, the dielectric layer 2004 may be configured to mediate the current or voltage applied to the OSC layer 2010. A still further optical modulator is shown in FIG. 21. In the embodiment of FIG. 21, a bilayer including a semiconductor layer 2110*b* directly overlying an OSC layer 2110*a* is sandwiched between a pair of electrodes 2106, 2108.

Figure 22:
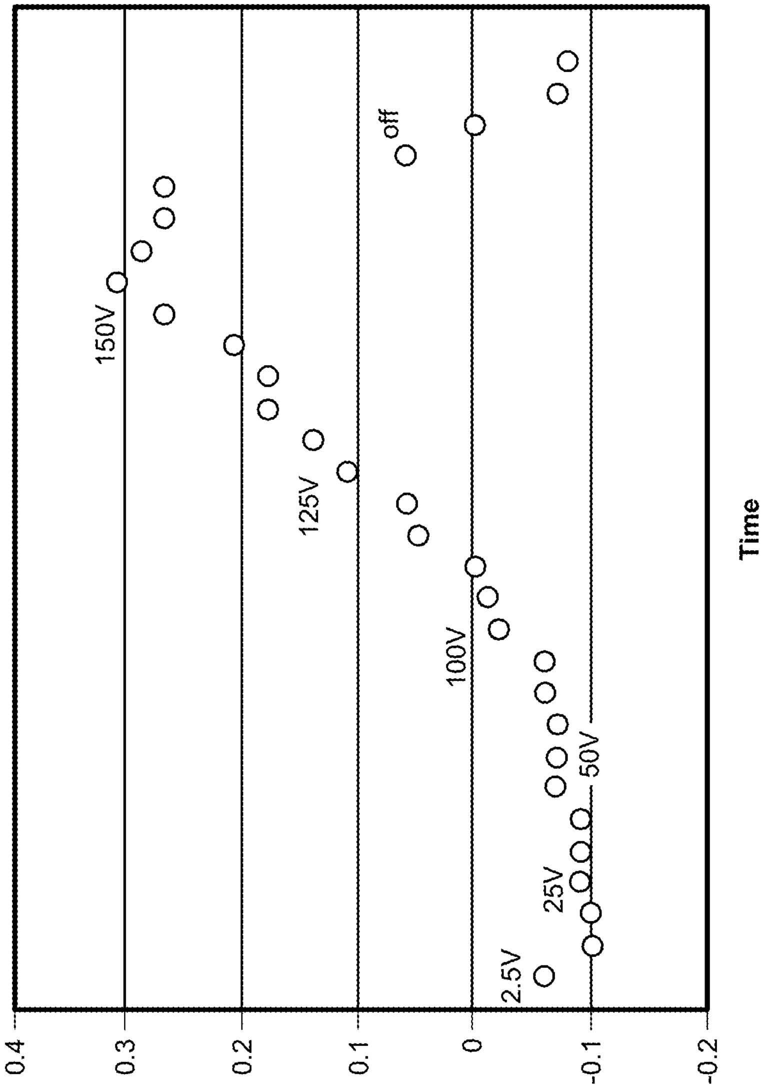
FIG. 22 is a plot of an ellipsometric peak shift versus time for an example OSC-containing optical modulator showing the impact of applied voltage according to some embodiments.
Figure 22:
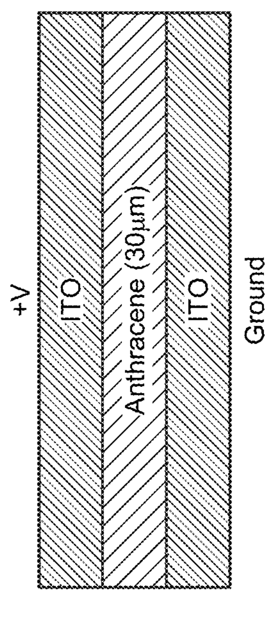

The structure and performance of an example OSC-containing optical modulator is shown in FIG. 22. Referring initially to FIG. 22A, the optical modulator includes a layer of anthracene disposed between a pair of indium tin oxide (ITO) electrodes. The anthracene layer may include a single crystal or may be polycrystalline, for example. Referring to FIG. 22B, shown is a plot of the shift of an arbitrary peak measured by ellipsometry as a function of time (applied voltage). The shift in the peak position is well-correlated to the applied voltage, including a well-defined decay corresponding to removal of the voltage.

Figure 23:
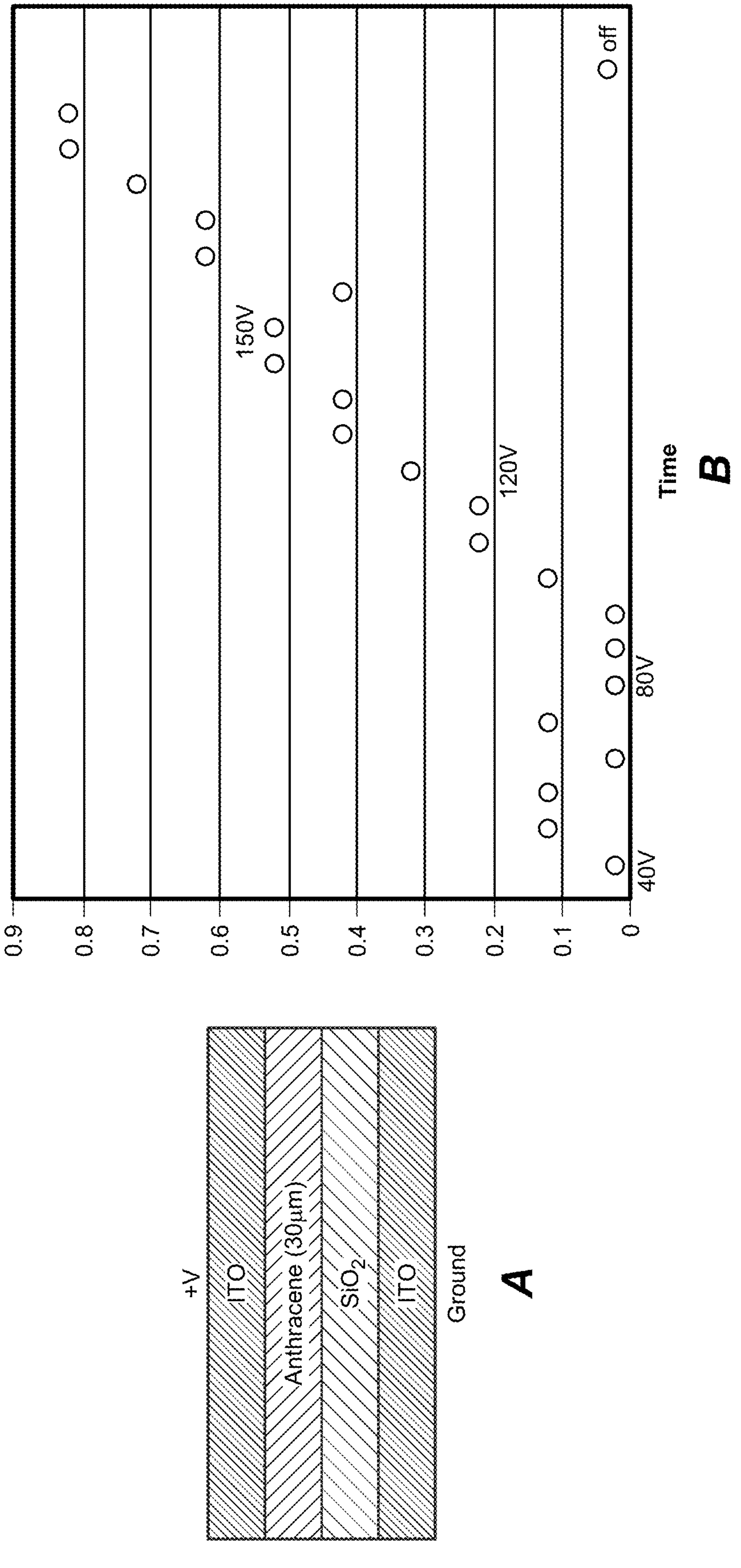
FIG. 23 is a plot of an ellipsometric peak shift versus time for an example OSC-containing optical modulator showing the impact of applied voltage according to some embodiments.

Referring to FIG. 23, a further example optical modulator includes a bilayer of anthracene and silicon dioxide disposed between a pair of indium tin oxide (ITO) electrodes. The structure is shown schematically in FIG. 23A. As shown in FIG. 23B, the shift in the peak position for an arbitrary peak measured by ellipsometry is well-correlated to the applied voltage, including a well-defined decay corresponding to removal of the voltage. In both FIG. 22 and FIG. 23, the peak shift may be correlated to a change in refractive index and/or birefringence for the OSC layer.

Figure 24:
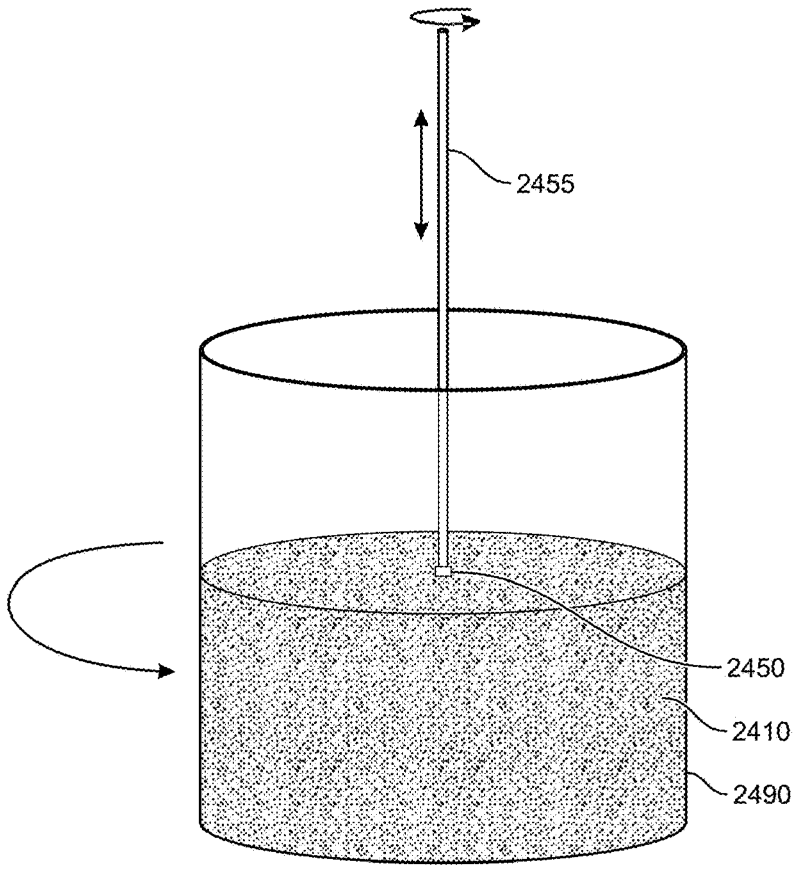
FIG. 24 is a schematic illustration of an example crystal growth apparatus for manufacturing an organic solid crystal according to various embodiments.

Referring to FIG. 24, shown is a perspective view of a further example melt-based deposition method and apparatus for forming an organic solid crystal from molten feedstock. Molten feedstock 2410 may be contained by reservoir 2490. Reservoir 2490 may be formed from a glass or glass ceramic composition, for example, and may include an internal passivation layer (not shown) to suppress nucleation. A seed crystal 2450 may be mounted at a distal end of a rotatable and translatable rod 2455, such that the seed crystal 2450 may be lowered into the molten feedstock 2410 and withdrawn therefrom. A control system (not shown) may be configured to control one or more of the melt temperature, seed temperature, gas pressure and gas composition overlying the melt, rotation rate of the molten feedstock, rotation rate and draw rate of the seed crystal, etc.

Figure 25:
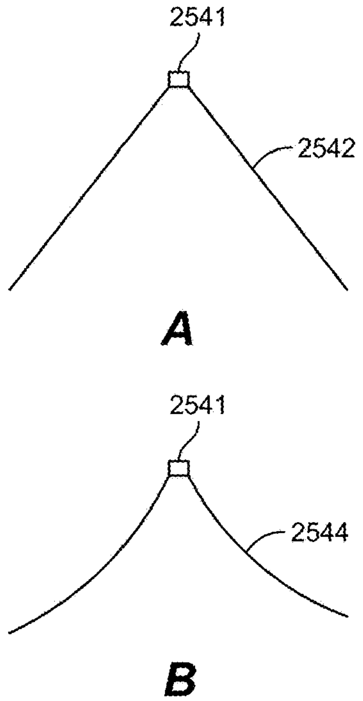
FIG. 25 is an illustration of example nucleation surface and scaffold geometries according to certain embodiments.

Turning to FIG. 25, according to various embodiments, located proximate to a seed crystal and a corresponding nucleation region, a crystal growth scaffold may be configured to template the growth of a desirably-shaped organic solid crystal. As shown in FIG. 25A, adjacent to nucleation region 2541, a planar scaffold 2542 may support the crystal growth of an organic solid crystal having a planar surface. As shown in FIG. 25B, adjacent to nucleation region 2541, a non-planar scaffold 2544 may support the crystal growth of an organic solid crystal having a concave or convex growth surface. In some embodiments, plural seed crystals and plural associated scaffolds may be arrayed to form multiple nucleation sites from which several nuclei may grow and merge into larger crystals.

Figure 26:
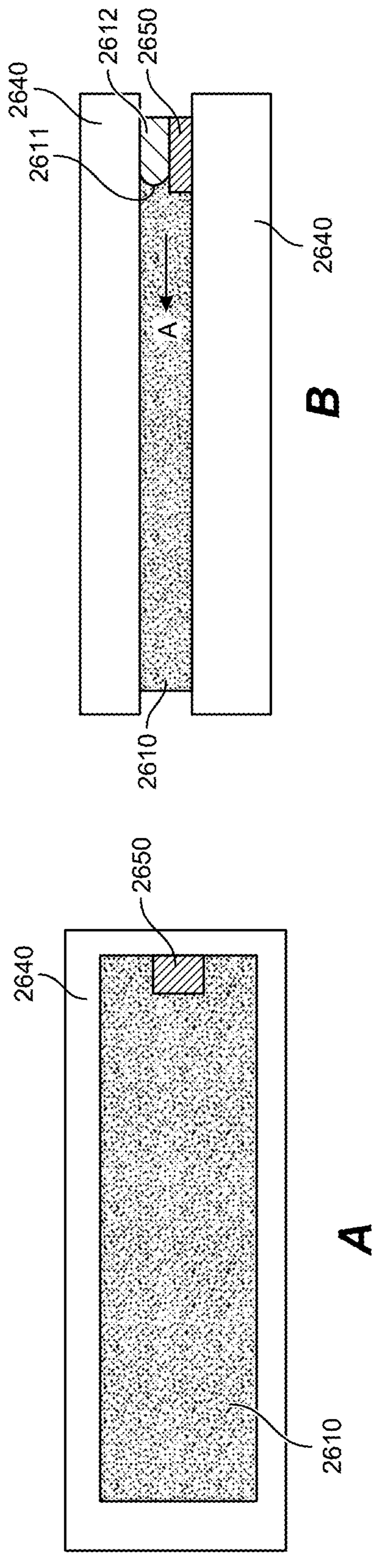
FIG. 26 is an illustration showing (A) a top down view and (B) a side view of an example crystal growth configuration having a single nucleation site for manufacturing an organic solid crystal (OSC) thin film according to some embodiments.
Figure 27:
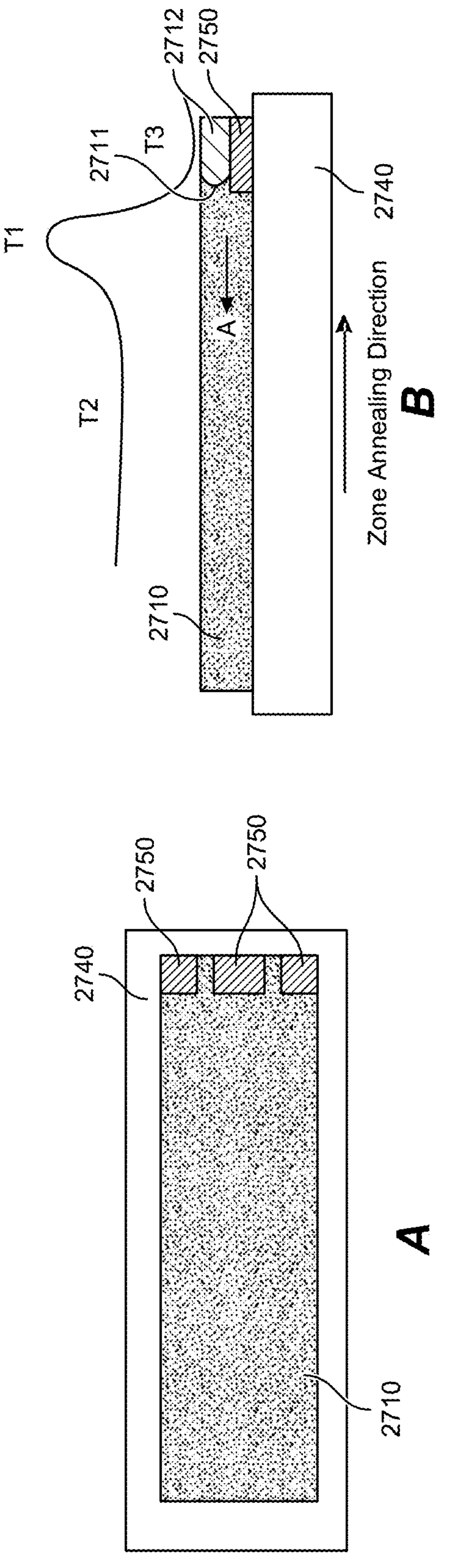
FIG. 27 is an illustration showing (A) a top down view and (B) a side view of an example crystal growth configuration having plural nucleation sites for manufacturing an organic solid crystal (OSC) thin film according to some embodiments.

Top down plan views and cross-sectional views of example manufacturing architectures and methods for forming organic solid crystal thin films according to further embodiments are shown in FIG. 26 and FIG. 27. FIGS. 26A and 15B relate to a thin film forming architecture having a substrate 2640 and a single seed crystal 2650 disposed over the substrate 2640, whereas FIGS. 27A and 27B relate to a thin film forming architecture having a substrate 2740 and plural seed layers 2750 disposed over the substrate 2740. A layer of a crystallizable organic precursor 2610, 2710 may be deposited over a respective substrate 2640, 2740 and over respective seed crystal(s) 2650, 2750.

An organic solid crystal thin film 2612, 2712 may be formed by zone annealing using a suitable temperature profile ($T_1$, $T_2$, $T_3$). An example thermal profile is shown in FIG. 27B, where an organic solid crystal layer 2712 may nucleate proximate to seed crystal 2750. The direction of movement of a crystallization front 2611, 2711 during crystal growth is denoted in FIGS. 26B and 27B with an arrow A.

Figure 28:
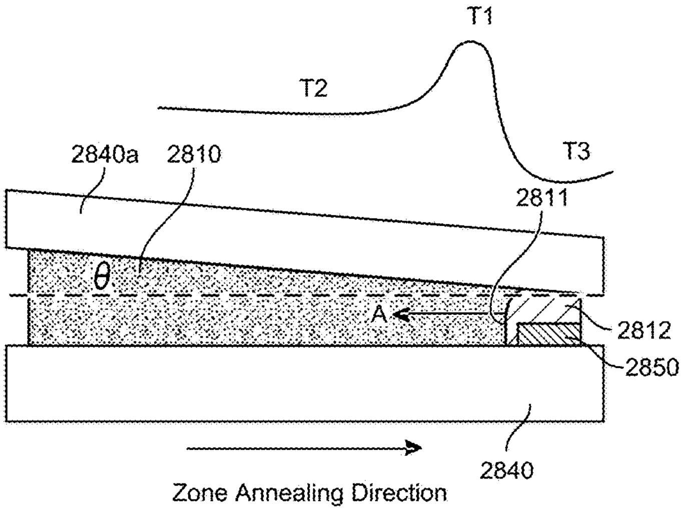
FIG. 28 is an illustration showing an OSC thin film manufacturing configuration for facilitating mass transport to a crystallization front during crystal growth according to some embodiments.
Figure 28:
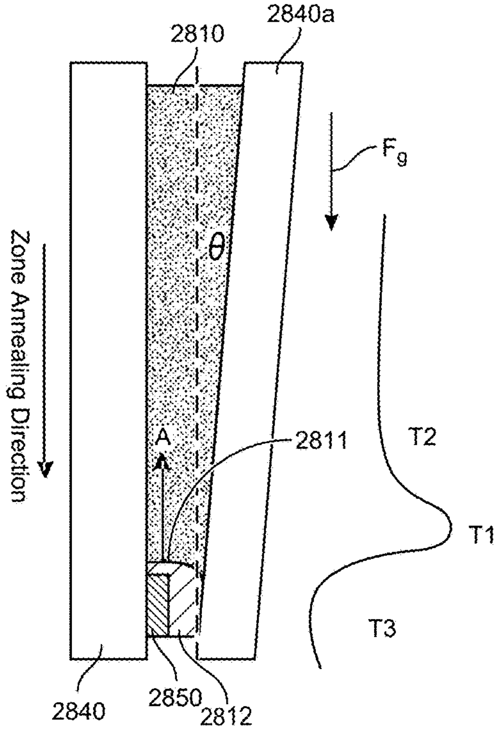

A further thin film forming architecture is shown in FIG. 28. Referring to FIG. 28A, a thin film forming architecture includes a substrate 2840 and a seed crystal 2850 disposed over a portion of the substrate 2840. A layer of a crystallizable organic precursor 2810 may be deposited over the substrate 2840 and over the seed crystal 2850. Application of a suitable thermal gradient ($T_1$, $T_2$, $T_3$) may induce nucleation and growth of an organic solid crystal thin film 2812. The thin film forming architecture may be translated relative to the thermal profile to advance a crystallization front 2811 and increase the area of the organic solid crystal thin film 2812 through crystal growth.

A cover plate 2840*a* may overlie the crystallizable organic precursor layer 2810. The cover plate 2840*a* may be inclined at an angle (θ) relative to the substrate 2840 and may be configured to generate capillary forces that improve mass transport of the molten feedstock to a region containing the crystallization front 2811. Referring to FIG. 28B, the apparatus of FIG. 28A may be oriented vertically. In the vertical orientation of FIG. 28B, in addition to or in lieu of capillary forces, gravitational forces ($F_g$) may advantageously promote mass transfer of the molten feedstock 2810 to the crystallization front 2811.

Figure 29:
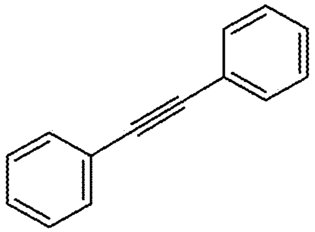
FIG. 29 shows example crystallizable organic molecules for manufacturing an organic solid crystal according to certain embodiments.
Figure 29:
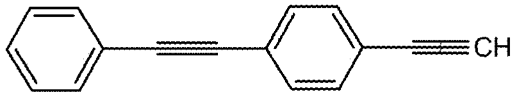
Figure 29:
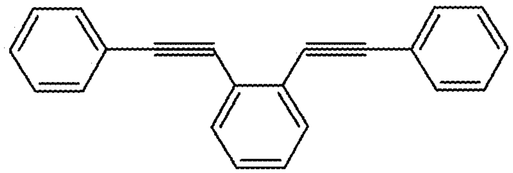
Figure 29:
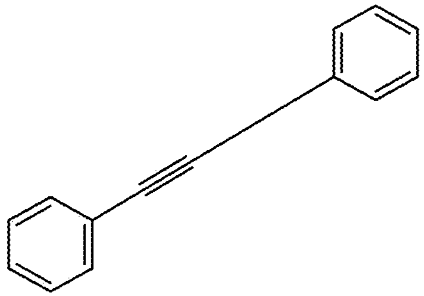
Figure 29:
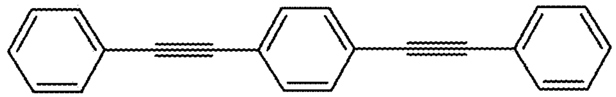
Figure 29:
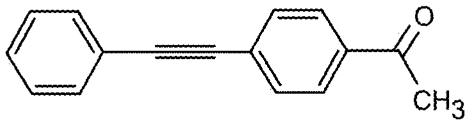
Figure 29:
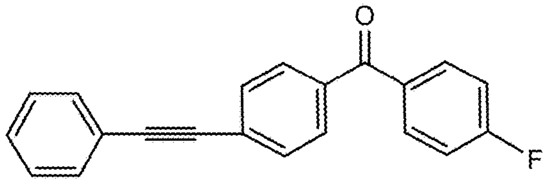
Figure 29:
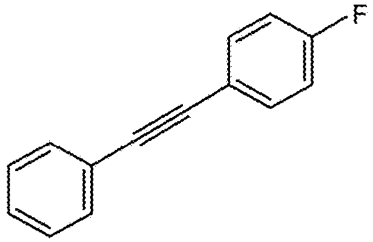
Figure 29:
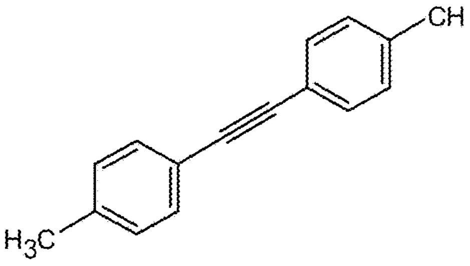
Figure 29:
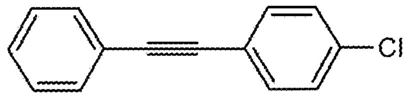
Figure 29:
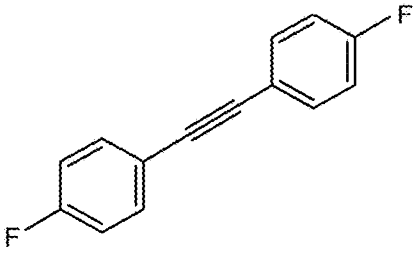
Figure 29:
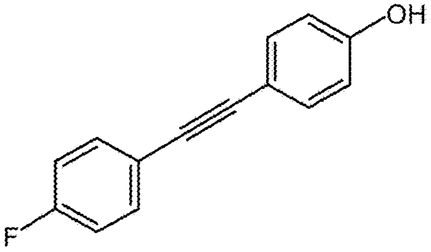
Figure 29:
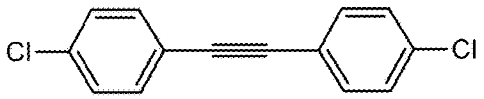
Figure 29:
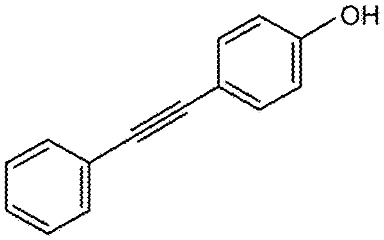
Figure 29:
Figure 29:
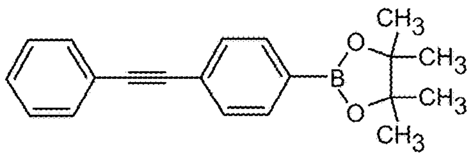
Figure 29:
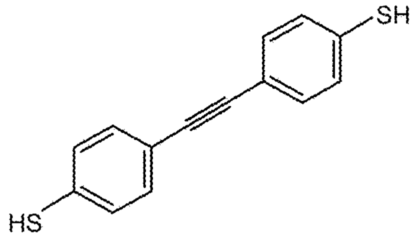
Figure 29:
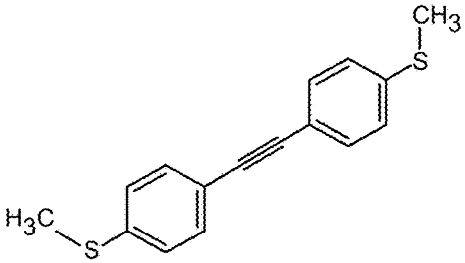
Figure 29:
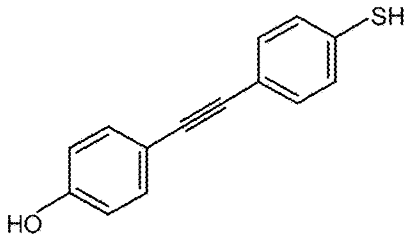
Figure 29:
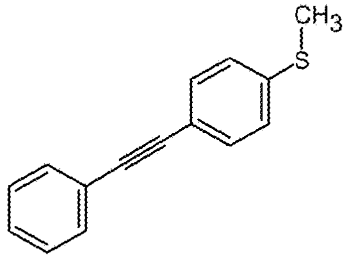
Figure 29:
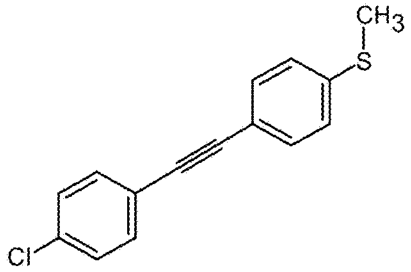
Figure 29:
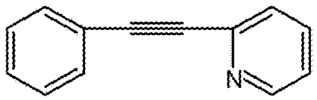
Figure 29:
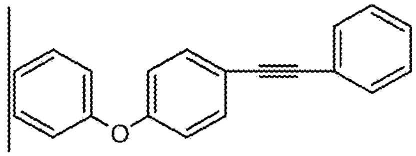
Figure 29:
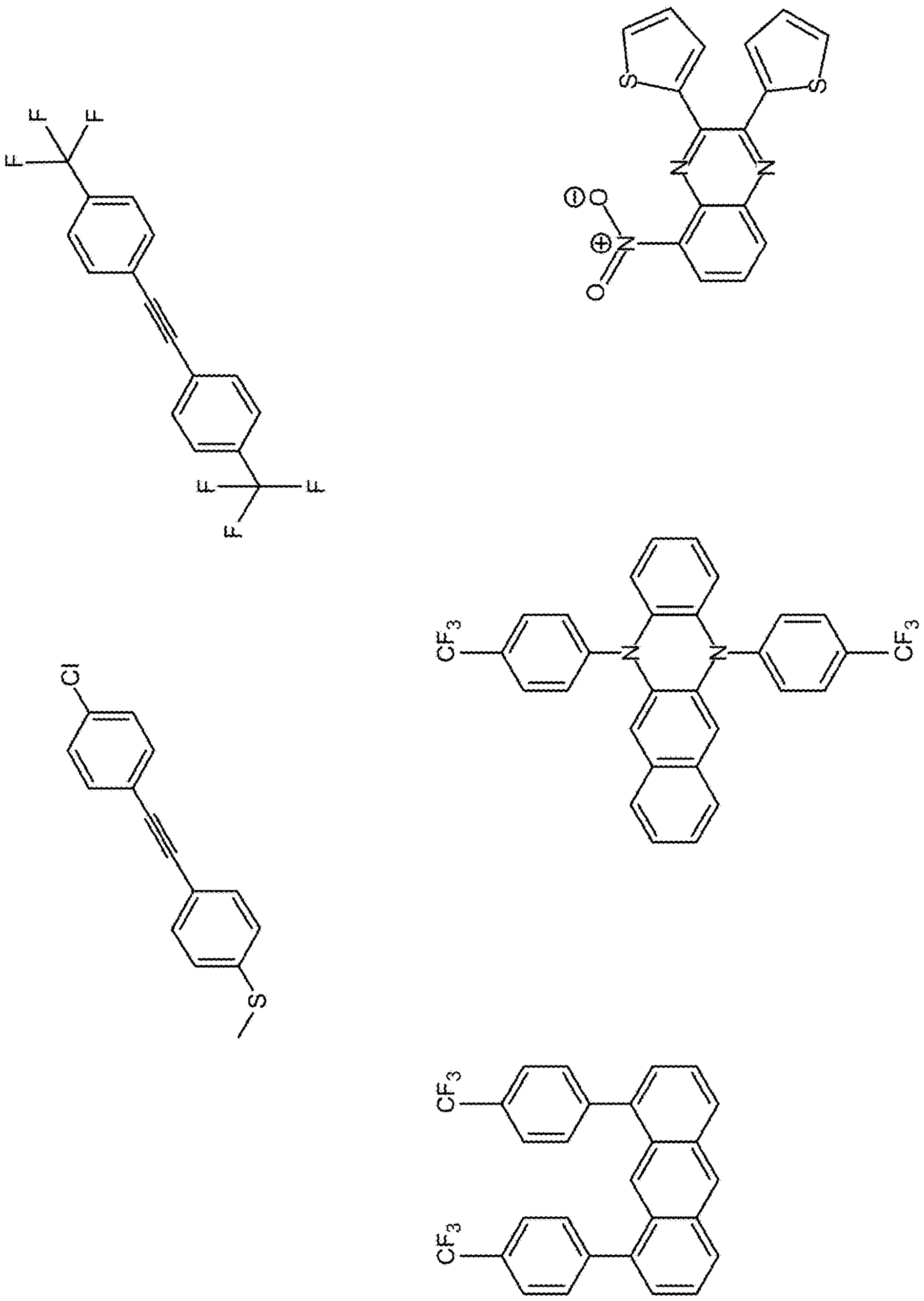
Figure 30:
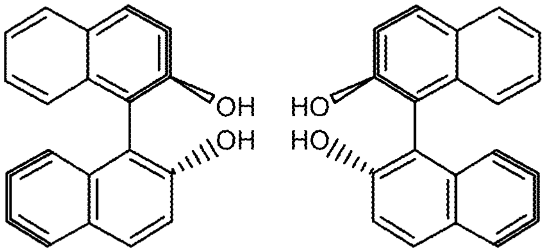
FIG. 30 is a schematic illustration of an exemplary chiral molecule for forming an organic solid crystal according to some embodiments.

Example OSC materials suitable for forming a feedstock composition include small molecules, macromolecules, liquid crystals, organometallic compounds, oligomers, and polymers, and may include organic semiconductors such as polycyclic aromatic compounds, e.g., anthracene, phenanthrene, and the like. Methods of manufacturing organic solid crystals may include crystal growth from a melt or solution, chemical or physical vapor deposition, and solvent coating onto a substrate. A deposition surface of the substrate may be treated globally or locally to impact, for example, nucleation density, crystalline orientation, adhesion, etc. The foregoing methods may be applied in conjunction with one or more optional post-deposition steps, such as annealing, polishing, dicing, etc., which may be carried out to improve one or more OSC attributes, including crystallinity, thickness, curvature, and the like. Example organic molecules that may be used to form an organic solid crystal are shown in FIG. 29. Referring to FIG. 30, illustrated is an example chiral molecule (1,1'-bi-2-naphthol). The compound 1,1'-bi-2-naphthol, also referred to as BINOL, has axial chirality and two readily separatable enantiomers.

Figure 31:
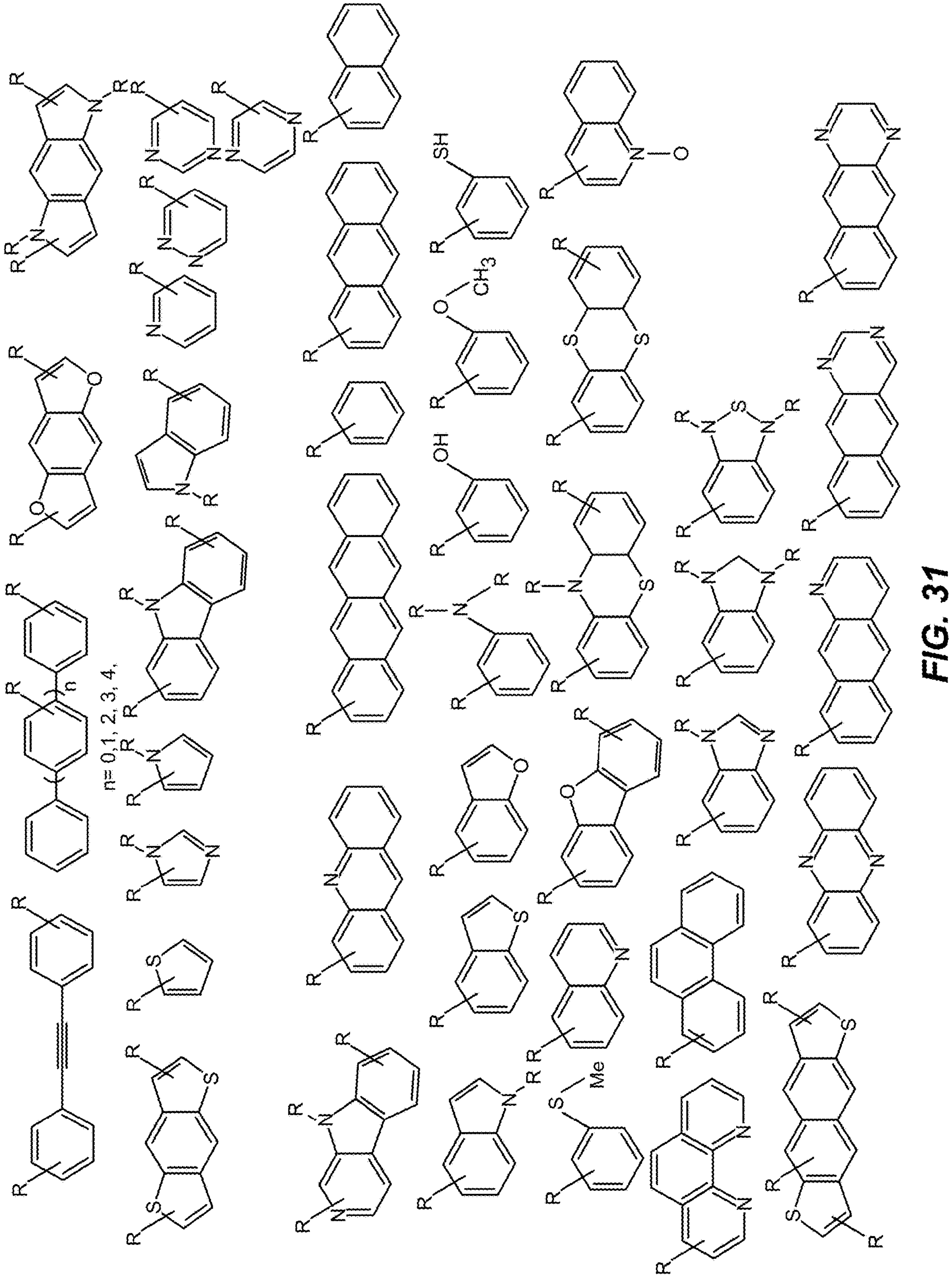
FIG. 31 shows example crystallizable organic molecules bonded to electron withdrawing groups according to certain embodiments.
Figure 31:
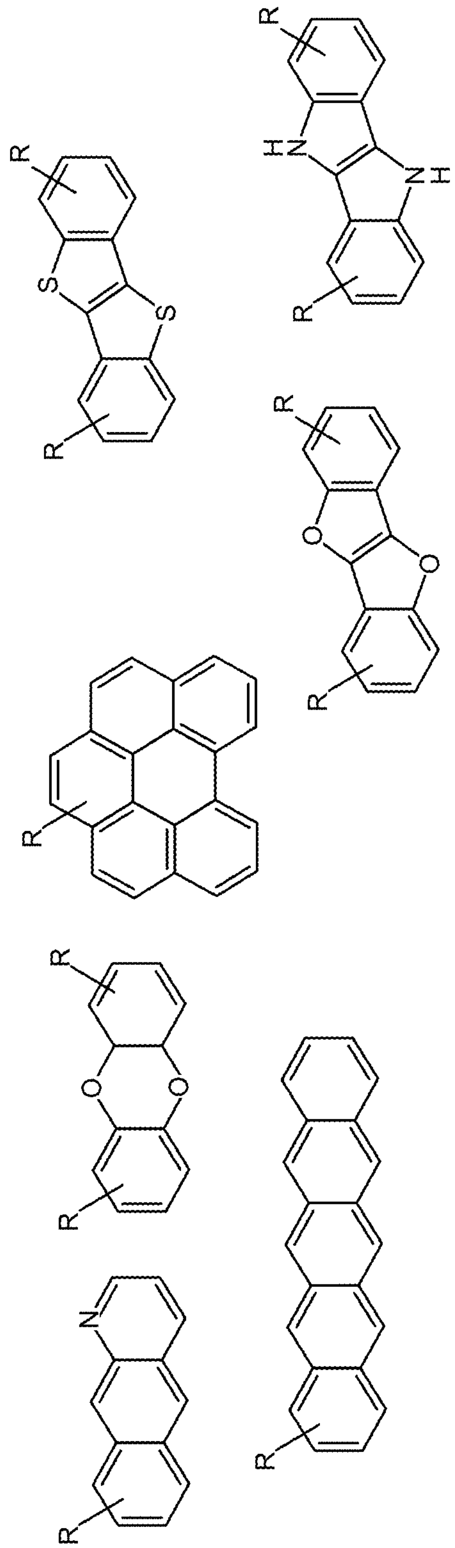

Turning to FIG. 31, shown are example embodiments of organic molecules bonded to electron withdrawing groups. The EWGs may reside at any position on the molecule and may include a single or combination of EWGs on a molecule. Example functional EWGs include fluorine, chlorine, bromine, iodine, phenylalanine, nitrogen dioxide, sulfur trioxide, mesylate, acetyl, carboxyl, aldehyde, and sulfur ammonia. According to various embodiments, EWGs may be configured to improve a packing density of the anisotropic organic molecule due to the intermolecular interactions and position of EWGs on the organic molecule.

Figure 32:
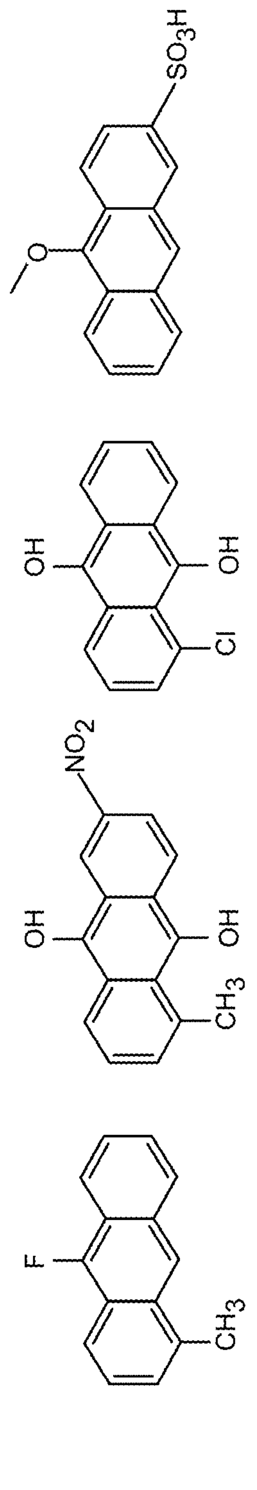
FIG. 32 shows example crystallizable organic molecules bonded to functional groups according to certain embodiments.

Referring to FIG. 32, shown are example embodiments of organic molecules bonded to functional groups at different areas of the molecule. Example functional groups may include methyl and hydroxyl groups. According to some embodiments, an organic molecule may include a single functional group or more than one functional group.

A molecule is designated chiral if it cannot be superposed on its mirror image by any combination of rotations, translations, and some conformational changes. According to various embodiments, a chiral molecule for forming an organic solid crystal may have a single stereogenic center, although chiral molecules having two or more chiral centers, e.g., diastereomers, are contemplated. According to some embodiments, an organic solid crystal may include just a single enantiomer of a chiral compound or a mixture of enantiomers, such as a racemic mixture.

Figure 33:
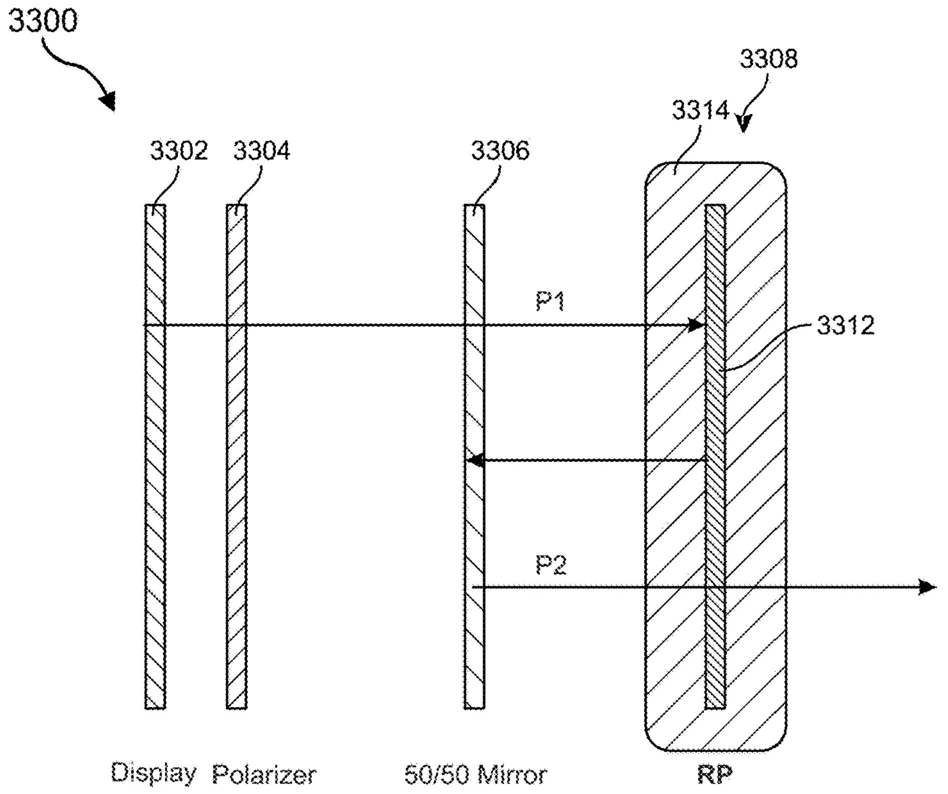
FIG. 33 is a cross-sectional schematic illustration of an optical element including a reflective organic solid crystal-containing polarizer according to some embodiments.

Referring to FIG. 33, shown is a cross-sectional view of an example optical element. Arranged in optical alignment, optical element 3300 may include a display 3302, a polarizer 3304, a 50/50 mirror 3306, and a circular reflective polarizer 3308. The circular reflective polarizer 3308 may include a multilayer organic solid crystal thin film 3312 optically encapsulated by a protective layer 3314. The multilayer organic solid crystal thin film 3312 may include a clocked and stacked configuration of multiple organic solid crystal thin films (not separately shown). The multilayer organic solid crystal thin film 3312 may be configured to reflect a first polarization of incident light (P1) and transmit a second polarization of incident light (P2)

Figure 34:
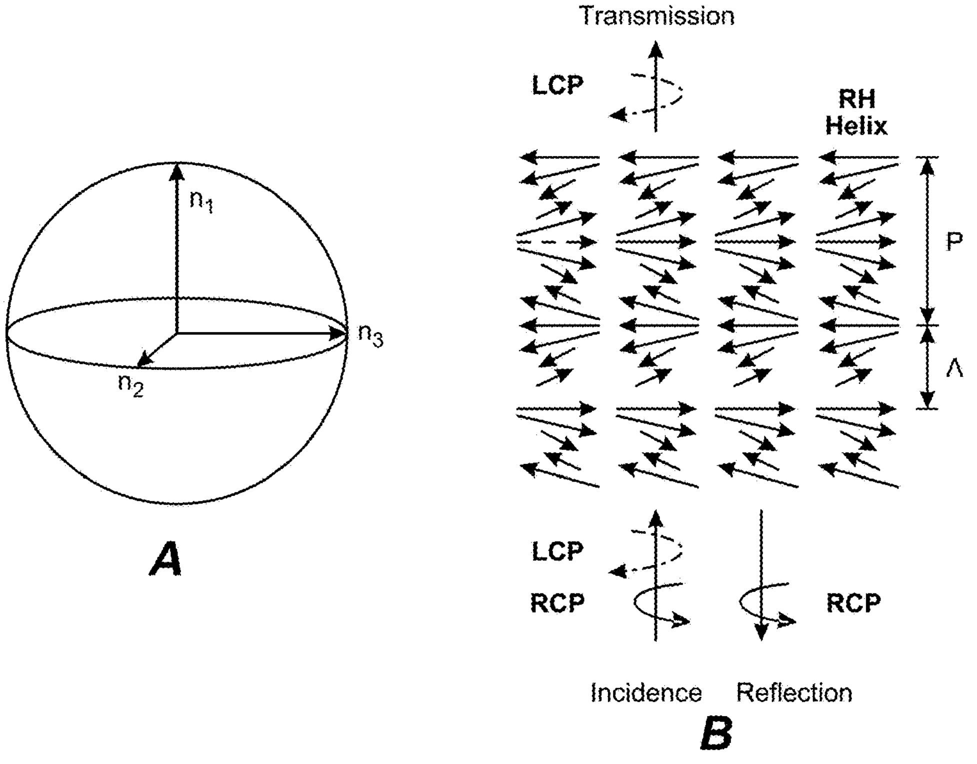
FIG. 34 is a graphic representation of the orientation of the major in-plane index ($n_3$) in a biaxial multilayer organic solid crystal thin film according to various embodiments.

Turning to FIG. 34, shown is both the architecture and the operation of an example circular reflective polarizer. The circular reflective polarizer may include a multilayer organic solid crystal thin film where each OSC layer in the multilayer stack includes a biaxially-oriented organic solid crystal material (i.e., $n_1 \neq n_2 \neq n_3$), as shown schematically in FIG. 34A. The multilayer may be characterized by a pitch length (P), which may correspond to two periods (2Λ) of index change.

In FIG. 34B, the plurality of arrows represent the orientation of a refractive index vector (e.g., $n_3$) in each OSC layer of the multilayer. In the illustrated embodiment of FIG. 36B, the right-handed (RH) circular reflective polarizer transmits light having left-hand circular polarization (LCP) and reflects light having right-hand circular polarization (RCP).

Figure 35:
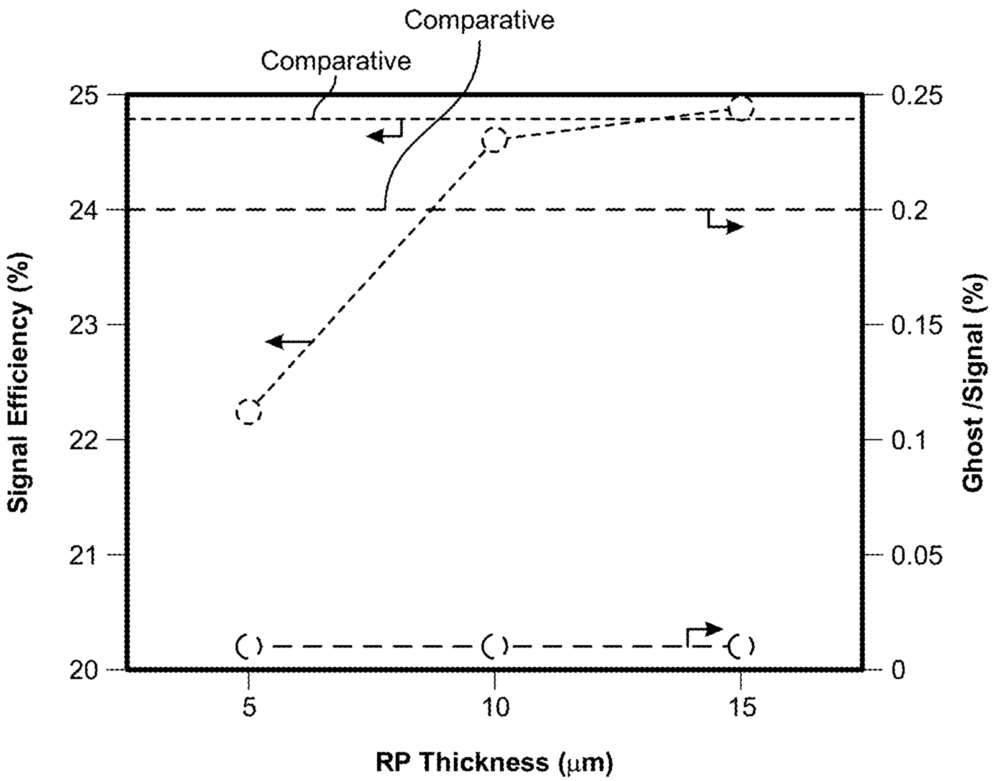
FIG. 35 is a plot of signal efficiency and ghost image suppression as a function of reflective polarizer thickness for a reflective polarizer including a biaxially oriented organic solid crystal material according to some embodiments.
Figure 36:
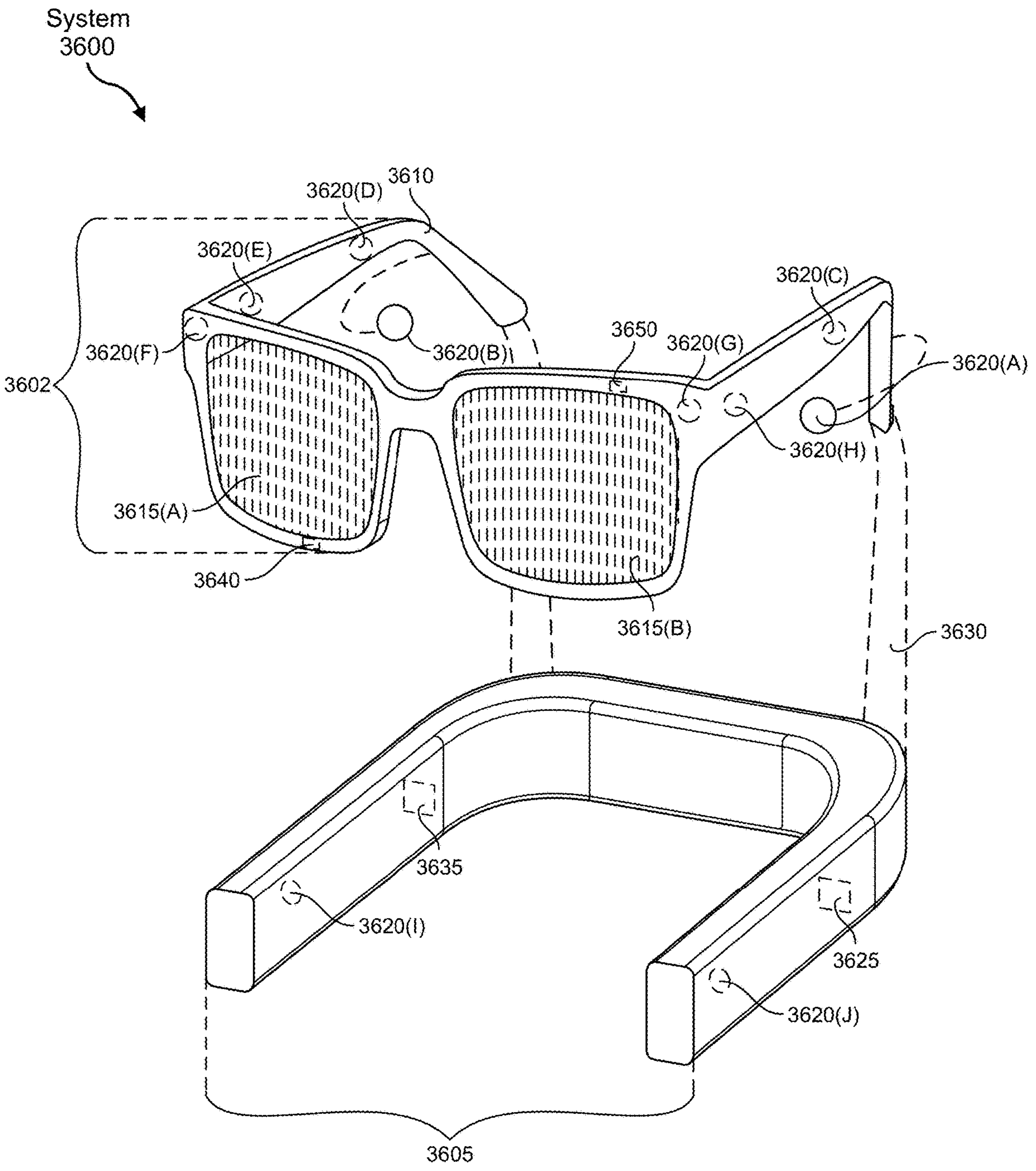
FIG. 36 is an illustration of exemplary augmented-reality glasses that may be used in connection with embodiments of this disclosure.
Figure 37:
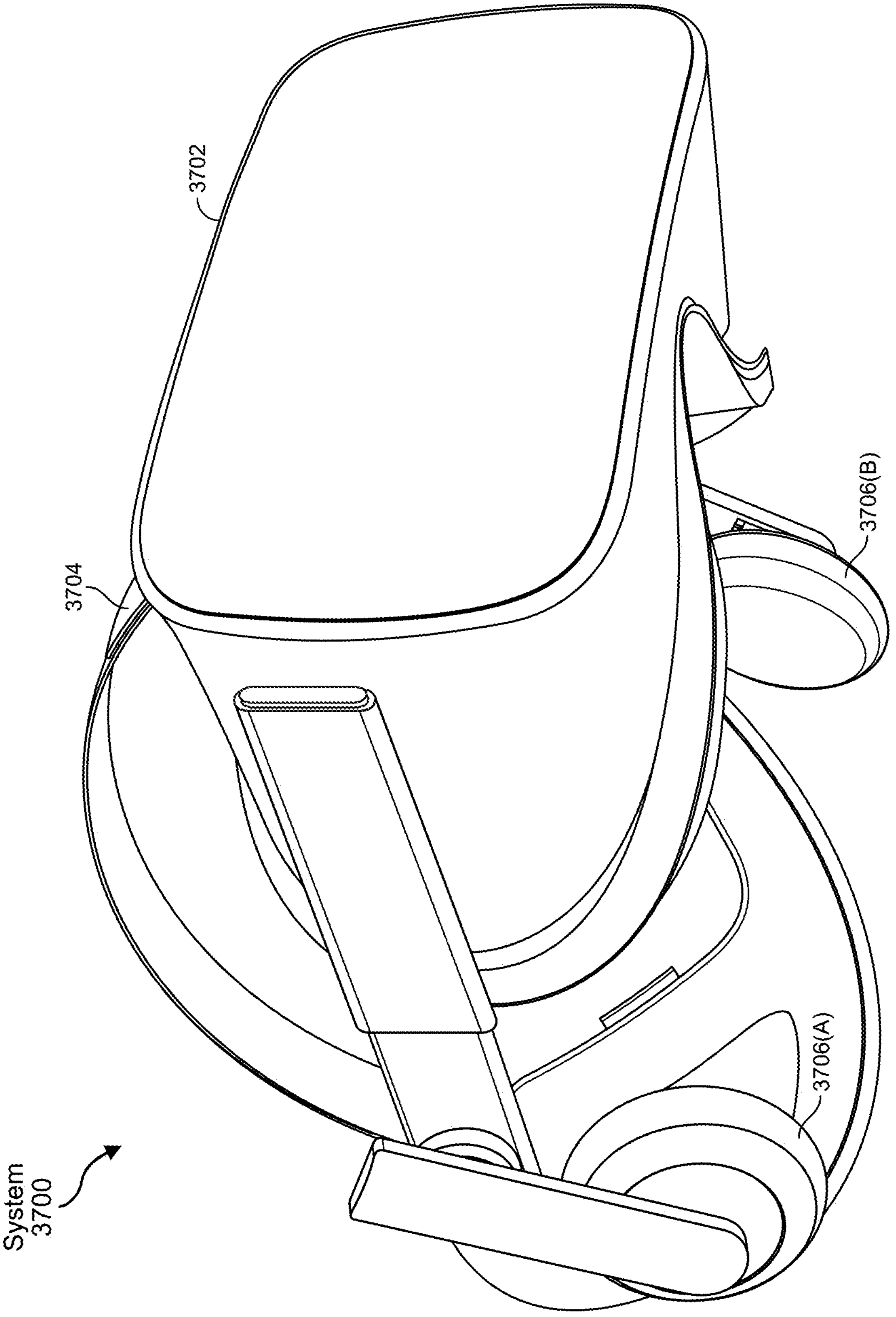
FIG. 37 is an illustration of an exemplary virtual-reality headset that may be used in connection with embodiments of this disclosure.

A plot of signal efficiency and ghost-to-signal ratio versus reflective polarizer thickness is shown in FIG. 35, and shows that a reflective polarizer including multiple clocked and stacked OSC thin films each having a biaxial refractive index may have higher signal efficiency and improved ghost suppression relative to comparative reflective polarizers.

Experimental—Synthesis of Organic Solid Crystal Materials

Synthesis: 2-(2-amino-5-methyl-1H-pyrrol-1-yl)-1-(4-chlorophenyl)ethan-1-one

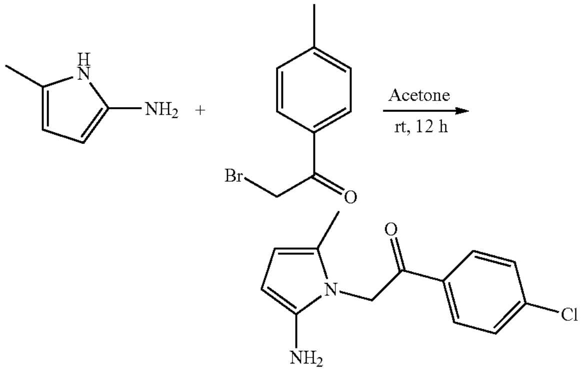

To a 250 mL round bottom flask 5-methyl-1H-pyrrol-2-amine (10.236 g, 0.08966 mol) and 2-bromo-1-(4-chlorophenyl)ethan-1-one (23.029 g, 0.09862 mol) were added then dissolved in 100 mL of acetone and allowed to react at room temperature for 12 h. The crude product was worked up by filtering off the solid and washing once with 10 mL acetone, 1 time with 50 mL dichloromethane, then 2 times with 50 mL diethyl ether, and 2 times with 50 mL hexanes. The product was carried forward without further purification. Yield 27.203 g (0.07862 mol, 87%). $^1$H NMR (400 MHz, DMSO-$d_6$) δ. 9.47 (s, 2H), 8.06 (d, J=8.2 Hz, 2H), 7.76 (d, J=8.2 Hz, 2H), 6.78 (s, 1H), 5.78 (s, 2H), 2.12 (s, 3H).

Synthesis: 5-(4-chlorophenyl)-2-methylimidazo[2,1-b]thiazole

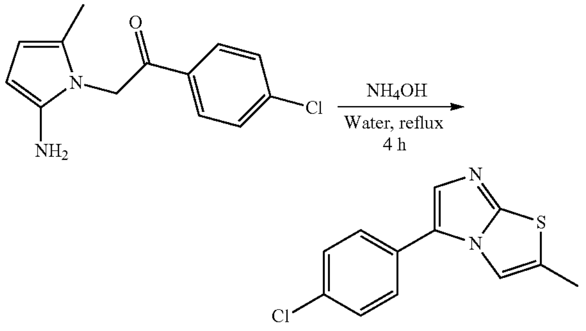

2-(2-amino-5-methyl-1H-pyrrol-1-yl)-1-(4-chlorophenyl)ethan-1-one was added to a 500 mL round bottom flask followed by 300 mL of 50% v/v $NH_4OH$ in water. The reaction mixture was heated to reflux for 4 h. After 4 h, the reaction was allowed to cool to room temperature. The crude solid was filtered off then redissolved in 250 mL of dichloromethane. The organic layer was then washed 1 time in saturated $NaHCO_3$ solution, 1 time in water, 1 time in saturated NaCl solution, dried over magnesium sulfate and concentrated. The crude product was purified via column chromatography 0 to 100% dichloromethane in hexanes followed by sublimation at 145° C. under high vacuum. Yield 15.655 g (0.06293 mol, 80%). $^1$H NMR (400 MHz, DMSO-d$_6$) δ. 7.76 (d, J=8.2 Hz, 2H), 7.60 (s, 1H), 7.36 (d, J=8.2 Hz, 2H), 6.42 (s, 1H), 2.41 (2, 3H).

Synthesis: 3,3'-sulfonylbis(nitrobenzene)

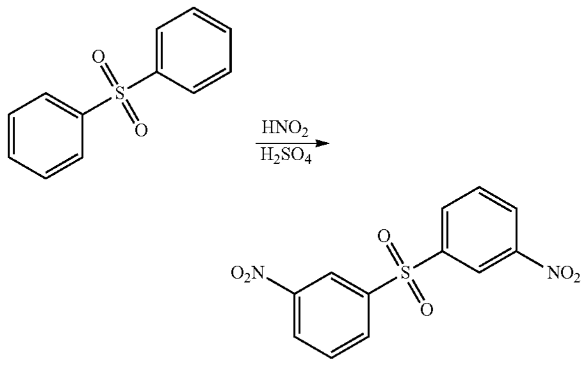

In a 500-mL round-bottom flask, diphenyl sulfone (19.7 g, 90.3 mmol) was dissolved in concentrated (99.99%) sulfuric acid (150 mL), and the solution was cooled on an ice bath. Then concentrated (67-70%) nitric acid (16 mL) was added dropwise via an addition funnel over 30 min. The reaction mixture turned yellow and after % of the nitric acid was added, a white precipitate formed. After complete addition of nitric acid, the mixture was allowed to warm up to room temperature and stirred for one hour. Then the reaction mixture was poured onto ice (ca. 1 L). The slurry was filtered, the pale-yellow precipitate was washed with water, saturated $NaHCO_3$, and water again. The resulting solid was suspended in boiling MeOH (3.5 L) and filtered. The resulting solid was recrystallized from boiling toluene (2 L) to afford a yellow crystalline solid (12.0 g, 43%). HPLC purity: 99%. $^1$H NMR (400 MHz, DMSO) δ8.76 (t, J=2.1 Hz, 2H), 8.54 (m, 4H), 7.95 (t, J=8.1 Hz, 2H).

Synthesis: methyl acridine-9-carboxylate

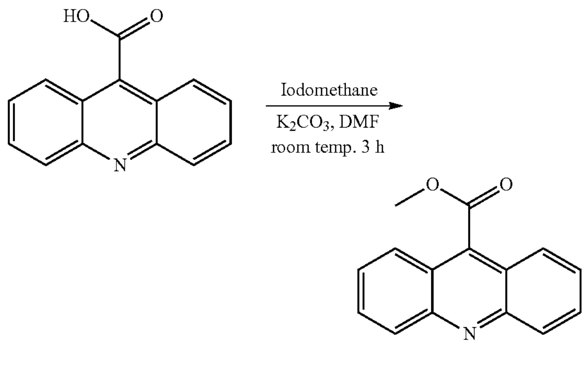

To a 250 mL 2 neck round bottom flask, acridine-9-carboxylic acid (5 g, 0.02210 mol) and potassium carbonate (12.370 g, 0.08950 mol) were add and dissolved in 50 mL of DMF. Then iodomethane (4.183 mL, 0.0672 mol) was added to the solution and reacted at room temperature for 3 hours. After 3 hours, the reaction was quenched by precipitating the product with brine solution. The product was filtered from the mixture then washed with DI water and dissolved in diethyl ether and concentrated. The product was purified by sublimation. $^1$H NMR (400 MHz, $CDCl_3$) δ. 8.27 (d, J=7.8 Hz, 2H), 8.02 (d, J=7.8 Hz, 2H), 7.84-7.80 (m, 2H), 7.63-7.59 (m, 2H), 4.22 (2, 3H).

Synthesis: trimethyl((4-nitrophenyl)ethynyl)silane

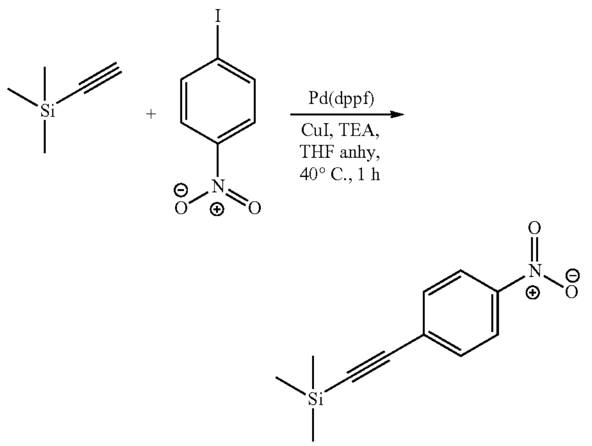

To a dry 100 mL 2-neck round bottom flask, 1-iodo-4-nitrobenzene (1 g, 0.004016 mol), Pd(dppf) (0.115 g, 0.0004819 mol) and CuI (0.061 g, 0.0003212 mol) were added and purged with $N_2$ 3 times. 20 mL of anhydrous THF and trimethylsilylethyne (0.473 mL, 0.004819 eq) were added to the 100 mL RB. The solution was stirred and sparged with $N_2$ for 10 minutes. Triethylamine (2.335 mL, 0.01676 mol) was then added dropwise. The reaction was stirred at 40° C. for 1 h then allowed to cool to room temperature and the solid was filtered off. The THF was removed and the crude product in chloroform was washed once with water, once with saturated sodium thiosulfate, once with water, once with saturated NaCl solution, dried over magnesium sulfate and concentrated. The crude product was purified via column chromatography 0 to 25% dichloromethane in hexanes. Yield 0.717 g (0.003278 mol, 82%). $^1$H NMR (400 MHz, $CDCl_3$) δ. 8.17 (d, J=8.4 Hz, 2H), 7.60 (d, J=8.4 Hz, 2H), 0.274 (s, 9H).

Synthesis: 1-ethynyl-4-nitrobenzene

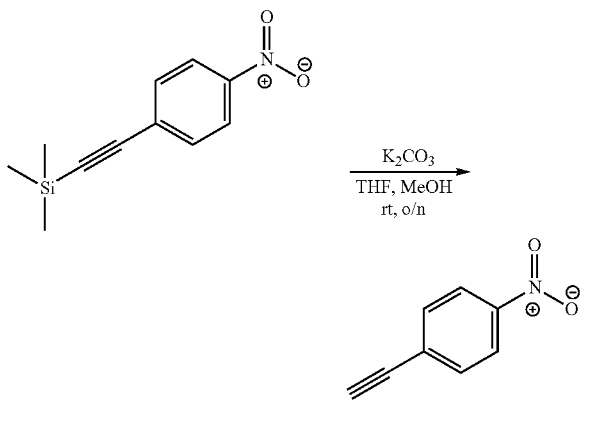

To a 50 mL round bottom flask, trimethyl((4-nitrophenyl) ethynyl)silane (0.717 g, 0.003278 mol) and potassium carbonate (0.769 g, 0.005562 mol) were added then dissolved in 2 mL of THF and 2 mL of MeOH and stirred at room temperature overnight. The reaction was quenched with 1M HCl then diluted with 20 mL of water. The pH of the solution was adjusted to between 1 and 2 with HCl. The product was extracted with diethyl ether 4×10 mL. The organic layer was washed with saturated NaCl solution and dried over sodium sulfate, filtered and concentrated. The diethyl ether was removed on a rotovap at 100 mbars until all the diethyl ether was gone by NMR. Product was carried forward crude without further purification.

Synthesis: 4-((4-nitrophenyl)ethynyl)benzonitrile

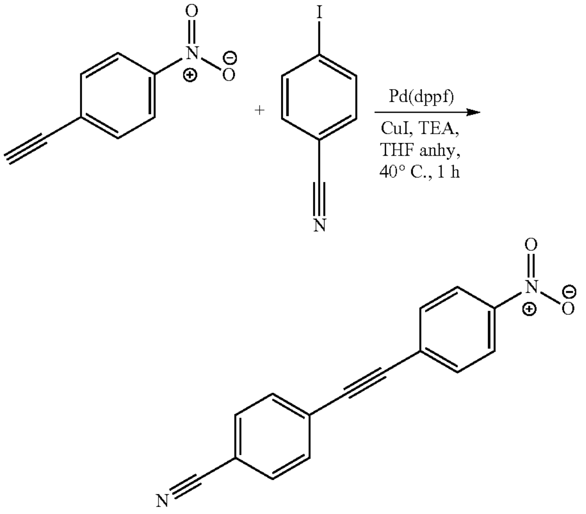

To a dry 50 mL 2-neck round bottom flask, 4-iodobenzonitrile (0.978 g, 0.004269 mol), Pd(dppf) (0.096 g, 0.0001314 mol) and CuI (0.050 g, 0.0002627 mol) were added and purged with $N_2$ 3 times. 10 mL of anhydrous THF and 1-ethynyl-4-nitrobenzene (0.483 g, 0.003284 mol) were added to the 50 mL RB and the solution was stirred and sparged with $N_2$ for 5 minutes. Triethylamine (2.381 mL, 0.01708 mol) was then added dropwise. The reaction was stirred at 40° C. for 1 h. The reaction was allowed to cool to room temperature and the THF was removed and the crude product was dissolved in chloroform and washed once with water, once with saturated sodium thiosulfate, once with water, once with saturated NaCl solution, dried over magnesium sulfate and concentrated. The crude product was purified via column chromatography 0 to 25% dichloromethane in hexanes. $^1$H NMR (400 MHz, $CDCl_3$) δ. 8.25 (d J=8.4, 2H), 7.71-7.64 (m, 6H).

Synthesis: 2-((trimethylsilyl)ethynyl)benzaldehyde

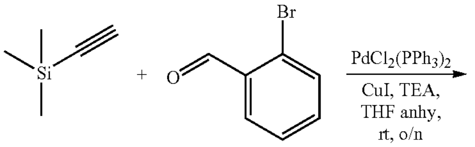

-continued

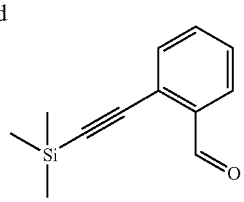

To a dry 250 mL 2-neck round bottom flask, $PdCl_2(PPh_3)_2$ (0.759 g, 0.001081 mol) and CuI (0.0411 g, 0.002161 mol) were added and purged with $N_2$ 3 times. 50 mL of anhydrous THF, 2-bromobenzaldehyde (6.309 mL, 0.05905 mol), and triethylamine (11.678 mL, 0.08378 mol) were added to the 250 mL RB. The solution was stirred and sparged with $N_2$ for 10 minutes. Trimethylsilylethyne (9.720 mL, 0.07027) was then added dropwise. The reaction was stirred at room temperature overnight. The THF was removed then the crude product was dissolved in dichloromethane and washed once with water, once with saturated sodium thiosulfate, once with water, once with saturated NaCl solution, dried over magnesium sulfate and concentrated. $^1$H NMR (400 MHz, $CDCl_3$) δ. 10.56 (s, 1H), 7.91 (d, J=7.7 Hz, 1H), 7.58-7.51 (m, 2H), 7.45-7.41 (m, 1H), 0.284 (s, 9H).

Synthesis: 2-ethynylbenzaldehyde

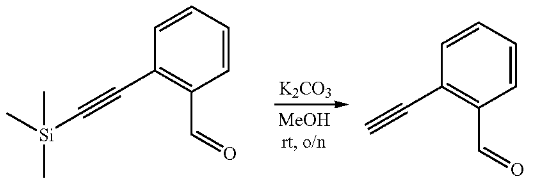

To a 100 mL round bottom flask, 2-((trimethylsilyl) ethynyl)benzaldehyde (2.036 g, 0.01 mol) and potassium carbonate (2.7811 g, 0.020 mol) were added and dissolved in 20 mL of MeOH and stirred at room temperature overnight. The reaction was quenched with 1M HCl then diluted with 50 mL of water. The pH of the solution was adjusted to between 1 and 2 with HCl. The product was extracted with diethyl ether 4×10 mL. The organic layer was washed with saturated NaCl solution and dried over sodium sulfate, filtered and concentrated. The diethyl ether was removed on the rotovap at 100 mbars until all the diethyl ether was gone by NMR. Yield 0.964 g (0.074 mol, 74%).

Once $^1$H NMR showed consumption of the starting materials, the reaction was quenched by adding distilled water and ethyl acetate. The organic layer was washed with hydrochloric acid solution (3M), distilled water, and saturated sodium chloride solution and then dried over magnesium sulfate and the solvent was removed. The crude product was purified by silica gel column chromatography. Product was carried through crude without further purification.

Synthesis: 2-((4-(methylthio)phenyl)ethynyl)benzaldehyde

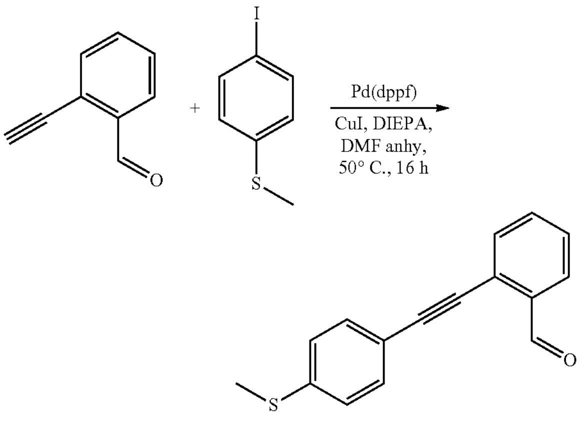

To a dry 100 mL 2-neck round bottom flask, (4-iodophenyl)(methyl)sulfane (1.232 g, 0.00428 mol), $PdCl_2(PPh_3)_2$ (0.138 g, 0.00019 mol) and CuI (0.077 g, 0.00039 mol) were added and purged with $N_2$ 3 times. 50 mL of anhydrous DMF and diisopropylethylamine (3.862 mL, 2.865 g, 0.02217 mol) were added to the 100 mL round bottom and the solution was stirred and sparged with $N_2$ for 10 minutes. 2-ethynylbenzaldehyde (0.961 g, 0.007392 mol) was then added dropwise. The solution was heated to 50° C. and sparged with $N_2$ for another 10 minutes. The reaction was then stirred at 50° C. overnight. The reaction was allowed to cool to room temperature and the crude product was precipitated with water and filtered. The crude product was dissolved in dichloromethane then washed once with water, once with saturated sodium thiosulfate, once with water, once with saturated NaCl solution, dried over magnesium sulfate and concentrated. Yield 0.945 g (0.00378 mol, 51%), $^1$H NMR (400 MHz, $CDCl_3$) δ. 10.64 (s, 1H), 7.95 (d, J=7.7 Hz, 1H), 7.64-7.56 (m, 3H), 7.47 (d, J=8.6 Hz, 2H), 7.24 (d, J=8.7 Hz, 2H), 2.51 (s, 3H).

Synthesis: 1,2-bis(4-(trifluoromethyl)phenyl)ethyne

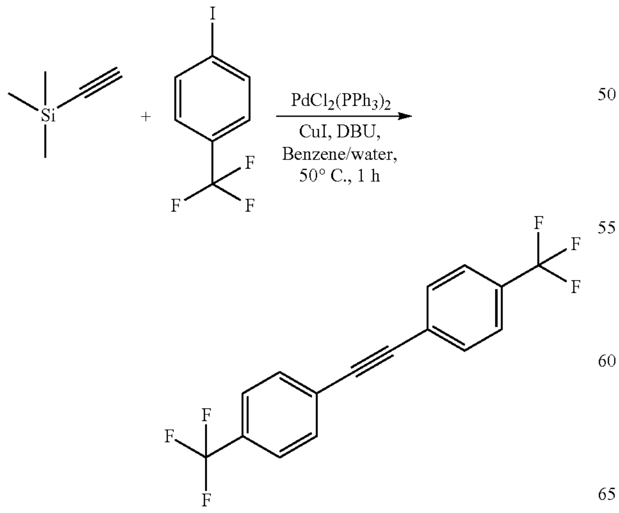

A 2-neck round bottom flask with a magnetic stir bar was evacuated and back-filled with $N_2$ 3 times. Under $N_2$, substituted 1-iodo-4-(trifluoromethyl)benzene (11.2 g, 0.0411 mol), $PdCl_2(PPh_3)_2$ (0.6 g, 0.0009 mol), and CuI (0.3 g, 0.0017 mol) were added to the flask. A solution of benzene (150 mL) and 1,8-diazabicyclo(5.4.0)undec-7-ene, DBU, (13.0 mL, 0.0866 mol) purged with dry $N_2$ for 20 mins, was added to the flask via syringe. Immediately thrimethylsilylethynylene (3.0 mL, 0.0217) followed by distilled water (0.2 mL, 0.0002 mol) were injected into the flask. The reaction mixture was heated to 50° C. and stirred overnight. The reaction was quenched by adding distilled water then ethyl acetate. The organic layer was washed 1 time with hydrochloric acid solution (3M), 1 time with distilled water, and 1 time with saturated NaCl solution, dried over magnesium sulfate, and then concentrated. The crude product was purified by silica gel column chromatography 0 to 5% dichloromethane in hexanes. $^1$H NMR (400 MHz, $CDCl_3$) δ7.67-7.62 (m 8H); $^{13}$C NMR (101 MHz, $CDCl_3$) δ131.97, 130.66, 130.33, 126.36, 125.37, 122.48, 90.12.

Synthesis: 1,2-bis(3,5-difluorophenyl)ethyne

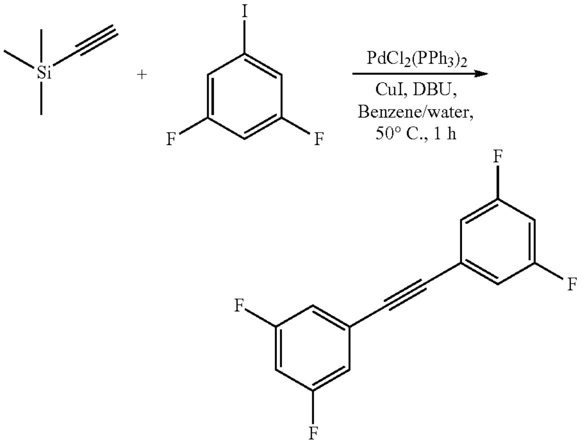

A 2-neck round bottom flask with a magnetic stir bar was evacuated and back-filled with $N_2$ 3 times. Under $N_2$, substituted 1,3-difluoro-5-iodobenzene (10.4 g, 0.0433 mol), $PdCl_2(PPh_3)_2$ (0.6 g, 0.0009 mol), and CuI (0.3 g, 0.0017 mol) were added to the flask. A solution of benzene (150 mL) and 1,8-diazabicyclo(5.4.0)undec-7-ene, DBU, (13.0 mL, 0.0866 mol) purged with dry $N_2$ for 20 mins, was added to the flask via syringe. Immediately thrimethylsilylethynylene (3.0 mL, 0.0217) followed by distilled water (0.2 mL, 0.0002 mol) were injected into the flask. The reaction mixture was heated to 50° C. and stirred overnight. The reaction was quenched by adding distilled water then ethyl acetate. The organic layer was washed 1 time with hydrochloric acid solution (3M), 1 time with distilled water, and 1 time with saturated NaCl solution, dried over magnesium sulfate, and then concentrated. The crude product was purified by silica gel column chromatography 0 to 5% dichloromethane in hexanes. $^1$H NMR (400 MHz, $CDCl_3$) δ7.05-7.03 (dt, 4H, Ar), 6.87-6.82 (tt, 2H); $^{13}$C NMR (101 MHz, $CDCl_3$) δ164.03, 163.89, 161.55, 161.42, 125.06, 124.95, 124.83, 114.78, 114.66, 114.59, 105.38, 105.13, 104.88, 88.79, 88.75, 88.71.

Synthesis: 1,2-bis(4-nitrophenyl)ethyne

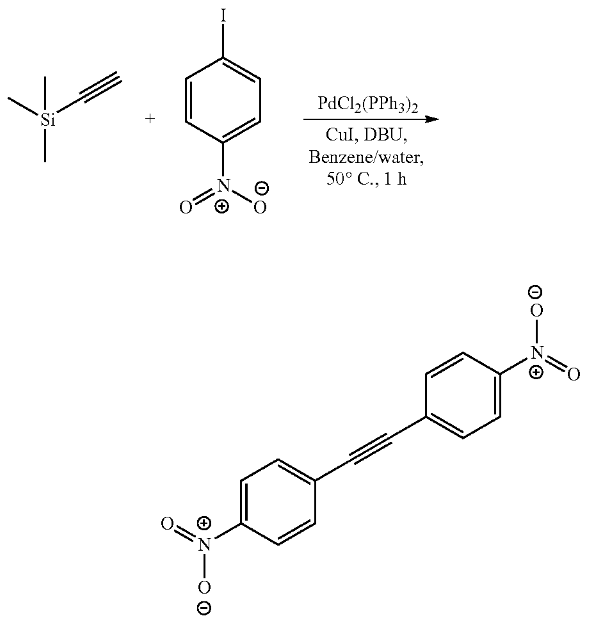

A 2-neck round bottom flask with a magnetic stir bar was evacuated and back-filled with $N_2$ 3 times. Under $N_2$, substituted 4-iodo-nitrobenzene (3.8 g, 0.0152 mol), $PdCl_2(PPh_3)_2$ (0.2 g, 0.0003 mol), and CuI (0.11 g, 0.00058 mol) were added to the flask. A solution of benzene (72 mL) and 1,8-diazabicyclo(5.4.0)undec-7-ene, DBU, (6.6 mL, 0.0433 mol) purged with dry $N_2$ for 20 mins, was added to the flask via syringe. Immediately thrimethylsilylethynylene (1.0 mL, 0.0072) followed by distilled water (0.1 mL, 0.0001 mol) were injected into the flask. The reaction mixture was heated to 50° C. and stirred overnight. The reaction was quenched by adding distilled water then ethyl acetate. The organic layer was washed 1 time with hydrochloric acid solution (3M), 1 time with distilled water, and 1 time with saturated NaCl solution, dried over magnesium sulfate, and then concentrated. The crude product was purified by silica gel column chromatography 0 to 50% dichloromethane in hexanes. $^1H$ NMR (400 MHz, $CDCl_3$) δ8.28-8.25 (d 4H), 7.73-7.71 (d 4H). $^{13}C$ NMR (101 MHz, $CDCl_3$) δ147.64, 132.62, 128.86, 123.79, 91.99.

Synthesis: 4,4'-(ethyne-1,2-diyl)dibenzonitrile

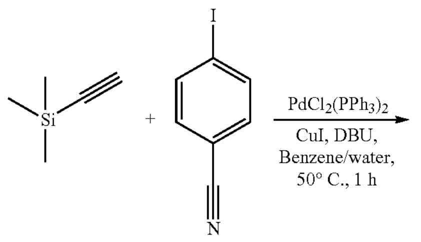

-continued

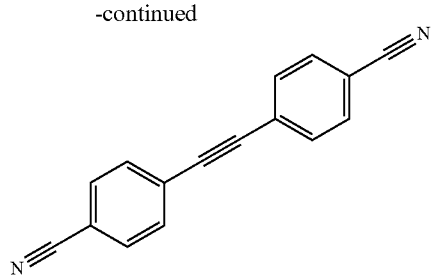

A 2-neck round bottom flask with a magnetic stir bar was evacuated and back-filled with $N_2$ 3 times. Under $N_2$, substituted 4-iodobenzonitrile (3.3 g, 0.0144 mol), $PdCl_2(PPh_3)_2$ (0.3 g, 0.0004 mol), and CuI (0.11 g, 0.00058 mol) were added to the flask. A solution of benzene (72 mL) and 1,8-diazabicyclo(5.4.0)undec-7-ene, DBU (6.5 mL, 0.0433 mol) purged with dry $N_2$ for 20 mins, was added to the flask via syringe. Immediately thrimethylsilylethynylene (1.0 mL, 0.0072) followed by distilled water (0.2 mL, 0.0002 mol) were injected into the flask. The reaction mixture was heated to 50° C. and stirred overnight. The reaction was quenched by adding distilled water then ethyl acetate. The organic layer was washed 1 time with hydrochloric acid solution (3M), 1 time with distilled water, and 1 time with saturated NaCl solution, dried over magnesium sulfate, and then concentrated. The crude product was purified by silica gel column chromatography 0 to 50% dichloromethane in hexanes. $^1H$ NMR (400 MHz, $CDCl_3$) δ7.69-7.62 (m 8H). $^{13}C$ NMR (101 MHz, $CDCl_3$) δ132.27, 127.07, 118.24, 112.44, 91.55.

Synthesis:
1,4-bis((3,5-difluorophenyl)ethynyl)benzene

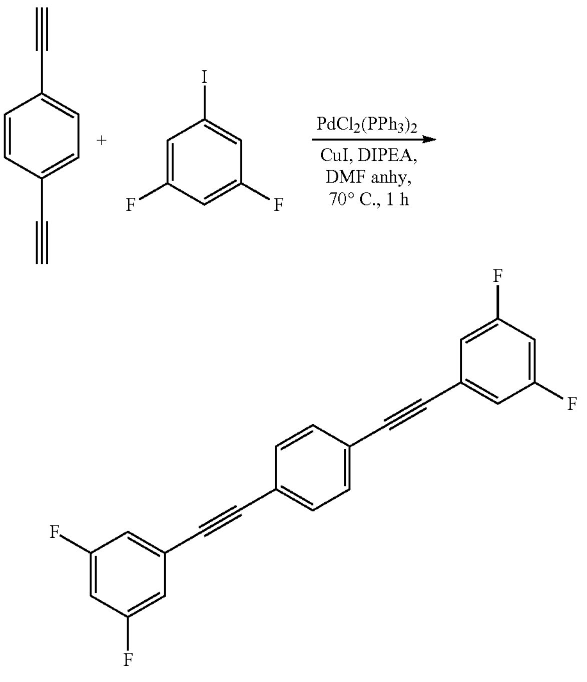

A 2-neck round bottom flask was purged 3 times with $N_2$ 250 mL then 1,3-difluoro-5-iodobenzene (2.2 mL, 0.0183 mol), 1,4-diethynylbenzene (0.9 g, 0.007 mol), $PdCl_2(PPh_3)_2$ (0.8 g, 0.0011 mol), and CuI (0.7 g, 0.0037 mol) were added to the flask. A solution of N,N-dimethylformamide, DMF (30 mL) and diisopropylethylamine, DIPeA, (6 eq) purged with dry $N_2$ for 20 mins, was added to the flask via syringe. The reaction mixture was heated to 70° C. and stirred overnight. The reaction was quenched by adding distilled water and precipitate was filtered off and the crude product was purified via sublimation. $^1H$ NMR (400 MHz, $CDCl_3$) δ7.52 (s, 4H), 7.05-7.04 (dt, 4H), 6.85-6.80 (tt, 2H). $^{13}C$ NMR (101 MHz, $CDCl_3$) δ164.03, 163.89, 161.55, 161.42, 131.75, 125.71, 125.59, 125.48, 122.80, 114.71, 114.44, 104.97, 104.72, 104.47, 90.68, 89.17.

Synthesis: trimethyl((4-((trifluoromethyl)thio)phenyl)ethynyl)silane

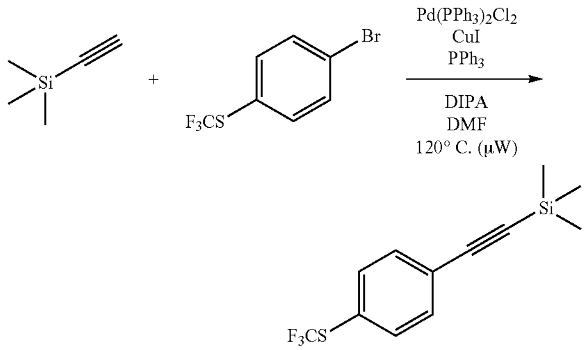

In a 20-mL microwave vial, trimethylsilylacetylene (1.7 mL, 12.3 mmol), 1-bromo-4-(trifluoromethyl)thiobenzene (2.55 g, 9.9 mmol), bis(triphenylphosphine)palladium(II) chloride (120 mg, 0.17 mmol), triphenylphosphine (210 mg, 0.80 mmol), copper(I) iodide (43 mg, 0.23 mmol), diisopropylamine (10 mL, 71.4 mmol), and DMF (3 mL) were combined. The mixture was degassed by sparging with nitrogen, sealed, and heated in a microwave reactor at 120° C. for 25 min. The reaction mixture was diluted with diethyl ether, filtered, and the filtrate was washed with 0.1 N HCl (2×) and saturated NaCl. The organic layer was then dried over anhydrous $Na_2SO_4$—, filtered, and concentrated to obtain brown crystalline solid. The crude product was purified by flash chromatography ($SiO_2$, eluted with hexane) to afford yellow liquid (1.98 g, 73%). $^1H$ NMR (400 MHz, $CDCl_3$) δ7.58 (d, J=8.2 Hz, 2H), 7.49 (d, J=8.4 Hz, 2H), 0.26 (s, 9H).

Synthesis: (4-ethynylphenyl)(trifluoromethyl)sulfane

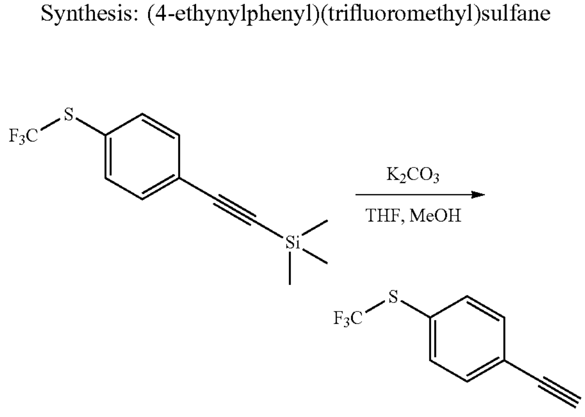

In a 50-mL round-bottom flask, trimethyl((4((trifluoromethyl)thio)phenyl) ethynyl)silane (1.98 g, 7.2 mmol) was dissolved in THF (10 mL) and MeOH (10 mL). Potassium carbonate (2.5 g, 18 mmol) was added, and the mixture was stirred at ambient temperature overnight. Then the reaction mixture was filtered and the filtrate was concentrated to afford brownish oil. The crude product was dissolved in diethyl ether and washed with 0.1 N HCl (2×) and saturated NaCl. Ether solution was dried over anhydrous $Na_2SO_4$, filtered, and concentrated to afford a yellow liquid (1.42 g, 98%). $^1H$ NMR (400 MHz, $CDCl_3$) δ7.61 (d, J=8.3 Hz, 2H), 7.56-7.49 (m, 2H), 3.20 (s, 1H).

Synthesis: 1,2-bis(4-((trifluoromethyl)thio)phenyl)ethyne

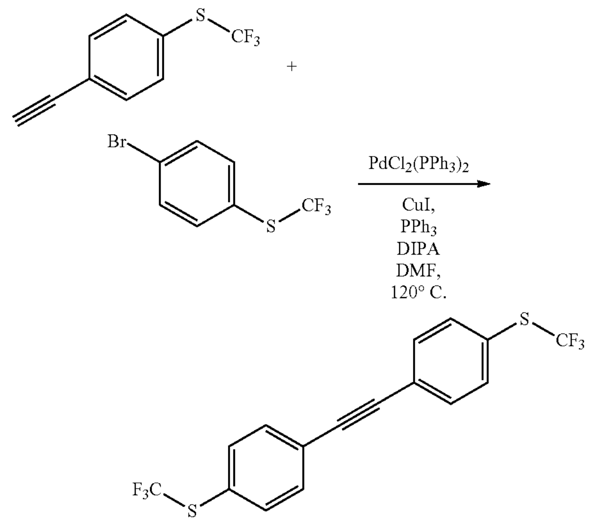

In a 20-mL microwave vial, (4-ethynylphenyl)(trifluoromethyl)sulfane (1.4 g, 6.9 mmol), 1-bromo-4-(trifluoromethyl)thiobenzene (1.8 g, 7.0 mmol), $PdCl_2(PPh_3)_2$, (95 mg, 0.14 mmol), triphenylphosphine (140 mg, 0.53 mmol), CuI, (29 mg, 0.15 mmol), diisopropylamine (8 mL, 57 mmol), and DMF (2 mL) were combined. The mixture was degassed by sparging with nitrogen, sealed, and heated in a microwave reactor at 120° C. for 25 min. The reaction mixture was diluted with diethyl ether, and filtered. The filtrate was washed with 0.1 N HCl (2×) and saturated NaCl, and then the organic layer was dried over anhydrous $Na_2SO_4$, filtered, and concentrated to obtain brown crystalline solid. The crude product was purified by flash chromatography ($SiO_2$, eluted with hexane). The resulting product was additionally purified by recrystallization from MeOH to afford a white crystalline solid (1.5 g, 57%). HPLC purity: 99% (250 nm). $^1H$ NMR (400 MHz, $CDCl_3$) δ7.65 (d, J=8.1 Hz, 4H), 7.57 (d, J=8.3 Hz, 4H). M.P.=113-114° C.

Synthesis: 1,2-bis(4-(pentafluoro-$\lambda^6$-sulfaneyl)phenyl)ethyne

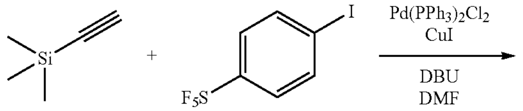

-continued

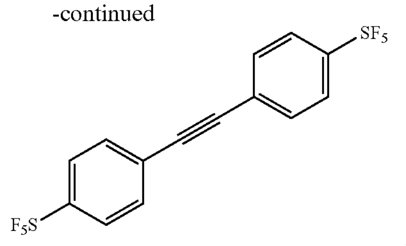

In a 50-mL round-bottom flask, 4-iodophenylsulfur pentafluoride (2.2 g, 6.7 mmol), $PdCl_2(PPh_3)_2$ (95 mg, 0.135 mmol), CuI (64 mg, 0.34 mmol), 1,8-diazabicyclo[5.4.0]undec-7-ene (6.0 mL, 40 mmol), and DMF (6 mL) were combined. The reaction mixture was degassed by purging with nitrogen. To the resulting green solution, trimethylsilylacetylene (0.47 mL, 3.4 mmol) was added and the flask was sealed with a septum and stirred under nitrogen atmosphere at ambient temperature for 5 hours. Then the reaction mixture was diluted with diethyl ether and 0.1 N HCl (1:1, ca. 150 mL), filtered through a Celite plug, and the filter cake was washed with ether. The filtrate was transferred to a separating funnel, partitioned, and the aqueous layer was discarded. The ether layer was washed with 0.1 N HCl (2×) and saturated NaCl, then dried over anhydrous $Na_2SO_4$, filtered, and concentrated. The orange-brown residue was purified by flash chromatography ($SiO_2$, eluted with hexane). Yield: 834 mg (57%) as a white crystalline powder. HPLC purity: 100% (250 nm). $^1H$ NMR (400 MHz, $CDCl_3$) δ7.77 (d, J=8.9 Hz, 3H), 7.62 (d, J=8.5 Hz, 4H). M.P.=98-99° C.

Synthesis: 1,2-bis(perfluorophenyl)ethyne

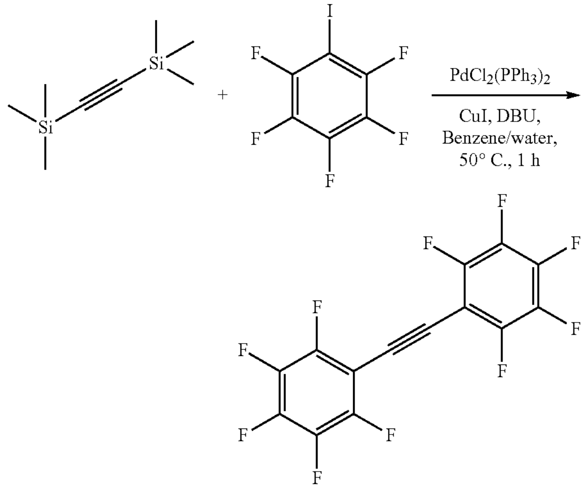

A 2-neck round bottom flask with a magnetic stir bar was evacuated and back-filled with $N_2$ 3 times. Under $N_2$, substituted 1,2,3,4,5-pentafluoro-6-iodobenzene (4.5 g, 0.0152 mol), $PdCl_2(PPh_3)_2$ (0.2 g, 0.0003 mol), and CuI (0.11 g, 0.00058 mol) were added to the flask. A solution of benzene (72 mL) and 1,8-diazabicyclo(5.4.0)undec-7-ene, DBU, (6.6 mL, 0.0433 mol) purged with dry $N_2$ for 20 mins, was added to the flask via syringe. Immediately 1,2-bis(trimethylsilyl)ethyne (1.6 mL, 0.0072 mol) followed by distilled water (0.1 mL, 0.0001 mol) were injected into the flask. The reaction mixture was heated to 50° C. and stirred overnight. The reaction was quenched by adding distilled water then ethyl acetate. The organic layer was washed 1 time with hydrochloric acid solution (3M), 1 time with distilled water, and 1 time with saturated NaCl solution, dried over magnesium sulfate, and then concentrated. The crude product was purified by silica gel column chromatography 0 to 50% dichloromethane in hexanes. $^{19}F$ NMR (376 MHz, $CDCl_3$) δ-115.1--134.4 (m 2F), -148.2--149.4 (m 1F), -155.2--157.8 (m 2F).

Synthesis: (3-fluoro-4-((4-(methylthio)phenyl)ethynyl)phenyl)(methyl)sulfane

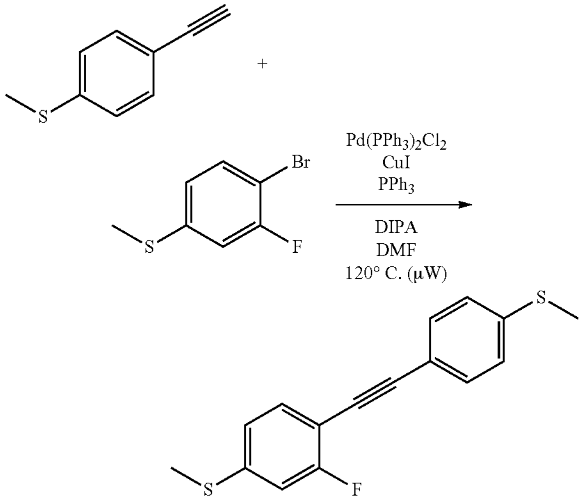

The synthesis followed the general procedure for Sonogashira coupling. From 4-ethynylthioanisole (1.33 g, 9 mmol), 4-bromo-3-fluorothioanisole (1.8 g, 8.1 mmol), bis(triphenylphosphine)palladium(II) chloride (170 mg, 0.24 mmol), triphenylphosphine (157 mg, 0.55 mmol), copper(I) iodide (93 mg, 0.49 mmol), diisopropylamine (7 mL, 50 mmol), and DMF (2 mL). Yield: 1.6 g (62%). HPLC purity: 98%. $^1H$ NMR (400 MHz, $CDCl_3$) δ7.47 (d, J=8.5 Hz, 2H), 7.41 (ddd, J=8.5, 7.4, 1.4 Hz, 1H), 7.23 (d, J=8.4 Hz, 2H), 7.01-6.95 (m, 2H), 2.52 (s, 3H), 2.52 (s, 3H). M.P. 118.5-119° C. (after additional purification by sublimation).

Synthesis: (3-fluoro-4-((4-(methylthio)phenyl)ethynyl)phenyl)(methyl)sulfane

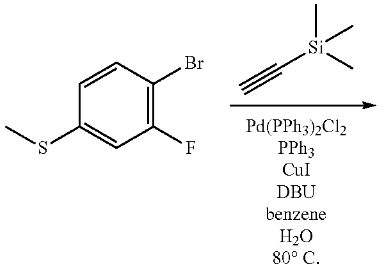

-continued

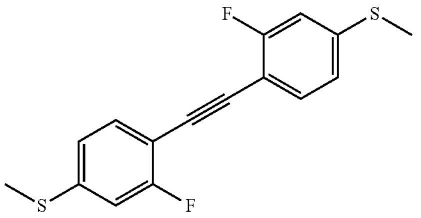

The synthesis followed the general procedure for one-pot double Sonogashira coupling. From 4-bromo-3-fluorothioanisole (16.0 g, 72 mmol), trimethylsilylacetylene (5.5 mL, 40 mmol), bis(triphenylphosphine)palladium(II) chloride (2.0 g, 2.8 mmol), triphenylphosphine (3.0 g, 11.4 mmol), copper(I) iodide (1.1 g, 5.8 mmol), DBU (65 mL, 435 mmol), water (0.5 mL, 28 mmol), and benzene (250 mL). Yield: 7.11 g (64%) as a colorless solid. HPLC purity: 99%. $^1$H NMR (400 MHz, $CDCl_3$) δ 7.41 (dd, J=8.4, 7.4 Hz, 2H), 6.98 (dd, J=6.2, 2.0 Hz, 2H), 6.95 (dd, J=8.3, 1.7 Hz, 2H), 2.49 (s, 6H). M.P. 130° C. (after additional purification by sublimation).

Synthesis: (3-fluoro-4-((4-(methylthio)phenyl)ethynyl)phenyl)(methyl)sulfane

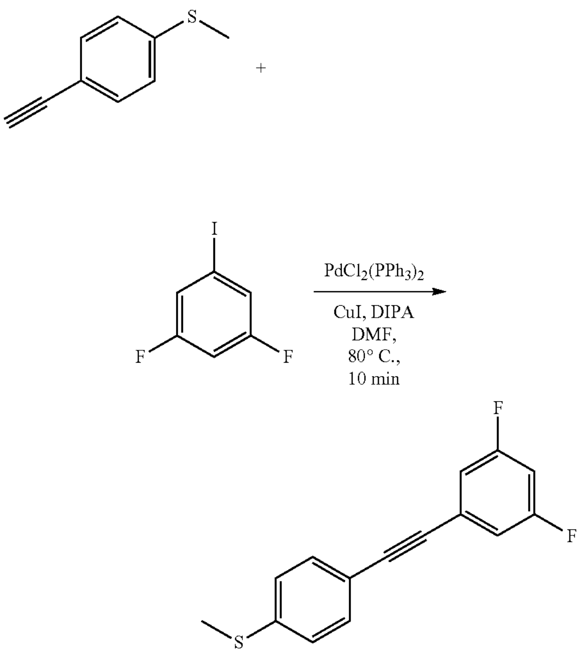

The synthesis followed the general procedure for Sonogashira coupling. From 4-ethynylthioanisole (1.48 g, 10 mmol), 1,3-difluoro-5-iodobenzene (2.4 g, 10 mmol), bis (triphenylphosphine)palladium(II) chloride (120 mg, 0.17 mmol), copper(I) iodide (40 mg, 0.21 mmol), diisopropylamine (10 mL, 71 mmol), and DMF (3 mL). Yield: 2.0 g (77%) as a colorless solid. HPLC purity: 99%. $^1$H NMR (400 MHz, $CDCl_3$) δ7.46-7.40 (m, 2H), 7.24-7.18 (m, 2H), 7.03 (dtd, J=6.2, 4.9, 2.2 Hz, 2H), 6.79 (tt, J=9.0, 2.4 Hz, 1H), 2.50 (s, 3H). M.P. 60° C.

Synthesis: trimethyl(4-((4-(methylthio)phenyl)ethynyl)phenyl)silane

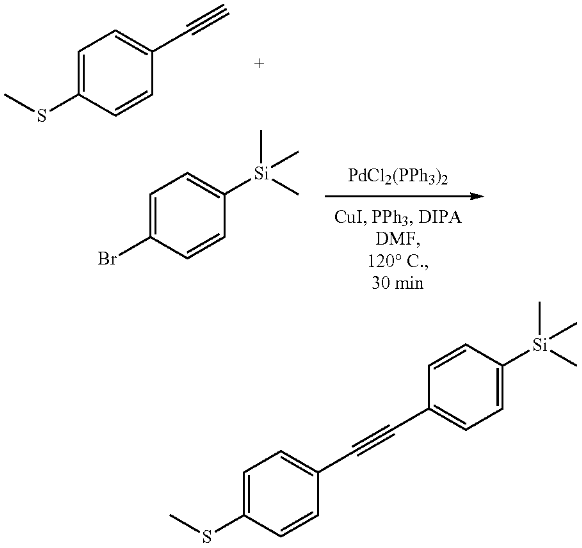

The synthesis followed the general procedure for Sonogashira coupling. From 4-ethynylthioanisole (1.48 g, 10 mmol), 1-bromo-4-trimethylsilylbenzene (2.3 g, 10 mmol), bis(triphenylphosphine)palladium(II) chloride (120 mg, 0.17 mmol), triphenylphosphine (210 mg, 0.80 mmol), copper(I) iodide (40 mg, 0.21 mmol), diisopropylamine (10 mL, 71 mmol), and DMF (3 mL). Yield: 1.50 g (51%) as a colorless solid. HPLC purity: 96%. Additionally purified by recrystallization from hexane and sublimation to yield colorless crystalline solid. $^1$H NMR (400 MHz, $CDCl_3$) δ7.51 (s, 4H), 7.46 (d, J=8.4 Hz, 2H), 7.22 (d, J=8.4 Hz, 2H), 2.50 (s, 3H), 0.29 (s, 9H). M.P. 125.5-127° C. (after additional purification by sublimation).

Synthesis: 1,2-bis(3,5-dibromophenyl)ethyne

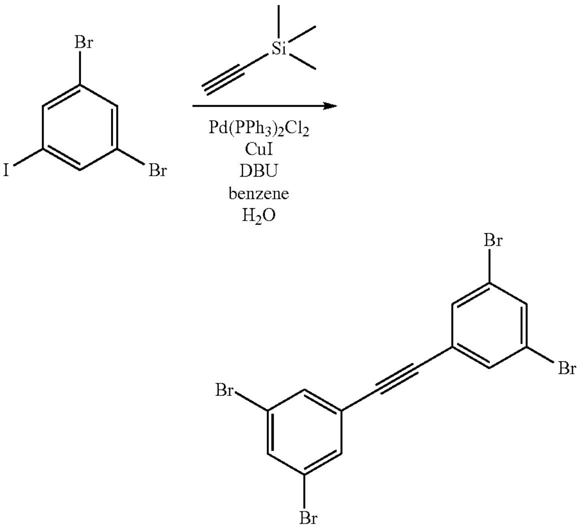

The synthesis followed the general procedure for one-pot double Sonogashira coupling. From 1,3-dibromo-5-iodobenzene (4.32 g, 12 mmol), trimethylsilylacetylene (0.93 mL, 6.7 mmol), bis(triphenylphosphine)palladium(II) chloride (260 mg, 0.36 mmol), copper(I) iodide (101 mg, 0.53 mmol), DBU (11 mL, 74 mmol), water (0.08 mL, 4.4 mmol), and benzene (40 mL). Yield: 1.59 g (54%) as a colorless solid. HPLC purity: 99%. $^1$H NMR (400 MHz, $CDCl_3$) δ7.67 (t, J=1.7 Hz, 2H), 7.59 (d, J=1.7 Hz, 4H).

Synthesis: 1,2-bis(4-bromo-2-fluorophenyl)ethyne

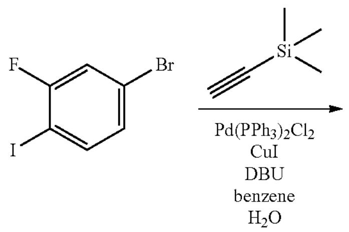

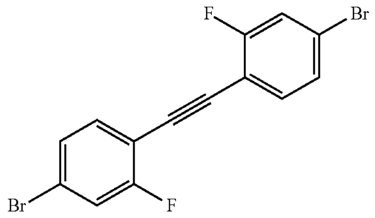

The synthesis followed the general procedure for one-pot double Sonogashira coupling. From 1-bromo-3-fluoro-4-iodobenzene (1.8 g, 6 mmol), trimethylsilylacetylene (0.46 mL, 3.3 mmol), bis(triphenylphosphine)palladium(II) chloride (130 mg, 0.18 mmol), copper(I) iodide (55 mg, 0.3 mmol), DBU (5.5 mL, 37 mmol), water (0.04 mL, 2.2 mmol), and benzene (20 mL). Yield: 0.83 g (74%) as a colorless solid. HPLC purity: 99%. $^1$H NMR (400 MHz, $CDCl_3$) δ7.40 (dd, J=8.5, 7.4 Hz, 2H), 7.31 (td, J=8.4, 1.9 Hz, 4H). M.P. 160-162° C.

Synthesis: 1,2-bis(3,5-dichlorophenyl)ethyne

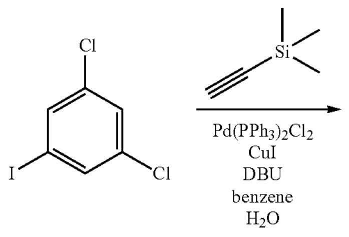

-continued

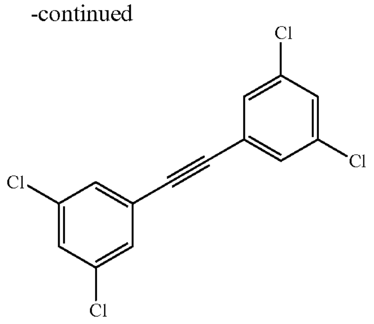

The synthesis followed the general procedure for one-pot double Sonogashira coupling. From 1,3-dichloro-5-iodobenzene (2.72 g, 10 mmol), trimethylsilylacetylene (0.73 mL, 5.3 mmol), bis(triphenylphosphine)palladium(II) chloride (141 mg, 0.20 mmol), copper(I) iodide (21 mg, 0.11 mmol), DBU (9 mL, 60 mmol), water (0.08 mL, 4.4 mmol), and benzene (32 mL). Yield: 0.41 g (26%) as a colorless solid. HPLC purity: 98%. $^1$H NMR (400 MHz, $CDCl_3$) δ7.39 (d, J=1.9 Hz, 4H), 7.37 (t, J=1.9 Hz, 2H). M.P.=200-201° C.

Synthesis: 2H-1,2,3-triazole-4,5-dicarbonitrile

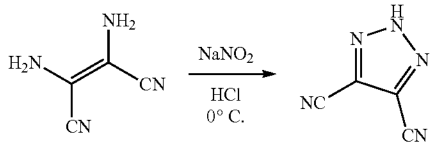

In a 1-L 3-neck round-bottom flask, a suspension of diaminomeleonitrile (103.8 g, 0.96 mol) in a mixture of 1 M HCl (250 mL) and 36% HCl (250 mL) was stirred vigorously and cooled to 0° C. Then a solution of $NaNO_2$ (72 g, 1.04 mol) in water (250 mL) was added dropwise via an addition funnel, controlling the addition rate so that the temperature of the reaction mixture did not exceed 5° C. The addition was carried out for three hours. Then the reaction mixture was allowed to stir in the ice bath and reach room temperature over 16 hours under constant nitrogen flow. The reaction mixture was filtered, the brown precipitate was washed with 1 N HCl and tert-butyl methyl ether (TBME). The combined filtrates were extracted with TBME (1×600 mL, 2×300 mL). Combined organic layers were dried over anhydrous $Na_2SO_4$, then filtered and concentrated. The resulting yellow solid was dried under high vacuum overnight. Dry yellow powder was sublimed (125° C., 1-3 mbar) portion-wise to afford the pure product as white crystalline solid (109.87 g, 96%). $^1$H NMR (400 MHz, MeOD) δ4.93 (s, 1H). $^{13}$C NMR (101 MHz, MeOD) ι126.24, 110.18.

Synthesis: 9,10-bis(4-(trifluoromethyl)phenyl)anthracene

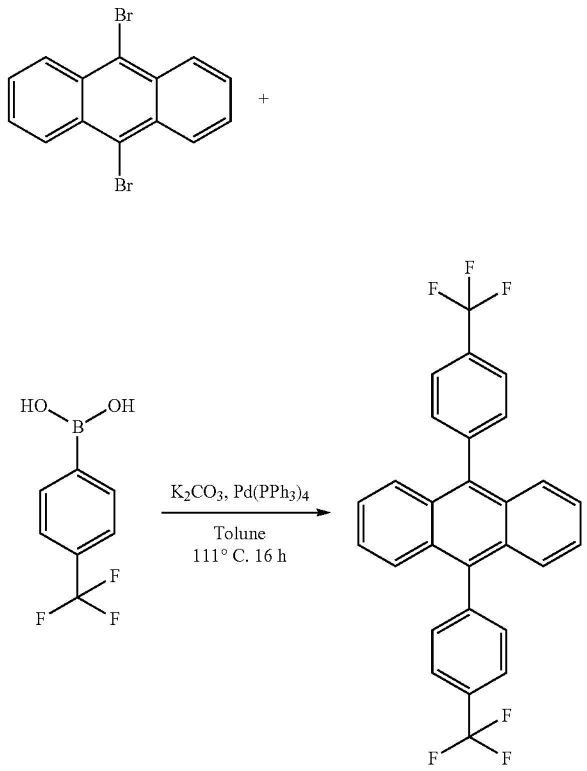 [SMILES: Brc1c2ccccc2c(Br)c2ccccc12 ; OB(O)c1ccc(C(F)(F)F)cc1 ; FC(F)(F)c1ccc(-c2c3ccccc3c(-c3ccc(C(F)(F)F)cc3)c3ccccc23)cc1]

20 mL of toluene was added to a 100 mL 2 neck round bottom flask placed under vacuum and purged with $N_2$ three times, and the $N_2$ was bubbled through the solution for another 10 min. 9,10-dibromoanthracene (2 g, 0.00595 mol), (4-(trifluoromethyl)phenyl)boronic acid (2.83 g, 0.01488 mol) potassium carbonate (9.696 g, 0.02976 mol), and $Pd(PPH_3)_4$ (0.344 g, 0.0002976 mol) were all added to the reaction flask and the solution was sparged with nitrogen for another 10 minutes. The reaction was then heated to 111° C. and refluxed for 16 hours. After 16 hours, the reaction was allowed to cool to room temperature. The reaction was worked up by adding 100 mL of water and extracting 3 times with ethyl acetate. The organic phase was washed once with water, once with 3 M HCl, once with brine solution, dried over magnesium sulfate, and concentrated.

Synthesis: 9,10-bis(4-nitrophenyl)anthracene

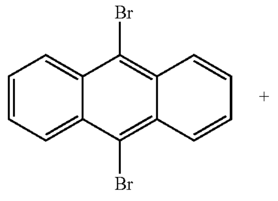

-continued

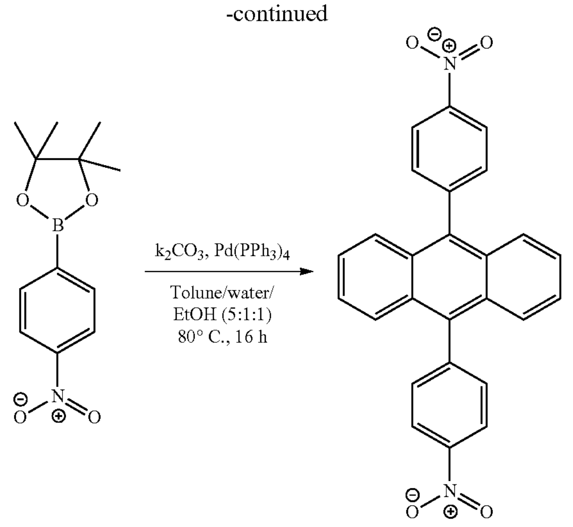

20 mL of toluene, 4 mL of water and 4 mL of ethanol were added to a 100 mL 2-neck round bottom flask placed under vacuum and purged with $N_2$ three times, and the $N_2$ was bubbled through the solution for another 10 min. 9,10-dibromoanthracene (2 g, 0.00595 mol), 4-nitrophenylboronic acid pinacol ester (3.71 g, 0.01488 mol) potassium carbonate (9.696 g, 0.02976 mol), and $Pd(PPH_3)_4$ (0.344 g, 0.0002976 mol) were all added to the reaction flask and the solution was sparged with nitrogen for another 10 minutes. The reaction was then heated to 80° C. 16 hours. After 16 hours, the reaction was allowed to cool to room temperature. The reaction was worked up by adding 100 mL of water and extracting 3 times with ethyl acetate. The organic phase was washed once with water, once 3 M HCl, once with brine solution, dried over magnesium sulfate, and concentrated.

Disclosed are methods for forming an organic solid crystal thin film. In particular embodiments, the methods may be used to control the surface roughness of the thin film without the need for post-formation slicing, grinding, and polishing steps. Using a seed crystal to nucleate an organic solid crystal from a liquid or molten phase containing an organic precursor, in an example method, an organic solid crystal thin film may be cast or molded using a non-volatile medium material (e.g., oil) to template crystal growth. Vapor phase and solid phase nucleation and growth paradigms are also disclosed. In some embodiments, an anti-nucleation layer or surface may be used to locally discourage crystallization and enable large area crystals. In some embodiments, a substrate surface may include a photoalignment layer. In particular examples, a substrate surface may be chemically treated to encourage a desired molecular alignment of an over-formed organic solid crystal.

In some embodiments, an organic precursor may be deposited directly over a layer of a non-volatile medium material, which may provide a smooth interface for the formation of the organic solid crystal thin film. Thermal processing may be used to induce nucleation and growth of the organic solid crystal phase.

In further embodiments, a mixture containing an organic precursor and a non-volatile medium material may be deposited over a substrate. If provided, a substrate may be patterned to include a 3D structure that is incorporated into the over-formed thin film. In a similar vein, a functional layer may be formed over the deposition surface of a substrate or mold and transferred to an over-formed organic solid crystal upon separation of the organic solid crystal from the substrate or mold. Thermal processing may be used to induce homogeneous mixing, and subsequent phase separation of the organic precursor and the non-volatile medium material, as well as nucleation and growth of the organic solid crystal phase. During nucleation and growth, according to various embodiments, at least one surface of the thin film may directly contact the non-volatile medium material, which may be effective to mediate molecular-level surface roughness of the nascent organic crystal(s).

In some embodiments, an organic solid crystal thin film may include an organic crystalline phase and may be characterized by a refractive index of at least approximately 1.5 at 589 nm, and a surface roughness (e.g., over an area of at least 1 $cm^2$ and independent of surface features such as gratings, etc.) of less than approximately 10 micrometers. The organic solid crystal thin film may be single crystal and may be characterized by three mutually orthogonal refractive indices. Further advantages of the disclosed methods may include improved processability and lower cost relative to alternate methods.

Example OSC materials include small molecules, macromolecules, liquid crystals, organometallic compounds, oligomers, and polymers, and may include organic semiconductors such as polycyclic aromatic compounds, e.g., anthracene, phenanthrene, and the like. Methods of manufacturing organic solid crystals may include crystal growth from a melt or solution, chemical or physical vapor deposition, and solvent coating onto a substrate. The foregoing methods may be applied in conjunction with one or more optional post-deposition steps, such as annealing, polishing, dicing, etc.

Also disclosed are active and passive optical devices and systems that include an optical modulator configured to modulate a beam of light. Optical modulators may be characterized as absorptive and/or refractive and may be adapted to manipulate various parameters of a light beam, including its frequency, amplitude, phase, absorption, polarization, etc. Active index modulation may beneficially improve operational efficiency, and angular and diffraction bandwidths in such devices, while decreasing the propensity for optical artifacts and enabling light weight construction. According to various embodiments, an optical modulator may include an organic solid crystal (OSC) layer that is located proximate to, or sandwiched between, one or more electrodes.

In some embodiments, in response to an applied current or an applied voltage, the refractive index and/or birefringence of the OSC layer may be tuned by an amount of at least approximately 0.0005. In further embodiments, absorption by the OSC layer over a prescribed wavelength band may be modulated by 10% or more. Example OSC-containing optical modulators may include resistor or capacitor architectures that may be used independently or co-integrated with other modulators and implemented as, or incorporated into, surface relief gratings, photonic integrated circuits, Mach-Zehnder interferometers, reflective and refractive polarizers, volume Bragg gratings, and active geometric and diffractive lenses.

An electron withdrawing group, such as a halogen atom, may be added to an organic small molecule to promote the formation of defect-free or substantially defect-free organic solid crystal (OSC) thin films. For instance, the incorporation of an electron withdrawing group may be used to modulate the HOMO-LUMO gap of the molecule and accordingly impact the refractive index of the crystal. In particular embodiments, an increased refractive index may be realized due to improved intermolecular interactions. In various embodiments, electron withdrawing group-substituted OSC's may be used in thin film applications for active and passive optics to improve device efficiency and performance, increase angular and diffraction bandwidth, and lower device weight.

Example processes may be integrated with a real-time feedback loop that is configured to assess one or more attributes of the organic solid crystal thin film or fiber and accordingly adjust one or more process variables. Resultant organic solid crystal structures may be incorporated into optical elements such as AR/VR headsets and other devices, e.g., waveguides, prisms, Fresnel lenses, and the like.

EXAMPLE EMBODIMENTS

Example 1: A thin film includes an anisotropic organic molecule and an electron withdrawing group (EWG) bonded to the anisotropic organic molecules.

Example 2: The thin film of Example 1, where the thin film is crystalline. Example 3: The thin film of any of Examples 1 and 2, where the thin film is a single crystal.

Example 4: The thin film of any of Examples 1-3, where the film includes mutually orthogonal in-plane refractive indices ($n_x$ and $n_y$) and a through thickness refractive index ($n_z$), with $n_x$>1.4, $n_y$>1.4, $n_z$>1.4, $\Delta n_{xy} \geq 0.1$, $\Delta n_{xy} > \Delta n_{xz}$, and $\Delta n_{xy} > \Delta n_{yz}$.

Example 5: The thin film of any of Examples 1-4, where the anisotropic organic molecule is selected from anthracene, phenanthrene, tolane, thiophene, pyrene, corannulene, fluorene, biphenyl, and ter-phenyl.

Example 6: The thin film of any of Examples 1-5, where the electron withdrawing group comprises an electronegativity of at least approximately 2.5.

Example 7: The thin film of any of Examples 1-6, where the electron withdrawing group is selected from fluorine, chlorine, bromine, iodine, phenylalanine, nitrogen dioxide, sulfur trioxide, mesylate, acetyl, carboxyl, aldehyde, and sulfur ammonia.

Example 8: The thin film of any of Examples 1-7, where the electron withdrawing group is configured to change the polarizability of the anisotropic organic molecule.

Example 9: The thin film of any of Examples 1-8, where the electron withdrawing group is configured to generate intermolecular forces in an amount effective to change the polarizability of the anisotropic organic molecule.

Example 10: The thin film of any of Examples 1-9, where the electron withdrawing group is configured to improve a packing density of the anisotropic organic molecule.

Example 11: The thin film of any of Examples 1-10, where the electron withdrawing group is configured to increase a refractive index of the thin film along at least one crystallographic direction.

Example 12: An artificial reality headset including the thin film of any of Examples 1-11.

Example 13: A thin film including an organic crystalline phase and the organic crystalline phase including an organic molecule and an electron withdrawing group (EWG) bonded to the anisotropic organic molecule.

Example 14: The thin film of any of Example 13, where the thin film is a single crystal.

Example 15: The thin film of any of Examples 13 and 14, where the organic crystalline phase includes a heterocycle selected from furan, pyrrole, thiophene, pyridine, pyrimidine, and piperidine.

Example 16: The thin film of any of Examples 13-15, where the organic crystalline phase includes a dopant selected from fluorine, chlorine, nitrogen, oxygen, sulfur, and phosphorus.

Example 17: An optical modulator comprising an organic solid crystal thin film including an organic molecule and an electron withdrawing group (EWG) bonded to the organic molecule, a primary electrode disposed over a first region of the organic solid crystal thin film, and a secondary electrode disposed over a second region of the organic solid crystal thin film, where an optical property of the organic solid crystal thin film is configured to change in response to a changing voltage between the primary electrode and the secondary electrode.

Example 18: The optical modulator of Example 17, where the organic solid crystal thin film includes a single crystal.

Example 19: The optical modulator of any of Examples 17 and 18, where the primary electrode and the secondary electrode are each optically transparent.

Example 20: The optical modulator of any of Examples 17-19, where changing the voltage changes at least one of a refractive index of the organic solid crystal thin film by at least approximately 0.0005, a birefringence of the organic solid crystal thin film by at least approximately 0.0005, and an amount of visible light absorbed by the organic solid crystal thin film by at least approximately 10%.

Embodiments of the present disclosure may include or be implemented in conjunction with various types of artificial-reality systems. Artificial reality is a form of reality that has been adjusted in some manner before presentation to a user, which may include, for example, a virtual reality, an augmented reality, a mixed reality, a hybrid reality, or some combination and/or derivative thereof. Artificial-reality content may include completely computer-generated content or computer-generated content combined with captured (e.g., real-world) content. The artificial-reality content may include video, audio, haptic feedback, or some combination thereof, any of which may be presented in a single channel or in multiple channels (such as stereo video that produces a three-dimensional (3D) effect to the viewer). Additionally, in some embodiments, artificial reality may also be associated with applications, products, accessories, services, or some combination thereof, that are used to, for example, create content in an artificial reality and/or are otherwise used in (e.g., to perform activities in) an artificial reality.

Artificial-reality systems may be implemented in a variety of different form factors and configurations. Some artificial-reality systems may be designed to work without near-eye displays (NEDs). Other artificial-reality systems may include an NED that also provides visibility into the real world (such as, e.g., augmented-reality system 3600 in SLIDE 36) or that visually immerses a user in an artificial reality (such as, e.g., virtual-reality system 3700 in SLIDE 37). While some artificial-reality devices may be self-contained systems, other artificial-reality devices may communicate and/or coordinate with external devices to provide an artificial-reality experience to a user. Examples of such external devices include handheld controllers, mobile devices, desktop computers, devices worn by a user, devices worn by one or more other users, and/or any other suitable external system.

Turning to SLIDE 36, augmented-reality system 3600 may include an eyewear device 3602 with a frame 3610 configured to hold a left display device 3615(A) and a right display device 3615(B) in front of a user's eyes. Display devices 3615(A) and 3615(B) may act together or independently to present an image or series of images to a user. While augmented-reality system 3600 includes two displays, embodiments of this disclosure may be implemented in augmented-reality systems with a single NED or more than two NEDs.

In some embodiments, augmented-reality system 3600 may include one or more sensors, such as sensor 3640. Sensor 3640 may generate measurement signals in response to motion of augmented-reality system 3600 and may be located on substantially any portion of frame 3610. Sensor 3640 may represent one or more of a variety of different sensing mechanisms, such as a position sensor, an inertial measurement unit (IMU), a depth camera assembly, a structured light emitter and/or detector, or any combination thereof. In some embodiments, augmented-reality system 3600 may or may not include sensor 3640 or may include more than one sensor. In embodiments in which sensor 3640 includes an IMU, the IMU may generate calibration data based on measurement signals from sensor 3640. Examples of sensor 3640 may include, without limitation, accelerometers, gyroscopes, magnetometers, other suitable types of sensors that detect motion, sensors used for error correction of the IMU, or some combination thereof.

In some examples, augmented-reality system 3600 may also include a microphone array with a plurality of acoustic transducers 3620(A)-3620(J), referred to collectively as acoustic transducers 3620. Acoustic transducers 3620 may represent transducers that detect air pressure variations induced by sound waves. Each acoustic transducer 3620 may be configured to detect sound and convert the detected sound into an electronic format (e.g., an analog or digital format). The microphone array in SLIDE 36 may include, for example, ten acoustic transducers: 3620(A) and 3620(B), which may be designed to be placed inside a corresponding ear of the user, acoustic transducers 3620(C), 3620(D), 3620(E), 3620(F), 3620(G), and 3620(H), which may be positioned at various locations on frame 3610, and/or acoustic transducers 3620(1) and 3620(J), which may be positioned on a corresponding neckband 3605.

In some embodiments, one or more of acoustic transducers 3620(A)-(J) may be used as output transducers (e.g., speakers). For example, acoustic transducers 3620(A) and/or 3620(B) may be earbuds or any other suitable type of headphone or speaker.

The configuration of acoustic transducers 3620 of the microphone array may vary. While augmented-reality system 3600 is shown in SLIDE 36 as having ten acoustic transducers 3620, the number of acoustic transducers 3620 may be greater or less than ten. In some embodiments, using higher numbers of acoustic transducers 3620 may increase the amount of audio information collected and/or the sensitivity and accuracy of the audio information. In contrast, using a lower number of acoustic transducers 3620 may decrease the computing power required by an associated controller 3650 to process the collected audio information. In addition, the position of each acoustic transducer 3620 of the microphone array may vary. For example, the position of an acoustic transducer 3620 may include a defined position on the user, a defined coordinate on frame 3610, an orientation associated with each acoustic transducer 3620, or some combination thereof.

Acoustic transducers 3620(A) and 3620(B) may be positioned on different parts of the user's ear, such as behind the pinna, behind the tragus, and/or within the auricle or fossa. Or, there may be additional acoustic transducers 3620 on or surrounding the ear in addition to acoustic transducers 3620 inside the ear canal. Having an acoustic transducer 3620 positioned next to an ear canal of a user may enable the microphone array to collect information on how sounds arrive at the ear canal. By positioning at least two of acoustic transducers 3620 on either side of a user's head (e.g., as binaural microphones), augmented-reality device 3600 may simulate binaural hearing and capture a 3D stereo sound field around about a user's head.

In some embodiments, acoustic transducers 3620(A) and 3620(B) may be connected to augmented-reality system 3600 via a wired connection 3630, and in other embodiments acoustic transducers 3620(A) and 3620(B) may be connected to augmented-reality system 3600 via a wireless connection (e.g., a BLUETOOTH connection). In still other embodiments, acoustic transducers 3620(A) and 3620(B) may not be used at all in conjunction with augmented-reality system 3600.

Acoustic transducers 3620 on frame 3610 may be positioned in a variety of different ways, including along the length of the temples, across the bridge, above or below display devices 3615(A) and 3615(B), or some combination thereof. Acoustic transducers 3620 may also be oriented such that the microphone array is able to detect sounds in a wide range of directions surrounding the user wearing the augmented-reality system 3600. In some embodiments, an optimization process may be performed during manufacturing of augmented-reality system 3600 to determine relative positioning of each acoustic transducer 3620 in the microphone array.

In some examples, augmented-reality system 3600 may include or be connected to an external device (e.g., a paired device), such as neckband 3605. Neckband 3605 generally represents any type or form of paired device. Thus, the following discussion of neckband 3605 may also apply to various other paired devices, such as charging cases, smart watches, smart phones, wrist bands, other wearable devices, hand-held controllers, tablet computers, laptop computers, other external compute devices, etc.

As shown, neckband 3605 may be coupled to eyewear device 3602 via one or more connectors. The connectors may be wired or wireless and may include electrical and/or non-electrical (e.g., structural) components. In some cases, eyewear device 3602 and neckband 3605 may operate independently without any wired or wireless connection between them. While SLIDE 36 illustrates the components of eyewear device 3602 and neckband 3605 in example locations on eyewear device 3602 and neckband 3605, the components may be located elsewhere and/or distributed differently on eyewear device 3602 and/or neckband 3605. In some embodiments, the components of eyewear device 3602 and neckband 3605 may be located on one or more additional peripheral devices paired with eyewear device 3602, neckband 3605, or some combination thereof.

Pairing external devices, such as neckband 3605, with augmented-reality eyewear devices may enable the eyewear devices to achieve the form factor of a pair of glasses while still providing sufficient battery and computation power for expanded capabilities. Some or all of the battery power, computational resources, and/or additional features of augmented-reality system 3600 may be provided by a paired device or shared between a paired device and an eyewear device, thus reducing the weight, heat profile, and form factor of the eyewear device overall while still retaining desired functionality. For example, neckband 3605 may allow components that would otherwise be included on an eyewear device to be included in neckband 3605 since users may tolerate a heavier weight load on their shoulders than they would tolerate on their heads. Neckband 3605 may also have a larger surface area over which to diffuse and disperse heat to the ambient environment. Thus, neckband 3605 may allow for greater battery and computation capacity than might otherwise have been possible on a stand-alone eyewear device. Since weight carried in neckband 3605 may be less invasive to a user than weight carried in eyewear device 3602, a user may tolerate wearing a lighter eyewear device and carrying or wearing the paired device for greater lengths of time than a user would tolerate wearing a heavy stand-alone eyewear device, thereby enabling users to more fully incorporate artificial-reality environments into their day-to-day activities.

Neckband 3605 may be communicatively coupled with eyewear device 3602 and/or to other devices. These other devices may provide certain functions (e.g., tracking, localizing, depth mapping, processing, storage, etc.) to augmented-reality system 3600. In the embodiment of SLIDE 36, neckband 3605 may include two acoustic transducers (e.g., 3620(I) and 3620(J)) that are part of the microphone array (or potentially form their own microphone subarray). Neckband 3605 may also include a controller 3625 and a power source 3635.

Acoustic transducers 3620(I) and 3620(J) of neckband 3605 may be configured to detect sound and convert the detected sound into an electronic format (analog or digital). In the embodiment of SLIDE 36, acoustic transducers 3620 (I) and 3620(J) may be positioned on neckband 3605, thereby increasing the distance between the neckband acoustic transducers 3620(I) and 3620(J) and other acoustic transducers 3620 positioned on eyewear device 3602. In some cases, increasing the distance between acoustic transducers 3620 of the microphone array may improve the accuracy of beamforming performed via the microphone array. For example, if a sound is detected by acoustic transducers 3620(C) and 3620(D) and the distance between acoustic transducers 3620(C) and 3620(D) is greater than, e.g., the distance between acoustic transducers 3620(D) and 3620(E), the determined source location of the detected sound may be more accurate than if the sound had been detected by acoustic transducers 3620(D) and 3620(E).

Controller 3625 of neckband 3605 may process information generated by the sensors on neckband 3605 and/or augmented-reality system 3600. For example, controller 3625 may process information from the microphone array that describes sounds detected by the microphone array. For each detected sound, controller 3625 may perform a direction-of-arrival (DOA) estimation to estimate a direction from which the detected sound arrived at the microphone array. As the microphone array detects sounds, controller 3625 may populate an audio data set with the information. In embodiments in which augmented-reality system 3600 includes an inertial measurement unit, controller 3625 may compute all inertial and spatial calculations from the IMU located on eyewear device 3602. A connector may convey information between augmented-reality system 3600 and neckband 3605 and between augmented-reality system 3600 and controller 3625. The information may be in the form of optical data, electrical data, wireless data, or any other transmittable data form. Moving the processing of information generated by augmented-reality system 3600 to neckband 3605 may reduce weight and heat in eyewear device 3602, making it more comfortable to the user.

Power source 3635 in neckband 3605 may provide power to eyewear device 3602 and/or to neckband 3605. Power source 3635 may include, without limitation, lithium ion batteries, lithium-polymer batteries, primary lithium batteries, alkaline batteries, or any other form of power storage. In some cases, power source 3635 may be a wired power source. Including power source 3635 on neckband 3605 instead of on eyewear device 3602 may help better distribute the weight and heat generated by power source 3635.

As noted, some artificial-reality systems may, instead of blending an artificial reality with actual reality, substantially replace one or more of a user's sensory perceptions of the real world with a virtual experience. One example of this type of system is a head-worn display system, such as virtual-reality system 3700 in SLIDE 37, that mostly or completely covers a user's field of view. Virtual-reality system 3700 may include a front rigid body 3702 and a band 3704 shaped to fit around a user's head. Virtual-reality system 3700 may also include output audio transducers 3706(A) and 3706(B). Furthermore, while not shown in SLIDE 37, front rigid body 3702 may include one or more electronic elements, including one or more electronic displays, one or more inertial measurement units (IMUS), one or more tracking emitters or detectors, and/or any other suitable device or system for creating an artificial-reality experience.

Artificial-reality systems may include a variety of types of visual feedback mechanisms. For example, display devices in augmented-reality system 3600 and/or virtual-reality system 3700 may include one or more liquid crystal displays (LCDs), light emitting diode (LED) displays, microLED displays, organic LED (OLED) displays, digital light project (DLP) micro-displays, liquid crystal on silicon (LCoS) micro-displays, and/or any other suitable type of display screen. These artificial-reality systems may include a single display screen for both eyes or may provide a display screen for each eye, which may allow for additional flexibility for varifocal adjustments or for correcting a user's refractive error. Some of these artificial-reality systems may also include optical subsystems having one or more lenses (e.g., concave or convex lenses, Fresnel lenses, adjustable liquid lenses, etc.) through which a user may view a display screen. These optical subsystems may serve a variety of purposes, including to collimate (e.g., make an object appear at a greater distance than its physical distance), to magnify (e.g., make an object appear larger than its actual size), and/or to relay (to, e.g., the viewer's eyes) light. These optical subsystems may be used in a non-pupil-forming architecture (such as a single lens configuration that directly collimates light but results in so-called pincushion distortion) and/or a pupil-forming architecture (such as a multi-lens configuration that produces so-called barrel distortion to nullify pincushion distortion).

In addition to or instead of using display screens, some of the artificial-reality systems described herein may include one or more projection systems. For example, display devices in augmented-reality system 3600 and/or virtual-reality system 3700 may include microLED projectors that project light (using, e.g., a waveguide) into display devices, such as clear combiner lenses that allow ambient light to pass through. The display devices may refract the projected light toward a user's pupil and may enable a user to simultaneously view both artificial-reality content and the real world. The display devices may accomplish this using any of a variety of different optical components, including waveguide components (e.g., holographic, planar, diffractive, polarized, and/or reflective waveguide elements), light-manipulation surfaces and elements (such as diffractive, reflective, and refractive elements and gratings), coupling elements, etc. Artificial-reality systems may also be configured with any other suitable type or form of image projection system, such as retinal projectors used in virtual retina displays.

The artificial-reality systems described herein may also include various types of computer vision components and subsystems. For example, augmented-reality system 3600 and/or virtual-reality system 3700 may include one or more optical sensors, such as two-dimensional (2D) or 3D cameras, structured light transmitters and detectors, time-of-flight depth sensors, single-beam or sweeping laser rangefinders, 3D LiDAR sensors, and/or any other suitable type or form of optical sensor. An artificial-reality system may process data from one or more of these sensors to identify a location of a user, to map the real world, to provide a user with context about real-world surroundings, and/or to perform a variety of other functions.

The artificial-reality systems described herein may also include one or more input and/or output audio transducers. Output audio transducers may include voice coil speakers, ribbon speakers, electrostatic speakers, piezoelectric speakers, bone conduction transducers, cartilage conduction transducers, tragus-vibration transducers, and/or any other suitable type or form of audio transducer. Similarly, input audio transducers may include condenser microphones, dynamic microphones, ribbon microphones, and/or any other type or form of input transducer. In some embodiments, a single transducer may be used for both audio input and audio output.

In some embodiments, the artificial-reality systems described herein may also include tactile (i.e., haptic) feedback systems, which may be incorporated into headwear, gloves, body suits, handheld controllers, environmental devices (e.g., chairs, floormats, etc.), and/or any other type of device or system. Haptic feedback systems may provide various types of cutaneous feedback, including vibration, force, traction, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independent of other artificial-reality devices, within other artificial-reality devices, and/or in conjunction with other artificial-reality devices.

By providing haptic sensations, audible content, and/or visual content, artificial-reality systems may create an entire virtual experience or enhance a user's real-world experience in a variety of contexts and environments. For instance, artificial-reality systems may assist or extend a user's perception, memory, or cognition within a particular environment. Some systems may enhance a user's interactions with other people in the real world or may enable more immersive interactions with other people in a virtual world. Artificial-reality systems may also be used for educational purposes (e.g., for teaching or training in schools, hospitals, government organizations, military organizations, business enterprises, etc.), entertainment purposes (e.g., for playing video games, listening to music, watching video content, etc.), and/or for accessibility purposes (e.g., as hearing aids, visual aids, etc.). The embodiments disclosed herein may enable or enhance a user's artificial-reality experience in one or more of these contexts and environments and/or in other contexts and environments.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the present disclosure. The embodiments disclosed herein should be considered in all respects illustrative and not restrictive. Reference should be made to the appended claims and their equivalents in determining the scope of the present disclosure.

Unless otherwise noted, the terms “connected to” and “coupled to” (and their derivatives), as used in the specification and claims, are to be construed as permitting both direct and indirect (i.e., via other elements or components) connection. In addition, the terms “a” or “an,” as used in the specification and claims, are to be construed as meaning “at least one of.” Finally, for ease of use, the terms “including” and “having” (and their derivatives), as used in the specification and claims, are interchangeable with and have the same meaning as the word “comprising.”

As used herein, the term “approximately” in reference to a particular numeric value or range of values may, in certain embodiments, mean and include the stated value as well as all values within 10% of the stated value. Thus, by way of example, reference to the numeric value “50” as “approximately 50” may, in certain embodiments, include values equal to 50±5, i.e., values within the range 45 to 55.

As used herein, the term “substantially” in reference to a given parameter, property, or condition may mean and include to a degree that one of ordinary skill in the art would understand that the given parameter, property, or condition is met with a small degree of variance, such as within acceptable manufacturing tolerances. By way of example, depending on the particular parameter, property, or condition that is substantially met, the parameter, property, or condition may be at least approximately 90% met, at least approximately 95% met, or even at least approximately 99% met.

It will be understood that when an element such as a layer or a region is referred to as being formed on, deposited on, or disposed “on” or “over” another element, it may be located directly on at least a portion of the other element, or one or more intervening elements may also be present. In contrast, when an element is referred to as being “directly on” or “directly over” another element, it may be located on at least a portion of the other element, with no intervening elements present.

While various features, elements or steps of particular embodiments may be disclosed using the transitional phrase “comprising,” it is to be understood that alternative embodiments, including those that may be described using the transitional phrases “consisting of” or “consisting essentially of,” are implied. Thus, for example, implied alternative embodiments to a non-volatile medium material that comprises or includes paraffin oil include embodiments where a non-volatile medium material consists essentially of paraffin oil and embodiments where a non-volatile medium material consists of paraffin oil.

What is claimed is:

1. A thin film comprising:

an anisotropic organic molecule; and an electron withdrawing group (EWG) bonded to the anisotropic organic molecule, wherein the electron withdrawing group is configured to change the polarizability of the anisotropic organic molecule.

2. The thin film of claim 1, wherein the thin film is crystalline.

3. The thin film of claim 1, wherein the thin film is a single crystal.

4. The thin film of claim 1, wherein the thin film comprises mutually orthogonal in-plane refractive indices ($n_x$ and $n_y$) and a through thickness refractive index ($n_z$), with $n_x>1.4$, $n_y>1.4$, $n_z>1.4$, $\Delta n_{xy}\geq 0.1$, $\Delta n_{xy}>\Delta n_{xz}$, and $\Delta n_{xy}>\Delta n_{yz}$.

5. The thin film of claim 1, wherein the anisotropic organic molecule is selected from the group consisting of anthracene, phenanthrene, tolane, thiophene, pyrene, corannulene, fluorene, biphenyl, and ter-phenyl.

6. The thin film of claim 1, wherein the electron withdrawing group comprises an electronegativity of at least approximately 2.5.

7. The thin film of claim 1, wherein the electron withdrawing group is selected from the group consisting of fluorine, chlorine, bromine, iodine, phenylalanine, nitrogen dioxide, sulfur trioxide, mesylate, acetyl, carboxyl, aldehyde, and sulfur ammonia.

8. The thin film of claim 1, wherein the electron withdrawing group is configured to generate intermolecular forces in an amount effective to change the polarizability of the anisotropic organic molecule.

9. The thin film of claim 1, wherein the electron withdrawing group is configured to improve a packing density of the anisotropic organic molecule.

10. The thin film of claim 1, wherein the electron withdrawing group is configured to increase a refractive index of the thin film along at least one crystallographic direction.

11. An artificial reality headset comprising the thin film of claim 1.

12. A thin film comprising:

an organic crystalline phase, the organic crystalline phase comprising an organic molecule and an electron withdrawing group (EWG) bonded to the anisotropic organic molecule, wherein the organic crystalline phase comprises a dopant selected from the group consisting of fluorine, chlorine, nitrogen, oxygen, sulfur, and phosphorus.

13. The thin film of claim 12, wherein the thin film is a single crystal.

14. The thin film of claim 12, wherein the organic crystalline phase comprises a heterocycle selected from the group consisting of furan, pyrrole, thiophene, pyridine, pyrimidine, and piperidine.

15. An optical modulator comprising:

an organic solid crystal thin film comprising an organic molecule and an electron withdrawing group (EWG) bonded to the organic molecule;

a primary electrode disposed over a first region of the organic solid crystal thin film; and a secondary electrode disposed over a second region of the organic solid crystal thin film, wherein an optical property of the organic solid crystal thin film is configured to change in response to a changing voltage between the primary electrode and the secondary electrode, wherein changing the voltage changes at least one of:

a refractive index of the organic solid crystal thin film by at least approximately 0.0005;

a birefringence of the organic solid crystal thin film by at least approximately 0.0005; and an amount of visible light absorbed by the organic solid crystal thin film by at least approximately 10%.

16. The optical modulator of claim 15, wherein the organic solid crystal thin film comprises a single crystal.

17. The optical modulator of claim 15, wherein the primary electrode and the secondary electrode are each optically transparent.

* * * * *